(12) United States Patent
Dubrow et al.

(10) Patent No.: US 7,303,727 B1
(45) Date of Patent: Dec. 4, 2007

(54) MICROFLUIDIC SAMPLE DELIVERY DEVICES, SYSTEMS, AND METHODS

(75) Inventors: Robert S. Dubrow, San Carlos, CA (US); Michael Greenstein, Los Altos, CA (US); Luc J. Bousse, Los Altos, CA (US); Khushroo Gandhi, Sunnyvale, CA (US)

(73) Assignee: Caliper Life Sciences, Inc, Mountain View, CA (US)

( * ) Notice: Subject to any disclaimer, the term of this patent is extended or adjusted under 35 U.S.C. 154(b) by 594 days.

(21) Appl. No.: 10/369,325

(22) Filed: Feb. 19, 2003

Related U.S. Application Data

(60) Provisional application No. 60/362,291, filed on Mar. 6, 2002.

(51) Int. Cl.
*B01L 3/02* (2006.01)
*B32B 5/02* (2006.01)
*B32B 27/04* (2006.01)
*B32B 27/12* (2006.01)
*G01N 15/06* (2006.01)

(52) U.S. Cl. ............ 422/100; 422/50; 422/58; 422/68.1; 422/81; 422/82; 422/101; 436/43; 436/53; 436/54; 436/63; 436/174; 436/180; 73/1.01; 73/1.02

(58) Field of Classification Search ........ 73/1.01, 73/1.02; 422/50, 58, 68.1, 81, 82, 100, 101; 436/43, 53, 54, 63, 174, 180
See application file for complete search history.

(56) References Cited

U.S. PATENT DOCUMENTS

| | | | |
|---|---|---|---|
| 5,271,724 A | 12/1993 | van Lintel | |
| 5,277,556 A | 1/1994 | van Lintel | |
| 5,375,979 A | 12/1994 | Trah | |
| 5,512,131 A | 4/1996 | Kumar et al. | |
| 5,571,398 A | 11/1996 | Karger et al. | |
| 5,572,023 A | 11/1996 | Caprioli | |
| 5,842,787 A | 12/1998 | Kopf-Sill et al. | |
| 5,872,010 A | 2/1999 | Karger et al. | |

(Continued)

FOREIGN PATENT DOCUMENTS

WO WO-9405414 3/1994

(Continued)

OTHER PUBLICATIONS

Bings, N.H. et al. "Microfluidic devices connected to fused-silica capillaries with minimal dead volume," *Anal. Chem.* (1999) 71:3292-3296.

(Continued)

*Primary Examiner*—Brian Sines
(74) *Attorney, Agent, or Firm*—Ann C. Petersen; Donald R. McKenna

(57) ABSTRACT

Methods and apparatus for delivering fluidic materials to sample destinations, including mass spectrometers for analysis are provided. In preferred embodiments, sample aliquots are electrosprayed from tapered spray tips of capillary elements into the orifices of mass spectrometric inlet systems. In certain embodiments, fluidic samples are orthogonally sprayed from capillary elements or other fluid conduits, whereas in other embodiments samples are sprayed after devices are rotated or otherwise translocated from sample sources to sample destinations. In still other embodiments, samples are sprayed from flexed or deflected capillary elements at selected sample destinations.

19 Claims, 25 Drawing Sheets

U.S. PATENT DOCUMENTS

| | | | |
|---|---|---|---|
| 5,885,470 | A | 3/1999 | Parce et al. |
| 5,942,443 | A | 8/1999 | Parce et al. |
| 5,969,353 | A * | 10/1999 | Hsieh .................... 250/288 |
| 5,972,187 | A | 10/1999 | Parce et al. |
| 6,071,478 | A | 6/2000 | Chow |
| 6,110,343 | A | 8/2000 | Ramsey et al. |
| 6,126,086 | A | 10/2000 | Browner et al. |
| 6,231,737 | B1 | 5/2001 | Ramsey et al. |
| 6,235,471 | B1 | 5/2001 | Knapp et al. |
| 6,245,227 | B1 | 6/2001 | Moon et al. |
| 6,251,343 | B1 | 6/2001 | Dubrow et al. |
| 6,284,113 | B1 | 9/2001 | Bjornson et al. |
| 6,391,622 | B1 * | 5/2002 | Knapp et al. ............ 435/285.2 |
| 6,416,642 | B1 | 7/2002 | Alajoki et al. |
| 6,459,080 | B1 | 10/2002 | Yin et al. |
| 6,478,238 | B1 | 11/2002 | Wachs et al. |
| 6,481,648 | B1 | 11/2002 | Zimmermann |
| 6,602,472 | B1 * | 8/2003 | Zimmermann et al. ..... 422/100 |
| 6,803,568 | B2 * | 10/2004 | Bousse et al. ............. 250/288 |
| 2001/0052460 | A1 | 12/2001 | Chien et al. |
| 2004/0075050 | A1 * | 4/2004 | Rossier et al. ............. 250/288 |

FOREIGN PATENT DOCUMENTS

| | | |
|---|---|---|
| WO | WO-9502189 | 1/1995 |
| WO | WO-9604547 | 2/1996 |
| WO | WO-9702357 | 1/1997 |
| WO | WO-0045172 | 8/2000 |
| WO | WO-0050172 | 8/2000 |
| WO | WO-0050642 | 8/2000 |
| WO | WO-0073799 | 12/2000 |
| WO | WO-0173396 | 10/2001 |
| WO | WO-0211887 | 2/2002 |

OTHER PUBLICATIONS

Chan, J.H. et al., "Microfabricated Polymer Devices for Automated Sample Delivery of Peptides for Analysis by Electrospray Ionization Tandem Mass Spectrometry," *Anal. Chem.*, (Oct. 1999) 71(20):4437-4444.

Enjalbal et al. "Mass spectrometry in combinatorial chemistry," *Mass Spectrom. Rev.* (2000) 19:139-161.

Figeys, D. et al. "A microfabricated device for rapid protein identification by microelectrospray ion trap mass spectrometry," *Anal. Chem.* (1997) 69:3153-3160.

Figeys, D. et al., "Microfabricated Device Coupled with an electrospray Ionization Quadrupole time-of-Fight Mass Spectrometer: Protein Identifications Based on Enhanced-Reslution Mass Spectrometry and Tandem Mass Spectrometry Data," *Rapid Communications In Mass Spectrometry*, (Aug. 1998) 12:1435-1444.

Figeys, D.et al., "An Integrated Microfluidic—Tandem Mass Spectrometry System for Automated Protein Analysis," *Anal. Chem.*, (Sep. 1998) 70(18):3728-3734.

Figeys, D. et al., "Nanoflow Solvent Gradient Delivery from a Microfabricated Device for Protein Identifications by Electrospray Ionization Mass Spectrometry," *Anal., Chem.*, (Sep. 1998) 70(18):3721-3727.

Gaskell "Electrospray: principles and practice," *J. Mass Spec.* (1997) 32:677-688.

Harrison et al. "Micromachining a Miniaturized Capillary Electrophoresis-Based Chemical Analysis System on a Chip," *Science* (1993) 261:895-897.

Jacobson et al., "High Speed Separations on a Microchip," *Anal. Chem.* (1994) 66:1114-1118.

Jacobson et al. "Open Channel Electrochromatography on a Microchip," *Anal. Chem.* (1994) 66:2369-2373.

Lazar, J. et al. "Subattornole-sensitivity microchip nanoelectrospray source with time-of-flight mass spectrometry detection," *Anal. Chem.* (1999) 71:3627-3631.

Lazar, J. et al. On-Chip Proteolytic Digestion and Analysis Using "Wrong Way Round" Electrospray Time of Flight Mass Spectrometry *Analytical Chemistry* (2001) 73(8): 1733-1739.

Li, J. et al., "Separation and Identification of Peptides from Gel-Isolated Membrane Proteins Using a Microfabricated Device for Combined Capillary Electrophoresis/Nanoelectrospray Mass Spectrometry," *Anal. Chem.*, (Feb. 1999) 72(3):599-609.

Li, J. et al., "Integration of Microfabricated Devices to Capillary Electrophoresis-Electrospray Mass Spectrometry Using a Low Dead Volume Connection: Application to Rapid Analyses of Proteolytic Digests," *Anal. Chem.*, (Aug. 1999) 71(15):3036-3045.

Li, J. et al., "Rapid and Sensitive Separation of Trace Level Protein Digests Using Microfabricated Devices Coupled to a Quadrupole-Time-of-Flight Mass Spectrometer," (2000) *Electrophoresis* 198-210.

Licklider, L. et al., "A Micromachined Chip-Based Electrospray Source for Mass Spectrometry," *Anal. Chem.*, (Jan. 2000) 72(2):367-375.

Ramsey et al. "Generating electrospray from microchip devices using electroosmotic pumping," *Anal. Chem.* (1997) 69:1174-1178.

Schultz et al. "A Fully Integrated Monolithic Microchip Electrospray Device for Mass Spectrometry," *Anal. Chem.* (2000) 72:4058-4063.

Wen, J. et al., "Microfabricated Isoelectric Focusing Device for Direct Electrospray Ionization—Mass Spectrometry," *Electrophoresis*, (2000) (21):191-197.

Xiang, F. et al., "An Integrated Microfabricated Device for Dual Microdialysis and On-Line ESI-Ion Trap Mass Spectrometry for Analysis of Complex Biological Samples," *Annal. Chem.*, (Apr. 1999) 71(8):1485-1490.

Xue, Q. et al., "Multichannel Microchip Electrospray Mass Spectrometry," *Anal. Chem.*, (Feb. 1997) 69:(3):426-430.

Xue, Q. et al., "Integrated Multichannel Microchip Electrospray Ionization Mass Spectrometry: Anaysis of Peptides from On Chip Trypitic Digestion of Melittin," (Jun. 1997) *Rapid Communications in Mass Spectrometry*, 11:1253-1256.

Zhang, B. et al. "Microfabricated devices for capillary electrophpreis—electrospspray mass spectrometry, "*Anal. Chem.* (Aug. 1999) 71(15):3258-3264.

Zhang, B. et al., "A Microdevice with Integrated Liquid Junction for Facile Peptide and Protein Analysis in Capillary Electrophoresis/Electrospray Mass Spectrometry," *Anal. Chem.*, (Mar. 2000) 72(5):1015-1022.

* cited by examiner

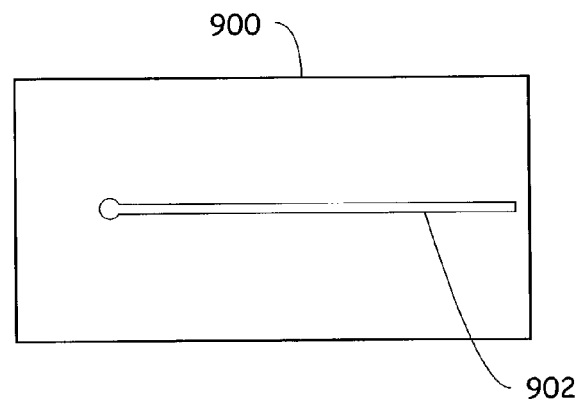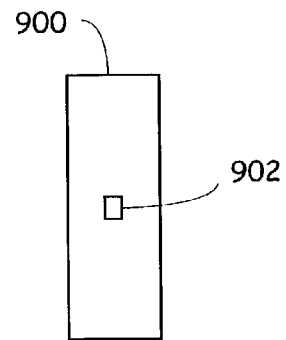
Fig. 9A  Fig. 9B
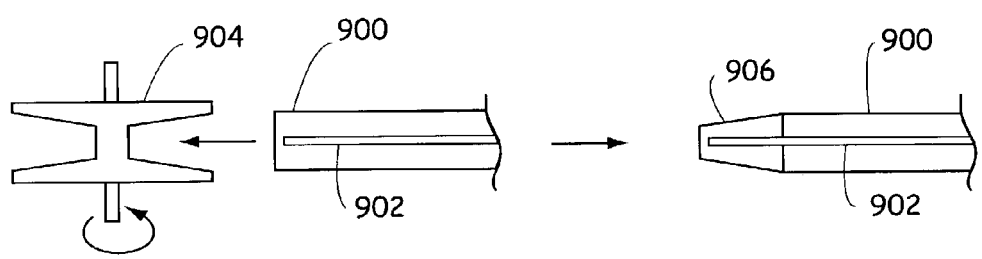
Fig. 9C

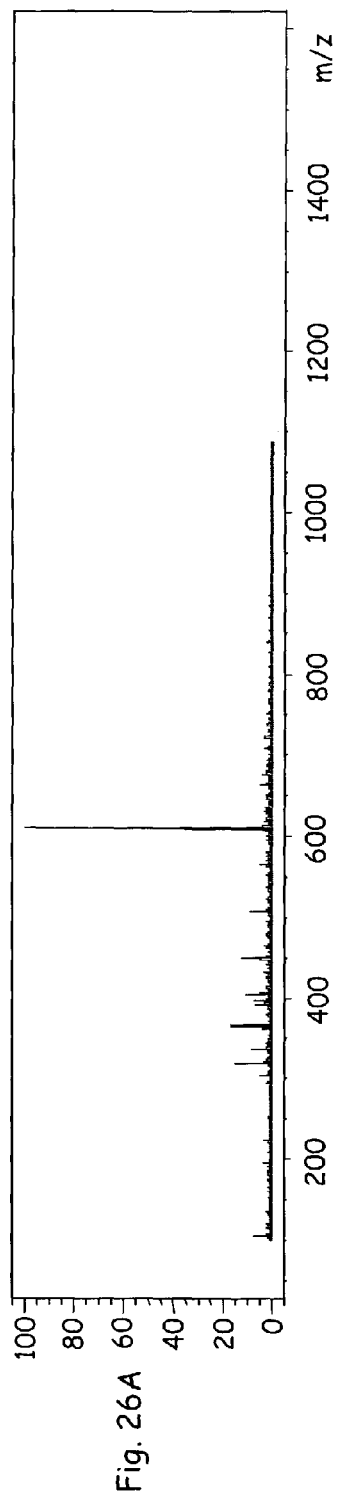
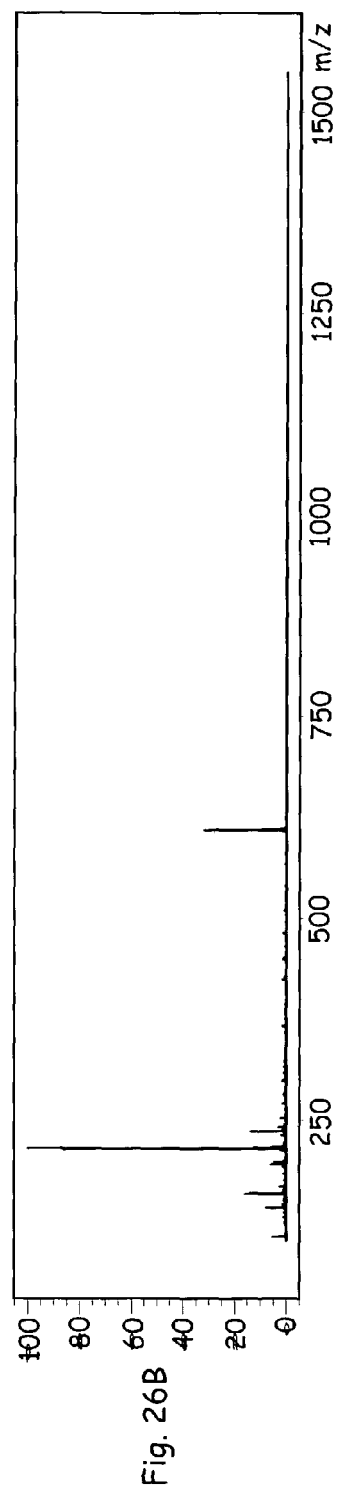
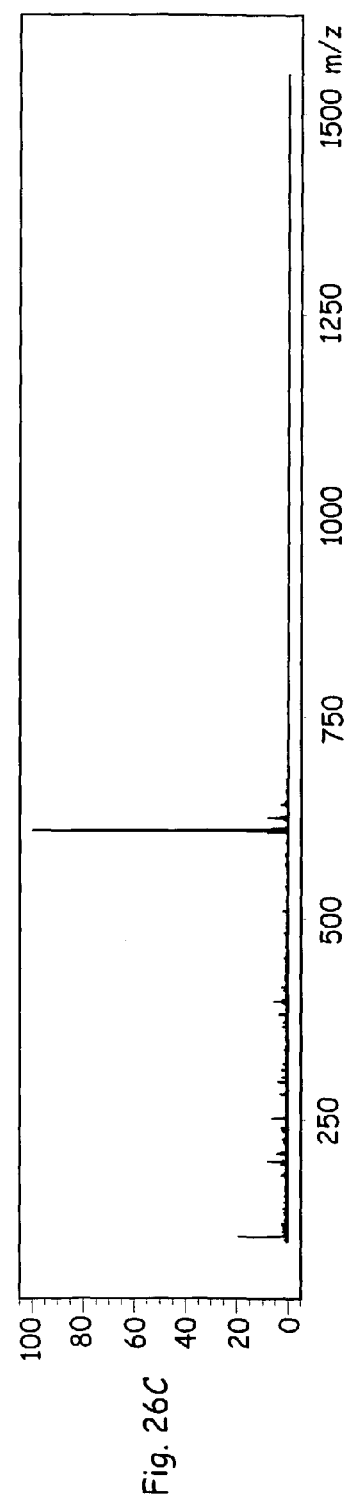
Fig. 26A
Fig. 26B
Fig. 26C

MICROFLUIDIC SAMPLE DELIVERY DEVICES, SYSTEMS, AND METHODS

CROSS-REFERENCES TO RELATED APPLICATIONS

Pursuant to 35 U.S.C. §§ 119 and/or 120, and any other applicable statute or rule, this application claims the benefit of and priority to U.S. Ser. No. 60/362,291, filed on Mar. 6, 2002, the disclosure of which is incorporated by reference.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to sample delivery utilizing microfluidic devices or systems. More specifically, the invention provides improved techniques and apparatus for delivering fluidic materials to detection systems, including mass spectrometers for analysis.

BACKGROUND OF THE INVENTION

Modern techniques of pharmaceutical discovery often include assaying or screening immense test compound libraries to assess the effect of library members on specific target molecules or biological systems. Combinatorial chemistry and associated technologies for generating molecular diversity are significantly increasing the number of test compounds available for such screening. In addition, genomic research is elucidating vast numbers of new target molecules against which the efficacy of these test compounds may be screened. However, the search for lead compounds in the development of new pharmacological agents is frequently impeded by a lack of sufficient assay throughput. The sources of limited throughput include inadequate methods and devices for delivering sample materials, especially solution-phase samples, to assay detection devices, such as mass spectrometers for analysis. In particular, many preexisting sample delivery technologies lack sufficient automation to rapidly and reliably accommodate the enormous numbers of compounds in the libraries currently being produced.

Mass spectrometers are commonly used analytical instruments that provide qualitative and quantitative information about sample components. In addition to well established uses in analytical chemistry, mass spectrometry is commonly used as a tool in biology, e.g., for proteomics, nucleic acid sequencing and the like. In general, mass spectrometers are widely used to elucidate chemical structures of both inorganic and organic molecules, to determine molecular weights, and to ascertain isotopic ratios of atoms in samples. A mass spectrometric system typically includes a system inlet, an ion source, a mass analyzer, and a detector. The detector is generally operably connected to a signal processor and a computer. General sources of information about mass spectrometry include, e.g., Skoog, et al. *Principles of Instrumental Analysis* (5$^{th}$ Ed.) Hardcourt Brace & Company, Orlando (1998), Busch and Lehman, *Guide to Mass Spectrometry*, V C H Publishers, Inc. (1999), Watson, *Introduction to Mass Spectrometry*, 3$^{rd}$, Lippincott-Raven Publishers (1997), Barker et al., *Mass Spectrometry*, 2$^{nd}$, John Wiley & Sons, Inc. (1999), Stroobant, *Mass Spectrometry: Principles and Applications*, 2$^{nd}$, John Wiley & Sons, Inc. (2001), Housby, *Mass Spectrometry and Genomic Analysis*, Kluwer Academic Publishers (2001), and Siuzdak, *Mass Spectrometry for Biotechnology*, Academic Press, Inc. (1996). Additional details relating to applications of mass spectrometry in combinatorial chemistry and pharmaceutical research are provided in, e.g., Kassel (2001) "Combinatorial chemistry and mass spectrometry in the 21st century drug discovery laboratory," *Chem. Rev.* 101:255-267, Papac and Shahrokh (2001) "Mass spectrometry innovations in drug discovery and development," *Pharmaceut. Res.* 18:131-145, Enjalbal et al. (2000) "Mass spectrometry in combinatorial chemistry," *Mass Spectrom. Rev.* 19:139-161, Matsushita et al. (2000) "Identification of peptide superagonists using combinatorial chemistry and mass spectrometry," *Nihon Rinsho Meneki Gakkai Kaishi* 23:571-576, Turteltaub and Vogel (2000) "Bioanalytical applications of accelerator mass spectrometry for pharmaceutical research," *Current Pharmaceutical Design* 6:991-1007, Niessen (1999) "State-of-the-art in liquid chromatography-mass spectrometry," *J. Chromatogr.* 856:179-197, Pramanik et al. (1999) "The role of mass spectrometry in the drug discovery process," *Curr. Opin. Drug. Disc. Develop.* 2:401-417, Sussmuth and Jung (1999) "Impact of mass spectrometry on combinatorial chemistry," *Journal of Chromatography B* 725:49-65, Swali et al. (1999) "Mass spectrometric analysis in combinatorial chemistry," *Curr. Opin. Chem. Biol.* 3:337-341, and Unger (1999) "Using mass spectrometry to determine ADME properties in drug discovery," *Annu. Rep. Med. Chem.* 34:307-316.

The formation of gaseous analyte ions for mass spectrometric analysis is generally accomplished using gas-phase or desorption ion sources. In particular, in a gas-phase ion source, a sample is first volatilized and then ionized. In contrast, solid- or liquid-phase samples, which often include nonvolatile or thermally unstable compounds, are directly converted into gaseous ions in desorption ion sources. One widely used desorption technique, especially for analyzing biopolymers or other species in excess of 100,000 daltons (Da), is electrospray ionization. Electrospray ionization, which can occur at atmospheric pressures and temperatures, is generated when a sufficient electrical potential difference is applied between a conductive or partly conductive fluid exiting, e.g., a capillary opening and an electrode so as to produce a concentration of electric field lines emerging from the capillary opening. When a positive voltage is applied to the capillary opening relative to, e.g., an extracting electrode at an ion-sampling orifice of a mass spectrometer, the electric field causes positively-charged ions in the fluidic sample to migrate to the surface of the fluid at the capillary opening. Negatively-charged ions will migrate to the fluid surface at the capillary opening, when a negative voltage is applied to the capillary opening relative to the extracting electrode. When the repulsive force of the ions at the fluid surface exceeds the surface tension of the fluid sample, a volume of the fluid forms a Taylor cone that extends from the capillary tip and charged droplets are drawn toward the extracting electrode. The resulting charged spray of fine droplets undergoes solvent evaporation and attachment of charge to analyte molecules in the droplets. As the charged droplets decrease in size due to the evaporation of solvent, their charge density increases such that ions are desorbed into the gaseous-phase. Significantly, the electrospray process typically produces only limited fragmentation of, e.g., large and thermally fragile biopolymers such that resultant mass spectra are greatly simplified relative to those generated using harder ion sources and often include only molecular ions or protonated molecular ions. Furthermore, electrospray ion sources are typically readily adapted to direct sample introduction into inlet systems following various upstream processing steps, including chromatographic (e.g., HPLC, etc.) and electrophoretic (e.g., capillary electrophoresis, etc.) separations. Additional information relating to electrospray ionization is described in, e.g., Cole (Ed.), *Electrospray Ionization Mass Spectrometry: Fundamentals, Instrumentation and Applications*, John Wiley & Sons, Inc. (1997) and Snyder (Ed.), *Biochemical and Biotechnological Applications of Electrospray Ionization Mass Spectrometry*, American Chemical Society (1995).

Preexisting apparatus and techniques generally lack sufficient automation and throughput to efficiently deliver significant numbers of fluidic samples, such as those produced by combinatorial synthesis, to detection devices for analysis or to other sample destinations. As a consequence, improved devices, systems, and methods of such fluid delivery would be desirable. More specifically, improved apparatus and methods for electrospraying fluidic samples for mass spectrometric or other gas-phase analyses would be particularly desirable. The present invention is directed to these and other features by providing automated, high-throughput microfluidic sample delivery devices or systems and to methods of using the same. These and many other attributes will be apparent upon complete review of the following disclosure.

SUMMARY OF THE INVENTION

The present invention generally relates to various microfluidic sample delivery devices and to assorted methods of delivering fluidic sample materials to sample destinations using the devices. In preferred embodiments, fluidic samples are orthogonally electrosprayed from tapered spray tips of capillary elements that extend from the devices of the invention. In certain other embodiments, samples are sprayed from devices that have been rotated from a sample source (e.g., a microwell plate, etc.) to a selected sample destination, such as an orifice of a mass spectrometric detection system. In still other embodiments, capillary elements are flexed, deflected, or otherwise moved between sample sources and sample destinations prior to spraying samples. Various other embodiments are also provided. The highly automated devices, systems, and methods of the invention dramatically increase assay throughput relative to preexisting apparatus and methods of fluid delivery in addition to providing many other significant advantages as described herein.

For example, the invention relates to a fluidic sample delivery device that includes (a) a holder (e.g., a microfluidic chip or other microfluidic device) including a flexible fluid conduit (e.g., a capillary element having a channel disposed therethrough or the like) extending therefrom, and (b) a fluid direction component operably connected to the flexible fluid conduit which draws selected aliquots of a fluidic sample from a sample source into the flexible fluid conduit and expels the selected aliquots from the flexible fluid conduit at a sample destination (e.g., an inlet to a mass spectrometer, etc.). In certain embodiments, the flexible fluid conduit includes a conductive coating operably connected to a power source to produce a potential gradient in the flexible fluid conduit. Optionally, the flexible fluid conduit includes a chromatographic material to separate at least one component of the selected aliquots from other components prior to being expelled at the sample destination. In preferred embodiments, the fluid direction component includes a pressure force modulator which applies pressure to draw the selected aliquots into the flexible fluid conduit and an electrokinetic force modulator which applies a potential gradient along a length of the flexible fluid conduit to electrospray the selected aliquots at the sample destination. The device further includes (c) a controller operably connected to one or more of the holder, the flexible fluid conduit, or the fluid direction component, which controller controllably flexes the flexible fluid conduit. The controller optionally controllably flexes the flexible fluid conduit between the sample source and the sample destination. As an additional option, the controller includes a flexible fluid conduit deflection component, which deflection component selectively deflects a terminus of the flexible fluid conduit into contact with the sample source.

The holder of the fluidic sample delivery device includes various embodiments. In preferred embodiments, for example, the holder includes a microfluidic device. The microfluidic device optionally includes at least one cavity that fluidly communicates with the flexible fluid conduit from which fluidic materials are capable of being flowed to wash the flexible fluid conduit. In other embodiments, the flexible fluid conduit includes at least a first terminus and at least a second terminus, the first terminus extending from a first portion of the holder and the second terminus extending from a second portion of the holder. The first portion typically includes a cavity into or through which the controller is capable of selectively deflecting the first terminus. Optionally, the cavity includes the sample source. In some embodiments, the cavity includes an array of cavities. In these embodiments, the holder optionally includes two or more flexible fluid conduits and the controller is capable of selectively deflecting the first terminus of at least one of the two or more flexible fluid conduits into or through a member of the array. Further, the fluid direction component is generally capable of flowing the selected sample aliquots out of second termini of the two or more fluid conduits sequentially or simultaneously at the sample destination.

In another aspect, the invention provides a method of delivering fluidic samples to a sample destination (e.g., an inlet to a mass spectrometer or the like). The method includes (a) providing a holder (e.g., a microfluidic device, etc.) that includes a flexible fluid conduit, (b) drawing a selected aliquot of a fluidic sample from a sample source into the flexible fluid conduit, (c) flexing the flexible fluid conduit from the sample source to the sample destination, and (d) expelling the selected aliquot from the flexible fluid conduit at the sample destination.

In some embodiments, the flexible fluid conduit is deflected into contact with the fluidic sample in the sample source prior to (b) using a fluid conduit deflection component. In other embodiments, the selected aliquot is drawn into the flexible fluid conduit through a first terminus of the flexible fluid conduit and expelled from the flexible fluid conduit through a second terminus of the flexible fluid conduit. For example, (b) optionally includes drawing the selected aliquot into the flexible fluid conduit using a pressure force modulator or an electrokinetic force modulator operably connected to the holder. In certain embodiments, (c) includes flexing the flexible fluid conduit using a controller that includes a mechanical arm operably connected to the flexible fluid conduit. In preferred embodiments, (d) includes electrospraying the selected aliquot from the flexible fluid conduit using an electrokinetic force modulator operably connected to the holder. In addition, the method optionally further includes (e) washing the flexible fluid conduit with at least one fluidic material. Typically, (b)-(e) are repeated.

In preferred embodiments, the holder includes a microfluidic device. In certain of these embodiments, the method further includes (e) flowing a fluidic material out of the flexible fluid conduit from a cavity of the microfluidic device that fluidly communicates with the flexible fluid conduit to wash the flexible fluid conduit. Optionally, a portion of the fluidic material is flowed to a waste cavity to reduce carryover at a joint between the flexible fluid conduit and a body structure of the microfluidic device. The holder generally includes multiple cavities and the method optionally further includes applying compensating force to fluids in cavities other than the cavity from which the fluidic material is flowed to reduce fluid backflow into the cavities. In certain embodiments, the microfluidic device comprises a plurality of flexible fluid conduits. In some of these embodiments, at least one of (b)-(d) is performed using at least two flexible fluid conduits.

In another aspect, the invention provides a sample delivery device that includes (a) a microfluidic device including (i) a body structure including microscale cavities disposed therein, and (ii) a capillary element extending from the body structure that fluidly communicates with the microscale cavities, which capillary element draws selected aliquots of a fluidic sample from a sample source. A channel of the capillary element typically includes a larger cross-sectional dimension than the nozzle. The microfluidic device also includes (iii) a nozzle fabricated or attached proximal to an edge of the body structure that includes at least a portion of the microscale cavities, which nozzle delivers the selected aliquots of the fluidic sample to a sample destination (e.g., an inlet to a mass spectrometer, etc.). Further, in certain embodiments, the portion includes a cross-sectional dimension that produces a surface tension on fluidic materials disposed therein sufficient to prevent voiding the fluidic materials from the nozzle when pressure is applied to the capillary element. The nozzle optionally includes a nozzle plate (e.g., a silicon nozzle plate or the like), which nozzle plate is attached to the body structure. Typically, thermal expansion coefficients of the body structure and the nozzle plate are approximately equal. Optionally, the nozzle includes an array of nozzles in which a member of the array fluidly communicates with the microscale cavities. For example, the members of the array are optionally disposed relative to one another such that the selected aliquots are capable of being delivered simultaneously from at least two nozzles to the sample destination. The sample delivery device further includes (b) a fluid direction component which flows the selected aliquots through the device from the sample source to the sample destination. In preferred embodiments, the fluid direction component includes a fluid pressure force modulator which applies pressure to draw the selected aliquots into the device through the capillary element and to flow the selected aliquots through the device. The fluid direction component typically further includes an electrokinetic force modulator which applies a potential gradient along a length of the microscale cavities and the nozzle to electrospray the selected aliquots from the nozzle at the sample destination. The sample delivery device typically further includes an automated controller operably connected to the device to move the device relative to the sample source and the sample destination.

In some embodiments, at least a segment of at least one of the microscale cavities and the nozzle include a conductive coating operably connected to a power source to produce a potential gradient in the segment. Optionally, at least one of the microscale cavities include a chromatographic material capable of separating at least one component of the selected aliquots from other components prior to flowing the selected aliquots to the sample destination. As an additional option, at least one of the microscale cavities further includes electrodes disposed therein, which electrodes are operably connected to a power source to electrophoretically separate at least one component of the selected aliquots from other components, prior to flowing the selected aliquots to the sample destination. These electrodes can also be used to generate the field used for electrospray. Typically, at least one of the microscale cavities includes a fluidic wash material suitable for washing the capillary element or the nozzle. In certain embodiments, the microscale cavities include a plurality of parallel microscale cavities and the nozzle includes an array of nozzles in which at least two members of the array fluidly communicate with different parallel microscale cavities. In other embodiments, the microscale cavities include a plurality of aligned microscale cavities in which at least two members of the plurality are spaced at different distances from one another along a length of an alignment and in which the nozzle includes an array of nozzles in which at least two members of the array fluidly communicate with different microscale cavities. In addition, the capillary element optionally includes a plurality of capillary elements extending therefrom in which at least one member of the plurality fluidly communicates with the microscale cavities.

The invention also relates to a method of delivering a fluidic sample to a sample destination. The method includes (a) providing a microfluidic device that includes (i) a body structure including microscale cavities disposed therein, and (ii) a capillary element extending from the body structure, which capillary element fluidly communicates with the microscale cavities. The body structure optionally includes a plurality of capillary elements extending therefrom in which at least one member of the plurality fluidly communicates with the microscale cavities. The microfluidic device also includes (iii) a nozzle fabricated or attached proximal to an edge of the body structure that includes at least a portion of the microscale cavities. Similarly, the device optionally includes a plurality of nozzles in which at least one member of the plurality fluidly communicates with the microscale cavities. The method additionally includes (b) drawing at least one selected aliquot of the fluidic sample from a sample source into the body structure through the capillary element, and (c) expelling the selected aliquot of the fluidic sample from the nozzle at the sample destination. A fluid flow rate is typically faster in (b) than in (c). In some embodiments, (b) and (c) include using a pressure force modulator to draw and expel the selected aliquot. In other embodiments, (b) includes drawing the selected aliquot using a pressure force modulator and (c) includes expelling the selected aliquot using an electrokinetic force modulator, e.g., to electrospray the selected aliquot from the nozzle. Optionally, the method further includes separating at least one component of the selected aliquot from other components prior to expelling the selected aliquot from the nozzle. In some embodiments, the method further includes (d) washing at least one of the capillary element and the nozzle with a buffer solution. Optionally, (b)-(d) are repeated.

In another aspect, the invention relates to a microfluidic sample delivery device that includes (a) a body structure, including microscale cavities disposed therein, and (b) a capillary element extending from the body structure that fluidly communicates with the microscale cavities, which capillary element includes a tapered spray tip. The tapered spray tip typically includes a nozzle. The sample delivery device also includes (c) a fluid direction component operably connected to the body structure, which fluid direction component is capable of drawing selected aliquots of a fluidic sample into at least the capillary element from a sample source and spraying the selected aliquots from the tapered spray tip proximal to or within a sample destination (e.g., an inlet to a detection device, such as a mass spectrometer or the like). An opening in the tapered spray tip is typically disposed substantially orthogonal to the inlet to the detection device. In one preferred embodiment, the fluid direction component is capable of spraying the selected aliquots substantially orthogonally from the tapered spray tip to the sample destination. Optionally, the microfluidic sample delivery device further includes (d) an electrical control system operably connected to at least the tapered spray tip and the sample destination, which electrical control system is capable of generating a potential difference between the tapered spray tip and the sample destination to electrospray the selected aliquots from the tapered spray tip proximal to the sample destination. As an additional option, the device further includes (e) an automated controller operably connected to one or more of the body structure, the fluid direction component, or another device component to direct operation of the device. In certain embodiments, the device further includes (f) a device handling system operably connected to the device, which device handling system is capable of selectively moving the device, or a portion the device, relative to the sample source and the sample destination. The device handling system is typically capable of translocating or rotating the device between the sample source and the sample destination. Optionally, the capillary element is flexible and the device handling system includes a capillary element flexing component operably connected to the capillary element, which capillary element flexing component is capable of selectively flexing the tapered spray tip of the capillary element between the sample source and the sample destination.

In some embodiments, the fluid direction component includes a fluid pressure force modulator that is capable of applying pressure to draw the selected aliquots into the capillary element. In these embodiments, the fluid direction component typically further includes an electrokinetic force modulator that is capable of applying a potential gradient along a length of the microscale cavities and/or the capillary element to spray the selected aliquots from the tapered spray tip proximal to the sample destination.

In certain embodiments, at least a segment of at least one of the microscale cavities and/or the tapered spray tip include a conductive coating operably connected to a power source to produce a potential gradient in the segment. Optionally, at least one of the microscale cavities include a fluidic material, which fluidic material is capable of being flowed out of the capillary element to wash a channel disposed within the capillary element. As an additional option, at least one of the microscale cavities include a fluidic sample material, which fluidic sample material is capable of being sprayed from the tapered spray tip proximal to or within the sample destination. The microscale cavities optionally include a plurality of parallel microscale cavities.

In some embodiments, the capillary element includes a plurality of capillary elements extending from the body structure in which at least one member of the plurality fluidly communicates with the microscale cavities. For example, the plurality of capillary elements optionally include first and second capillary elements, which second capillary element includes the tapered spray tip. Typically, a first channel disposed through the first capillary element includes a larger cross-sectional dimension than a second channel disposed through the second capillary element. In certain embodiments, at least one microscale cavity disposed between the first and second capillary elements within the body structure includes a separation region in which at least one component of the selected aliquots is capable of being separated from other components prior to being sprayed from the tapered tip proximal to the sample destination. Optionally, the separation region includes a chromatographic material to separate the at least one component of the selected aliquots from the other components. As an additional option, the separation region includes electrodes disposed therein, which electrodes are operably connected to an electrical control system to electrophoretically separate the at least one component of the selected aliquots from the other components. In some embodiments, the selected aliquots are capable of being drawn into the body structure from the sample source through the first capillary element and sprayed from the tapered spray tip of the second capillary element proximal to the sample destination. In these embodiments, the fluid direction component is typically capable of drawing the selected aliquots into the body structure at a higher flow rate than the selected aliquots are sprayed from the tapered spray tip.

In another aspect, the invention relates to a method of spraying a fluidic sample at least proximal to a sample destination. The method includes (a) providing a microfluidic device that includes (i) a body structure including microscale cavities disposed therein, and (ii) a capillary element extending from the body structure that fluidly communicates with the microscale cavities, which capillary element includes a tapered spray tip. The method also includes (b) drawing a selected aliquot of a fluidic sample from a sample source into at least the capillary element, and (c) spraying the selected aliquot from the tapered spray tip proximal to the sample destination. In some embodiments, (b) includes drawing the selected aliquot through the capillary element and into the body structure. In these embodiments, the selected aliquot is generally drawn into the body structure at a higher flow rate than the selected aliquot is sprayed from the tapered spray tip. In certain embodiments, the capillary element is flexible and (c) includes: (i) flexing the capillary element from the sample source to the sample destination, and (ii) spraying the selected aliquot from the tapered spray tip proximal to the sample destination. Further, the selected aliquot is typically substantially orthogonally sprayed from the tapered spray tip proximal to the sample destination. In preferred embodiments, (c) includes electrospraying the selected aliquot from the tapered spray tip proximal to the sample destination. Typically, (b) and (c) are performed using a fluid direction component operably connected to the body structure. In some embodiments, at least one of the microscale cavities includes a fluidic material disposed therein and the method further includes (d) flowing an aliquot of the fluidic material out of the tapered spray tip to wash the microfluidic device. The sample destination typically includes an inlet to a detection device (e.g., a mass spectrometer or the like) and the method optionally further includes (d) detecting a detectable signal produced by at least one component of the selected aliquot.

In some embodiments, (c) includes: (i) rotating the microfluidic device from the sample source to the sample destination, and (ii) spraying the selected aliquot from the tapered spray tip proximal to the sample destination. In these embodiments, the microfluidic device is typically rotated using a handling system operably connected to the microfluidic device. In other embodiments, (c) includes (i) moving the microfluidic device from the sample source proximal to the sample destination, and (ii) spraying the selected aliquot from the tapered spray tip proximal to the sample destination. In these embodiments, the microfluidic device is typically moved using a handling system operably connected to the microfluidic device.

In certain embodiments, the capillary element includes a plurality of capillary elements extending from the body structure in which at least one member of the plurality fluidly communicates with the microscale cavities. For example, the plurality of capillary elements optionally includes first and second capillary elements, which second capillary element includes the tapered spray tip. Typically, a first channel disposed through the first capillary element includes a larger cross-sectional dimension than a second channel disposed through the second capillary element. In some embodiments, at least one microscale cavity disposed between the first and second capillary elements within the body structure includes a separation region. In these embodiments, (b) optionally includes (i) drawing the selected aliquot of the fluidic sample through the first capillary element, and (ii) flowing the selected aliquot through the separation region to separate at least one component of the selected aliquot from other components prior to (c).

BRIEF DESCRIPTION OF THE DRAWING

FIGS. 9A-G schematically depicts the fabrication of a monolithic spray nozzle from the edge of a microfluidic device body structure according to one embodiment of the invention. In particular, FIG. 9A schematically shows a microchannel disposed in a body structure. FIG. 9B schematically shows the body structure of FIG. 9A from a side view. FIG. 9C schematically illustrates a process to chamfer an edge of the body structure of FIG. 9A. FIG. 9D schematically depicts the body structure of FIG. 9C after segments have been excised or diced from an edge of the body structure to define the gross structure of the monolithic spray nozzle. FIG. 9E schematically shows the device of FIG. 9D from a side view. FIG. 9F schematically depicts the body structure of FIG. 9D after the monolithic spray nozzle has been isotropically etched. FIG. 9G schematically illustrates the body structure of FIG. 9F from a side view.

FIGS. 26A-C are mass spectral traces showing detected components from a reserpine comparison.

DETAILED DISCUSSION OF THE INVENTION

I. Introduction

Figure 1:
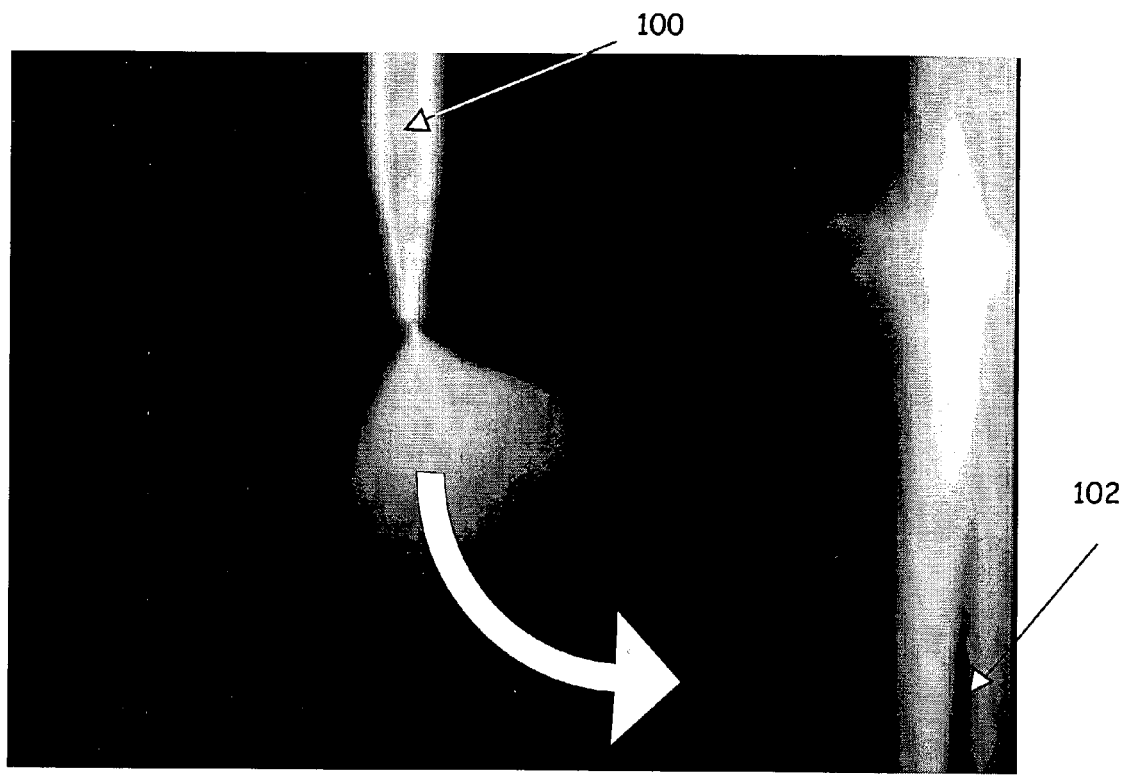
FIG. 1 is photograph that shows a sample aliquot being orthogonally electrosprayed from a tapered spray tip of a capillary element to an orifice of a mass spectrometer.

The present invention addresses, e.g., a need for apparatus and methods of delivering fluidic sample materials to sample destinations for analysis or processing with sufficient throughput to readily accommodate large compound libraries and assays involving such libraries. In particular, the invention provides microfluidic sample delivery devices and systems capable of rapidly delivering fluidic materials from sample sources, such as microwell plates to, e.g., various detection systems. In preferred embodiments and as emphasized herein for purposes of clarity of illustration, samples are electrosprayed proximal to mass spectrometric inlet system orifices to access the rich information content typically provided by this method of detection. Nonetheless, it will be appreciated by those of skill in the art that the apparatus and methods described herein are readily adaptable to other uses beyond mass spectrometric analysis (MS analysis), including but not limited to, other gas-phase analytical techniques or other modes of detection, which are generally known in the art.

Although various proposed techniques for delivering a sample to a mass spectrometric detector have been described in the art, all of these approaches typically lack sufficient throughput and automation to efficiently interface large numbers of samples with mass spectrometers. Some of these techniques are described in certain issued U.S. patents including, e.g., U.S. Pat. No. 6,126,086, entitled "OSCILLATING CAPILLARY NEBULIZER WITH ELECTROSPRAY," which issued Oct. 3, 2000 to Browner et al., U.S. Pat. No. 5,969,353, entitled "MICROFLUIDIC CHIP MASS SPECTROMETER INTERFACE," which issued Oct. 19, 1999 to Hsieh, U.S. Pat. No. 5,872,010, entitled "MICROSCALE FLUID HANDLING SYSTEM," which issued Feb. 16, 1999 to Karger et al., U.S. Pat. No. 5,572,023, entitled "ELECTROSPRAY METHODS AND APPARATUS FOR TRACE ANALYSIS," which issued Nov. 5, 1996 to Caprioli, and U.S. Pat. No. 6,245,227, entitled "INTEGRATED MONOLITHIC MICROFABRICATED ELECTROSPRAY AND LIQUID CHROMATOGRAPHY SYSTEM AND METHOD," which issued Jun. 12, 2001, which are incorporated by reference in their entirety for all purposes. Other proposed approaches to sample delivery are described in, e.g., Figeys et al. (1997) "A microfabricated device for rapid protein identification by microelectrospray ion trap mass spectrometry," Anal. Chem. 69:3153-3160, Ramsey et al. (1997) "Generating electrospray from microchip devices using electroosmotic pumping," Anal. Chem. 69:1174-1178, Lazar et al. (1999) "Subattomole-sensitivity microchip nanoelectrospray source with time-of-flight mass spectrometry detection," Anal. Chem. 71:3627-3631, Zhang et al. (1999) "Microfabricated devices for capillary electrophoresis-electrospray mass spectrometry," Anal. Chem. 71:3258-3264, Bings et al. (1999) "Microfluidic devices connected to fused-silica capillaries with minimal dead volume," Anal. Chem. 71:3292-3296, and Gaskell (1997) "Electrospray: principles and practice," J. Mass Spec. 32:677-688, which are incorporated by reference in their entirety for all purposes.

The following provides details regarding various aspects of the apparatus and methods of delivering fluidic materials of the present invention. It also provides details pertaining to certain upstream and downstream processes that are optionally performed in accordance with the invention.

II. Sample Delivery Apparatus and Methods

A. Overview of Selected Embodiments

In one preferred embodiment, the present invention provides a device (e.g., an axial spray pipetting device) that includes a body structure having microscale cavities (e.g., microchannel networks, etc.) disposed within the body structure. The device also includes at least one capillary element extending from the body structure. The capillary element fluidly communicates with the microscale cavities and includes a tapered spray tip (e.g., a nozzle or the like). In certain embodiments, the body structure includes multiple capillary elements. Additionally, the device includes a fluid direction component or system and/or an electrical control system operably connected to the body structure. These components or systems are capable of drawing selected aliquots of fluidic samples into at least the capillary element from a sample source, such as a well of a microwell plate (e.g., a 96 well plate, a 384 well plate, etc.) or the like. Further, these components or systems are also capable of spraying (e.g., electrospraying, etc.) the selected aliquots from the tapered spray tip at least proximal to a sample destination. Although other configurations are optionally utilized, the sample source and the sample destination are typically disposed about 90° apart relative to the microfluidic sample delivery device. In preferred embodiments, for example, sample aliquots are electrosprayed substantially orthogonally from tapered spray tips to sample destinations. To illustrate, FIG. 11s photograph that shows a sample aliquot being orthogonally electrosprayed from tapered spray tip 100 of a capillary element to mass spectrometer orifice 102. The channel disposed through tapered spray tip 100 included a 5 μm cross-sectional dimension and the sample aliquot was electrosprayed at 5 psi and 3 KV. In other embodiments, samples are sprayed from tapered spray tips following movement (e.g., rotation, etc.) of the sample delivery device, or a portion of the device (e.g., a flexible capillary element that includes a tapered sprayed tip, etc.), between the sample source and destination. In preferred embodiments, the sample destination is an inlet to a detection device. For example, in some embodiments, the detection device is a mass spectrometer, such as an atmospheric or sub-atmospheric pressure ionization mass spectrometer. Mass spectrometers and other detection devices are described in greater detail below.

Figure 2:
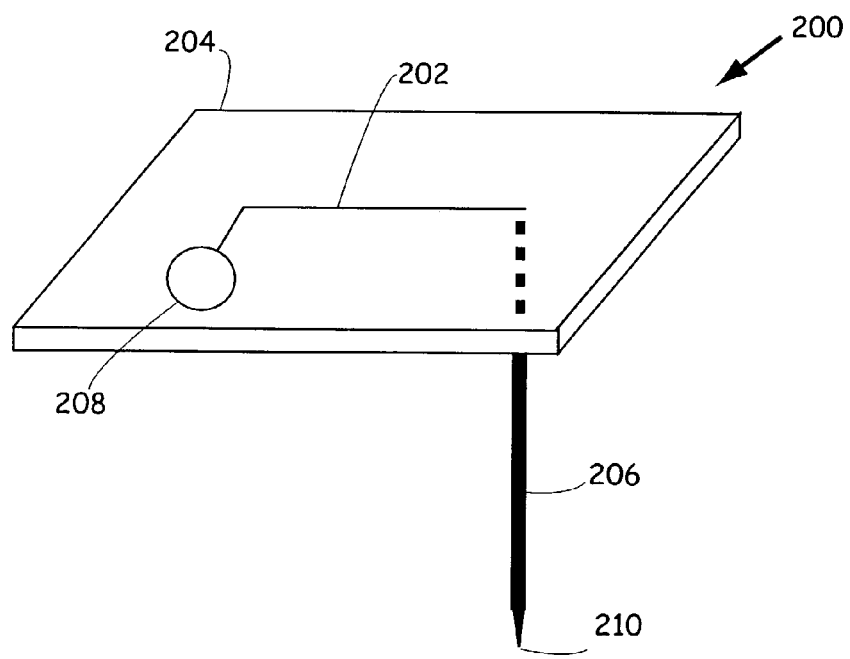
FIG. 2 schematically illustrates an embodiment of a microfluidic sample delivery device of the invention.

FIG. 2 schematically illustrates an embodiment of a microfluidic sample delivery device of the invention. As shown, sample delivery device 200 includes microchannel 202 fabricated within body structure 204. Microchannel 202 fluidly communicates with capillary element 206 and with well or port 208. As additionally shown, capillary element

206 includes tapered spray tip 210. Although not shown, a fluid direction component, such as a vacuum pump and/or an electrokinetic force modulator is typically operably connected to sample delivery device 200 via port 208. Various embodiments of fluid direction components that are optionally used in the devices of the invention are discussed in greater detail below. During operation, the fluid direction component typically draws aliquots of fluidic materials into capillary element 206 through tapered spray tip 210 from a sample source. Optionally, sample aliquots are further drawn into, e.g., microchannel 202 through capillary element 206. In certain embodiments, body structures are operably connected (e.g., integrally, removably, or the like) to plates with manifolds, which manifolds deliver fluidic materials to body structures that include, e.g., multiple ports in fluid communication with microscale cavities within the body structures. Fluid manifolding devices that are optionally adapted for use with the devices and methods of the invention are described in greater detail in, e.g., International Application No. PCT/JUS01/24324, entitled "METHODS AND DEVICES FOR HIGH THROUGHPUT FLUID DELIVERY," filed Aug. 2, 2001 by Chow et al., which is incorporated by reference in its entirety for all purposes. Thereafter, the fluid direction component is typically used to spray or otherwise expel at least a portion of the sample aliquot from, e.g., tapered spray tip 210 at, or at least proximal to, a sample destination, such as an inlet orifice to a mass spectrometer.

A channel disposed through the capillary element typically includes a cross-sectional dimension (e.g., an inner diameter of the capillary element, etc.) of between about 1 μm and about 200 μm, more typically between about 1 μm and about 100 μm, and even more typically between about 1 μm and about 50 μm. In preferred embodiments, the channel disposed proximal (e.g., through) to the tapered spray tip includes a cross-sectional dimension that is typically between about 1 μm and about 10 μm and more typically between about 2 μm and about 8 μm, or e.g., about 5 μm. In addition, depending on the cross-sectional dimension of the channel within the capillary element, an outer cross-sectional dimension of the capillary element is typically between about 200 μm and about 500 μm, more typically between about 250 μm and about 450 μm, still more typically between about 300 μm and about 400 μm, or e.g., about 360 μm. Furthermore, capillary elements and channels disposed through capillary elements generally include cross-sectional shapes independently selected from, e.g., regular n-sided polygons, irregular n-sided polygons, triangles, squares, rectangles, trapezoids, circles, ovals, or the like.

Figure 4:
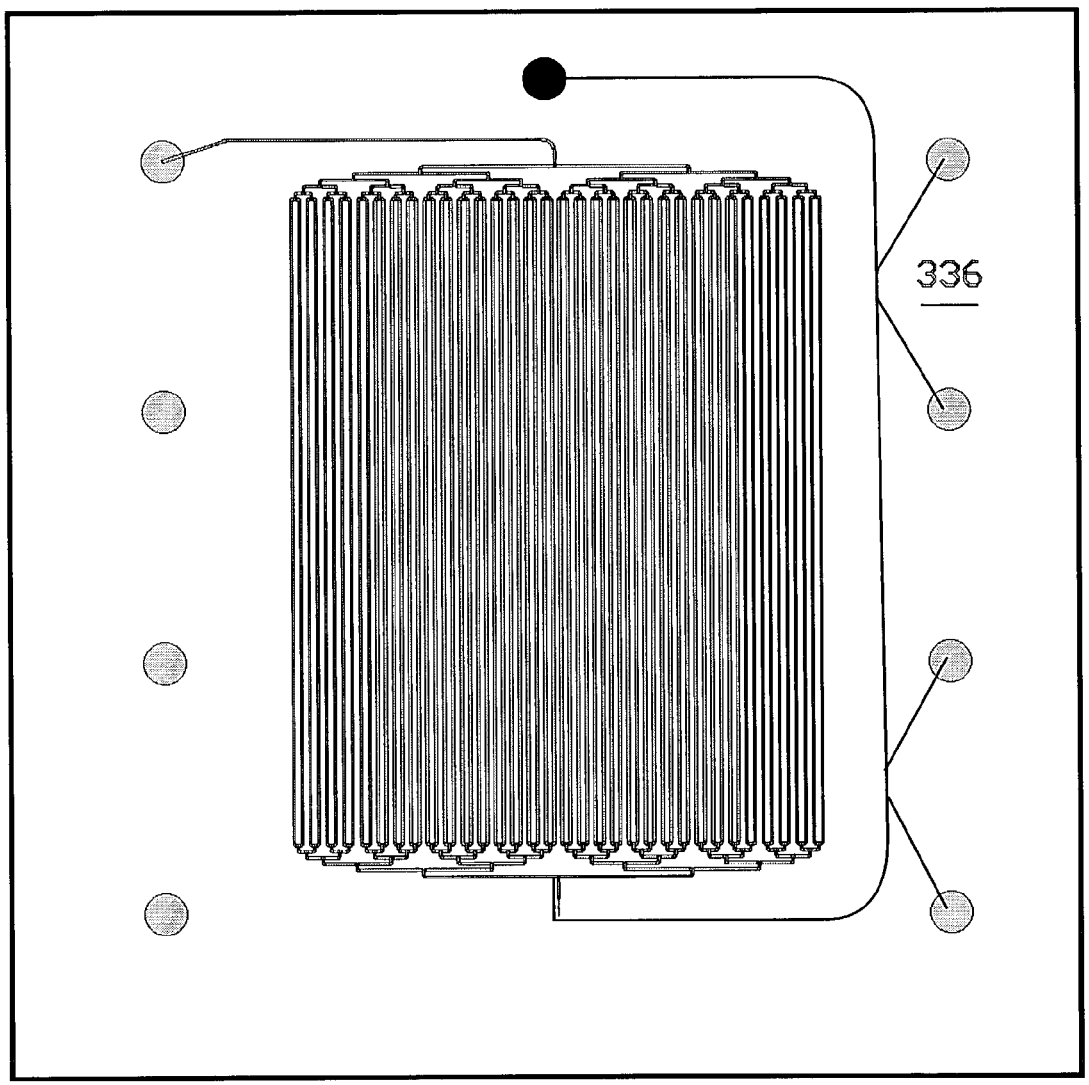
FIG. 4 schematically depicts a top view of another embodiment of an infusion device that includes multiple parallel microscale cavities fabricated in the device.

The fluid direction component optionally includes, e.g., a fluid pressure force modulator (e.g., a vacuum pumping system, etc.), an electrokinetic force modulator, both modulators, and/or other fluid direction components. For example, the fluid direction component is typically capable of spraying the selected aliquots from the tapered spray tip at a rate of between about 25 nl/minute and about 500 nl/minute, more typically at a rate of between about 35 nl/minute and about 250 nl/minute, and still more typically at a rate of between about 50 nl/minute and about 150 nl/minute. In certain embodiments, the microscale cavities include one or more virtual valves that do not include mechanical or moving parts, which virtual valves selectively regulate fluid flow in the one or more microscale cavities. Virtual valves are described further in, e.g., U.S. Pat. No. 5,842,787, entitled "MICROFLUIDIC SYSTEMS INCORPORATING VARIED CHANNEL DIMENSIONS," which issued Dec. 1, 1998 to Kopf-Sill et al., which is incorporated by reference in its entirety for all purposes. A microchannel configuration that is optionally used to provide virtual valves is schematically illustrated in FIG. 4, which is described further below. As mentioned above, in preferred embodiments, the fluid direction component is capable of spraying the selected aliquots substantially orthogonally from the tapered spray tip to the sample destination. An example system for orthogonally electrospraying samples at orifices of mass spectrometers is provided below. In some embodiments, fluid direction components include a fluid pressure force modulator that is capable of applying pressure to draw the selected aliquots, e.g., at least into the capillary element. In these embodiments, fluid direction components typically further include an electrokinetic force modulator that is capable of applying a potential gradient along a length of microscale cavities disposed within body structures and/or capillary elements to spray (e.g., electrospray, etc.) selected aliquots from tapered spray tips proximal to sample destinations. For example, at least a segment of a microscale cavity and/or a tapered spray tip optionally includes a conductive coating operably connected to a power source to produce a potential gradient in the segment. In preferred embodiments, devices of the invention further include an electrical control system operably connected to tapered spray tips and the sample destination, which electrical control system is capable of generating a potential difference between the tapered spray tip and the sample destination to electrospray the selected aliquots from the tapered spray tip proximal to the sample destination. The devices also typically include at least one automated controller operably connected to one or more of the body structure, the fluid direction component, and/or another device component (e.g., a device handling system, etc.) to direct operation of the device.

Figure 3:
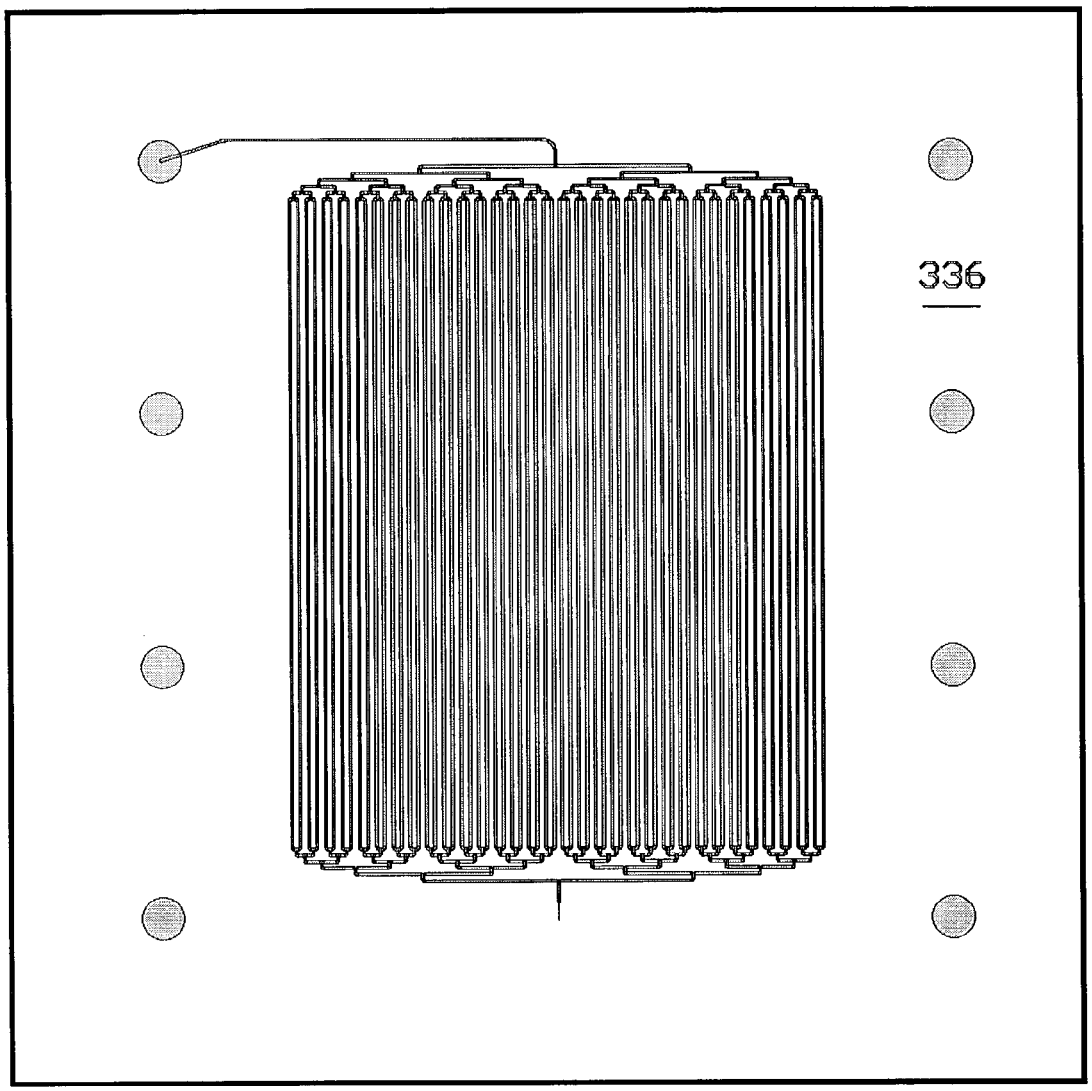
FIG. 3 schematically depicts a top view of one embodiment of an infusion device that includes multiple parallel microscale cavities fabricated in the device.

As an additional option, microscale cavities of device body structures include fluidic materials that are capable of being flowed out of the capillary element to wash a channel disposed through the capillary element, e.g., after a sample aliquot is sprayed from the device. As another option, microscale cavities include fluidic sample materials that are capable of being sprayed from the tapered spray tip proximal to the sample destination. In some embodiments, the microscale cavities include a plurality of parallel microscale cavities. In these embodiments, the plurality of parallel microscale cavities typically includes a volume capacity of between about 1 μl and about 10 μl. To illustrate, FIG. 3 schematically depicts a top view of an infusion device that includes a plurality of parallel microchannels. The sample storage capacity of the parallel microchannels in the depicted device is about 4 μl. Although not viewable in FIG. 3, the device includes a single capillary element extending from the body structure that includes a spray tip having a channel with a cross-sectional dimension (i.e., an inner diameter of the capillary element proximal to the spray tip) of about 20 μm. Under an applied pressure of about −5 psi, it takes about 15 minutes to draw a fluidic sample through the capillary element to fill the parallel microchannels. Further, at a continuous flow rate of about 100 nl/minute, it takes about 40 minutes to spray the fluidic sample from a device filled to capacity. As another example, FIG. 4 schematically illustrates a top view of an additional infusion device that includes multiple parallel microchannels. Although not viewable, this device includes two capillary elements extending from the body structure. One capillary element (e.g., a sipper capillary, etc.) is optionally used to draw fluidic materials into the parallel microchannels of the device, while the other capillary element (e.g., a spray capillary, etc.) is optionally used to spray fluidic materials from the device. The sipper capillary of the device schematically depicted in FIG. 4 includes a channel disposed through the capillary that has a diameter of about 50 μm, such that under an applied pressure of about −5 psi, it takes about 1 minute to fill the device. The channel disposed through the spray capillary has a diameter of about 15 μm. To regulate fluid flow, the device schematically shown in FIG. 4 also includes a channel configuration that is optionally used to provide two counter flow virtual valves.

In certain embodiments, a sample delivery device of the invention includes a plurality of capillary elements extending from the body structure in which at least one member of the plurality fluidly communicates with the one or more microscale cavities. In preferred embodiments, each capillary element fluidly communicates with a microscale cavity within the body structure. To illustrate, the plurality of capillary elements optionally include first and second capillary elements, which second capillary element includes the tapered spray tip. In these embodiments, sample aliquots are generally capable of being drawn into the body structure from the sample source through the first capillary element and sprayed from the tapered spray tip of the second capillary element proximal to the sample destination. Typically, a first channel disposed through the first capillary element includes a larger cross-sectional dimension than a second channel disposed through the second capillary element. In preferred embodiments, the fluid direction component is capable of drawing the selected aliquots into the body structure at a higher flow rate than the selected aliquots are sprayed from the tapered spray tip. For example, such as device is discussed above with respect to FIG. 4. In some embodiments, a microscale cavity (e.g., a microchannel or the like) disposed between the first and second capillary elements within the body structure includes a separation region in which at least one component of, e.g., a selected aliquot of a given sample is capable of being separated from other components prior to being sprayed from the tapered tip proximal to the sample destination. In one of these embodiments, for example, the separation region includes a chromatographic material to separate the components. In other embodiments, the separation region includes electrodes disposed therein, which electrodes are operably connected to an electrical control system to electrophoretically separate the components in the separation region. Sample component separations and other upstream processes are described in greater detail below.

A microfluidic sample delivery device of the invention also typically further includes a device handling system operably connected to the device. Device handling systems are generally capable of selectively moving the device, or a portion the device (e.g., a flexible capillary element extending from the device), relative to the sample source and the sample destination. For example, the device handling system is typically capable of translocating or rotating the device between the sample source and the sample destination. In certain embodiments, the device handling system is capable of rotating the device about 90° between the sample source and the sample destination. In other embodiments, the capillary element is flexible and the device handling system includes a capillary element flexing component operably connected to the capillary element. The capillary element flexing component is typically capable of selectively flexing the tapered spray tip of the capillary element between the sample source and the sample destination. For example, the capillary element flexing component is typically capable of flexing the tapered spray tip about 90° between the sample source and the sample destination.

The invention further includes a method of spraying a fluidic sample proximal to a sample destination. In particular, the method includes providing a microfluidic device that includes a capillary element extending from a body structure of the device that fluidly communicates with microscale cavities disposed within the body structure, which capillary element includes a tapered spray tip (e.g., a nozzle, etc.). The method further includes drawing a selected aliquot of a fluidic sample from a sample source (e.g., a microwell plate or the like) into at least the capillary element. Thereafter, the method includes spraying the selected aliquot from the tapered spray tip proximal to the sample destination (e.g., an inlet to a detection device, such as a mass spectrometer). The method also typically includes detecting a detectable signal produced by at least one component of the selected aliquot. The drawing and spraying steps are typically performed using a fluid direction component/system (e.g., a fluid pressure force modulator and/or an electrokinetic force modulator, etc.) operably connected to the body structure. In some embodiments, the selected aliquot is drawn only into the capillary element, whereas in others the selected aliquot is drawn through the capillary element and into the body structure. Advantages of drawing selected aliquots only into capillary elements include avoiding, e.g., potential contamination from glue and/or the effects of dead volumes at joints between capillary elements and body structures, which can bias results upon assay detection. In any event, selected aliquots are typically drawn into the body structure (or into capillary elements alone) at a higher flow rate than the aliquots are sprayed from tapered spray tips, e.g., to further provide suitable resolution of assay components in resulting mass spectra. Typical fluid flow rates are described herein.

B. Embodiments Involving Spraying from Device Edges

One embodiment of a microfluidic device/mass spectrometer interface of the invention includes a microfluidic device that draws or sips samples from an external source, such as from a well in a microwell plate, into the device and sprays (e.g., nanoelectrosprays, etc.) the sample into the orifice of a mass spectrometer detector. These embodiments generally combine the planar patterning and etch technology used to fabricate, e.g., sipper LabChips® (Caliper Technologies Corp., Mountain View, Calif.) with process for fabricating electrospray nozzles to create an array of sipper capillary elements and spray nozzles for a microfluidic device to mass spectrometer interface. The capillary elements and spray nozzles can be in the same plane as the body of the microfluidic device, or can be in a different plane than the device (e.g., perpendicular or orthogonal to the body of the device). In certain embodiments, nozzles, or nozzle plates that include arrays of nozzles, are fabricated from silicon and bonded to planar microfluidic devices having one or more microchannels with openings on device surfaces, e.g., on distal ends of the devices. Arrays of nozzles that are optionally adapted for use with the devices of the present invention are described in, e.g., Schultz et al. (2000) "A Fully Integrated Monolithic Microchip Electrospray Device for Mass Spectrometry," *Anal. Chem.* 72:4058-4063. Optionally, fluidic materials (e.g., fluidic sample materials, fluidic wash materials, etc.) are stored in device cavities prior to being sprayed or otherwise expelled from the device. An additional option includes separating components, e.g., components within a sample aliquot, in the device prior to spraying those components into the mass spectrometer orifice. Essentially any other microfluidic assay is also optionally performed prior to delivering a sample to a mass spectrometer orifice. These devices provide reliable and multiple use electrospray orifices, e.g., including spray nozzles with inner diameters in the range of about 4 µm to about 10 µm that are typically bonded to low cost planar glass microfluidic body structures.

In particular, these embodiments of the invention relate to a sample delivery device that includes (a) a microfluidic device that includes (i) a body structure (e.g., fabricated from glass, quartz, etc.) that includes one or more microscale cavities disposed therein, (ii) at least one capillary element (e.g., fabricated from plastic, glass, quartz, metal, and/or other materials) extending from the body structure that fluidly communicates with the one or more microscale cavities, which capillary element draws selected aliquots of at least one fluidic sample from a sample source (e.g., a microwell plate, etc.) into the body structure, and (iii) a nozzle plate (e.g., fabricated from silicon, etc.) that includes at least one nozzle fabricated therein, which nozzle fluidly communicates with the one or more microscale cavities and delivers (e.g., electrosprays, etc.) the selected aliquots to a sample destination (e.g., an inlet to a detection device, such as a mass spectrometer or the like). In preferred embodiments, channels disposed through sipper capillary elements include larger cross-sectional dimensions than the nozzles. The sample delivery device also includes (b) at least one fluid direction component which flows the selected aliquots through the device from the sample source to the sample destination. The fluid direction component optionally includes a fluid pressure force modulator and/or an electrokinetic force modulator, or other fluid direction components. To illustrate, the fluid direction component optionally includes a fluid pressure force modulator which applies pressure to draw the selected aliquots into the device through the capillary element and to flow the selected aliquots through the device. In certain embodiments, for example, the fluid direction component further includes an electrokinetic force modulator which applies a potential gradient along a length of the one or more microscale cavities and/or the nozzle to electrospray the selected aliquots from the nozzle at the sample destination. For example, at least a portion of at least one of the one or more microscale cavities and the nozzle optionally includes a conductive coating operably connected to a power source to produce a potential gradient in the portion. It will be appreciated by persons skilled in the art to which this invention pertains that the number and/or configuration of sipper capillary elements, nozzles, and/or microchannels are optionally varied. Additional options include varying properties (e.g., physical properties, chemical properties, etc.) of the nozzles and/or nozzle plates. Furthermore, the device also typically further includes an automated controller (e.g., a device handling system, etc.) operably connected to the device to move the device relative to the sample source and the sample destination.

In some embodiments, the microscale cavities include a plurality of parallel microscale cavities. In certain embodiments, the microscale cavities include a plurality of aligned microscale cavities in which at least two members of the plurality are spaced at different distances from one another along a length of an alignment. In these embodiments, the nozzle plate typically includes an array of nozzles in which at least two members of the array fluidly communicate with different microscale cavities.

Figure 5A:
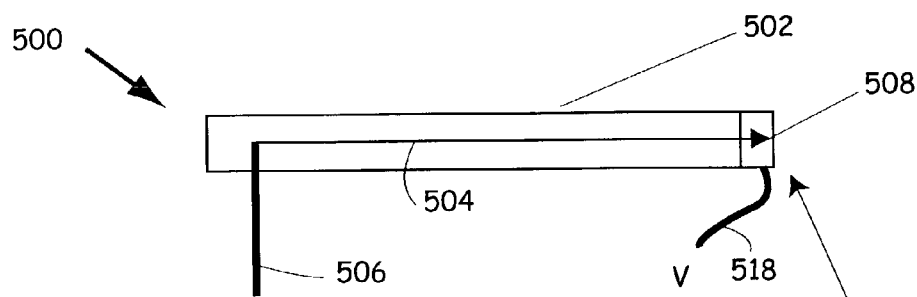
FIG. 5A schematically illustrates a side view of a sample delivery device according to one embodiment of the invention.
Figure 5B:
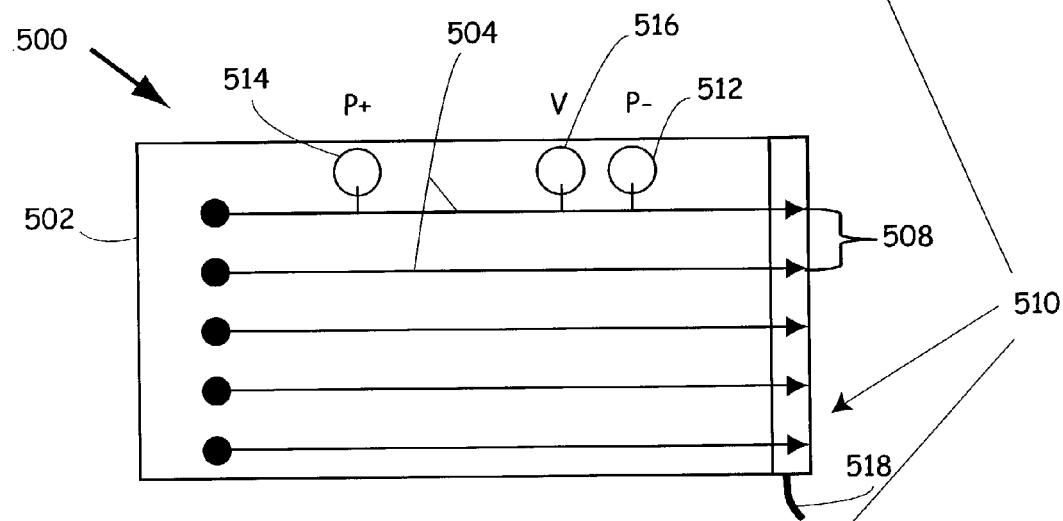
FIG. 5B schematically depicts a top view of the sample delivery device schematically shown in FIG. 5A.
Figure 5C:
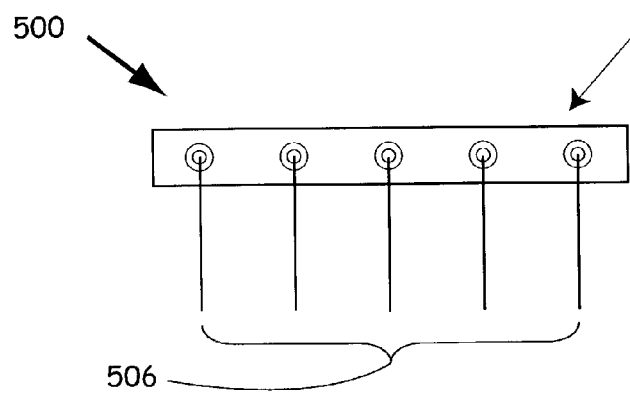
FIG. 5C schematically shows the sample delivery device schematically depicted in FIG. 5A from another side view.

FIG. 5A schematically illustrates a side view of a sample delivery device according to one embodiment of the invention. As shown, sample delivery device 500 includes body structure 502 which includes microchannels 504 (only one is within view in FIG. 5A) that fluidly communicate with sipper capillary elements 506 (only one is within view in FIG. 5A) and with nozzles 508 (e.g., an array of nozzles, etc.)(only one is within view in FIG. 5A) disposed in nozzle plate 510. In one device configuration, one sipper capillary fluidly communicates with one microchannel disposed within a body structure and with one spray nozzle. FIG. 5B schematically depicts a top view of the sample delivery device schematically shown in FIG. 5A. As shown, sample delivery device 500 includes multiple microchannels 504 and multiple nozzles 508. As further shown, sample delivery device 500 includes connection points (512, 514, 516, and 518) for various fluid direction components. For purposes of clarity of illustration, only one set of such fluid direction component connection points is shown for one microchannel 504. In particular, one or more pressure force modulators are typically operably connected to, e.g., connection point 512 (e.g., a port) to apply a vacuum or negative pressure (P−) to draw or sip fluidic materials into microchannel 504 and to, e.g., connection point 514 to apply positive pressure (P+) to spray sample aliquots out of nozzle 508. One or more electrokinetic force modulators are also typically operably connected to, e.g., connection points 516 and 518 to apply a voltage that biases channel contents to be sprayed by electrospray. As mentioned above, sample component separations are also optionally performed in the devices of the invention, e.g., prior to being sprayed at sample destinations, with, e.g., electrical connections that are generally known in the art, e.g., to effect electrophoretic separations. Sample component separations and other upstream processes are described further below. FIG. 5C schematically shows the sample delivery device schematically depicted in FIG. 5A from another side view. As further shown, sample delivery device 500 includes multiple sipper capillary elements 506. During sipping or drawing steps, care should be taken to avoid emptying the spray nozzles, e.g., by applying a counter pressure proximal to the spray nozzles, by varying channel dimensions, and/or the like. Similarly, during spraying steps, care should be exercised to avoid emitting fluidic materials from sipper capillary elements. Devices such as those depicted in, e.g., FIGS. 5A-C typically further include a microfluidic device handling system operably connected to body structures to move devices, e.g., to align individual nozzles with mass spectrometer orifices.

Figure 6:
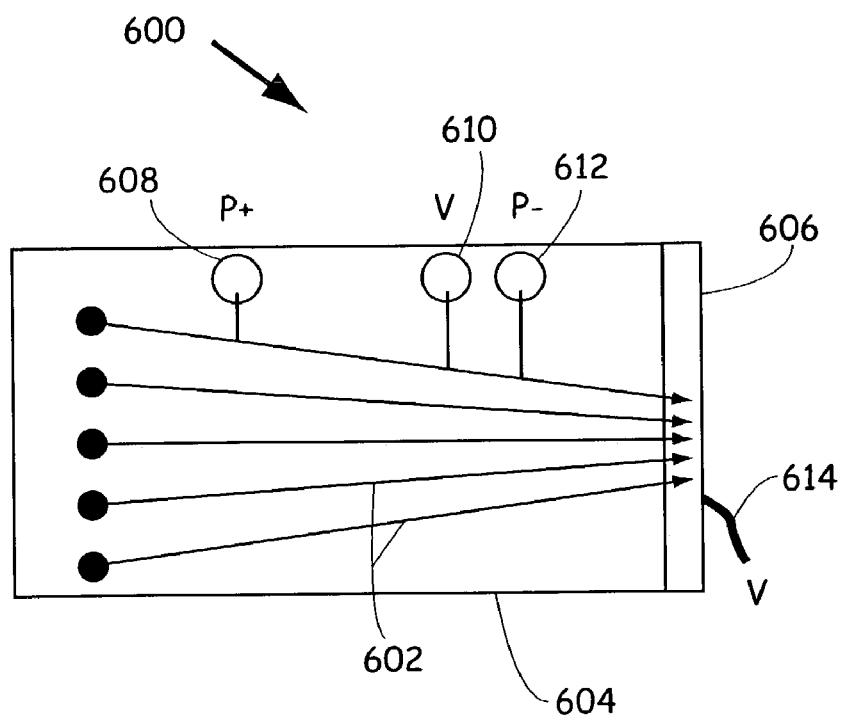
FIG. 6 schematically depicts a top view of a sample delivery device having a clustered array of nozzles according to one embodiment of the invention.
Figure 7:
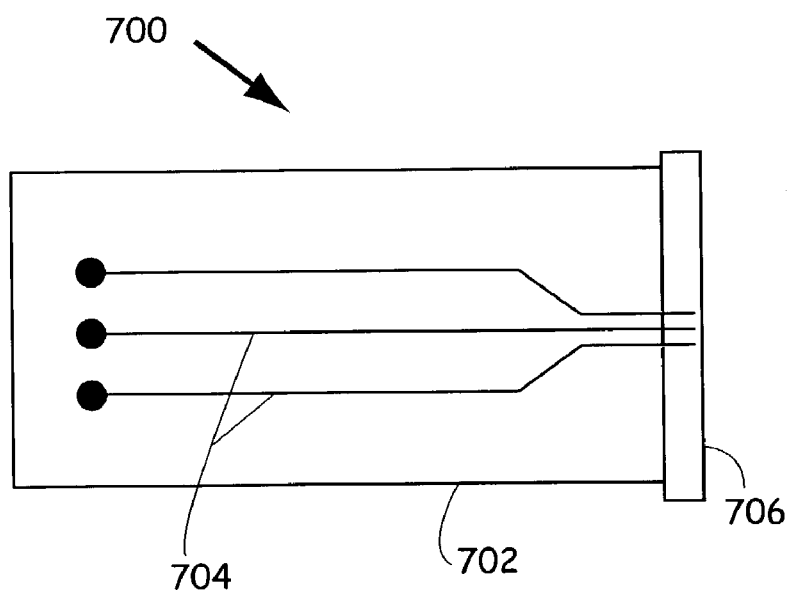
FIG. 7 schematically illustrates a top view of a sample delivery device having a clustered array of nozzles according to another embodiment of the invention.

In certain embodiments, nozzles arrayed in a nozzle plate are clustered close enough together to avoid having to realign individual nozzles with mass spectrometer orifices, e.g., to further enhance device throughput. For example, in certain embodiments, members of the array are optionally disposed relative to one another such that the selected aliquots are capable of being delivered simultaneously from at least two nozzles to the sample destination. To illustrate, FIG. 6 schematically depicts a top view of a sample delivery device having a clustered array of nozzles according to one embodiment of the invention. As shown, microchannels 602 of sample delivery device 600 are disposed in closer proximity to each other towards the side of body structure 604 to which nozzle plate 606 is bonded than in other regions of body structure 604. As further shown, sample delivery device 600 includes connection points (608, 610, 612, and 614) for various fluid direction components. For purposes of clarity, only one set of such fluid direction component connection points is shown for one microchannel 602. To further illustrate, FIG. 7 schematically illustrates a top view of a sample delivery device having a clustered array of nozzles according to another embodiment of the invention. As shown, body structure 702 of sample delivery device 700 includes two different regions in which microchannels 704 are disposed substantially parallel to each other. In such a region proximal to nozzle plate 706, microchannels 704 are in closer proximity to each other than in the other such region to facilitate sample spraying at a mass spectrometer orifice, e.g., in the absence of individual nozzle realignment. These embodiments also typically include handling systems operably connected to device body structures to effect movement of device relative to, e.g., sample sources and sample destinations.

In preferred embodiments, thermal expansion coefficients of the body structure and the nozzle plate are approximately equal, e.g., to facilitate anodic bonding of these components to one another during device fabrication/assembly. Anoding bonding typically includes bonding two clean, polished surfaces that have approximately equal thermal expansion coefficients. For example, to match a silicon nozzle plate that includes an array of nozzles, a body structure is typically fabricated from a substrate material that includes a thermal expansion coefficient of about 20 ppm/° C. Among other things, silicon is a preferred substrate from which to fabricate nozzle plates, because arrays of nozzles are typically readily fabricated with uniformity using known techniques. In preferred embodiments, Pyrex® glass is used to match the thermal expansion coefficient of a silicon nozzle plate. Quartz substrates are typically avoided when body structures are to be bonded to a silicon nozzle plate, because they have thermal expansion coefficients of only about 0.55 ppm/° C. Anodic bonding is generally preferred because it provides a hermetic or airtight seal without using any potentially contaminating adhesives. Optionally, other bonding techniques, including adhesives, are utilized. These techniques are described further below. Typically, at least a portion of a nozzle includes a cross-sectional dimension of between about 1 µm and about 200 µm, more typically between about 1 µm and about 100 µm, and still more typically between about 1 µm and about 50 µm (e.g., about 2 µm, about 3 µm, about 4 µm, about 5 µm, about 6 µm, about 7 µm, about 8 µm, about 9 µm, about 10 µm, etc.). Each nozzle generally includes two termini that include different cross-sectional dimensions. In preferred embodiments, the nozzle includes a cross-sectional dimension that produces a surface tension on fluidic materials disposed therein sufficient to prevent voiding the fluidic materials from the nozzle, e.g., when pressure is applied to the capillary element.

Optionally, a sample delivery device according to these embodiments includes a plurality of capillary elements extending therefrom in which at least one member of the plurality fluidly communicates with the one or more microscale cavities. Typically, all members of the plurality of capillary elements fluidly communicate with microscale cavities, such as microchannels or the like. See, e.g., FIG. 6C, which is described above. In some embodiments, at least one of the microscale cavities includes a fluidic material to wash at least one of the capillary element and the nozzle, e.g., after a sample is drawn into or sprayed from the device, respectively. Device washing and other downstream steps are described in greater detail below. In certain embodiments, at least one of the microscale cavities includes a chromatographic material to separate at least one component of the selected aliquots from other components prior to flowing the selected aliquots to the sample destination. In other embodiments, at least one of the microscale cavities further includes electrodes disposed therein, which electrodes are operably connected to a power source to electrophoretically separate at least one component of the selected aliquots from other components prior to flowing the selected aliquots to the sample destination.

The invention also provides a method of delivering a fluidic sample to a sample destination. The method includes (a) providing a microfluidic device that includes (i) a body structure that includes one or more microscale cavities disposed therein, (ii) at least one capillary element extending from the body structure, which capillary element fluidly communicates with the one or more microscale cavities, and (iii) a nozzle plate that includes at least one nozzle fabricated therein, which nozzle fluidly communicates with the one or more microscale cavities. The method also includes (b) drawing at least one selected aliquot of the fluidic sample from a sample source (e.g., a microwell plate, etc.) into the body structure through the capillary element, and (c) expelling (e.g., electrospraying, etc.) the selected aliquot of the fluidic sample from the nozzle at the sample destination (e.g., an inlet to a mass spectrometer, etc.). In some embodiments, (b) further includes drawing a buffer into at least a portion of the body structure through the capillary element to prime the body structure prior to drawing the selected aliquot. In certain embodiments, (b) and (c) include using a pressure force modulator to draw and expel the selected aliquot. A fluid flow rate is typically faster in (b) than in (c). In preferred embodiments, (c) includes electrospraying the selected aliquot from the nozzle. For example, optionally (b) includes drawing the selected aliquot using a pressure force modulator and (c) includes expelling the selected aliquot using an electrokinetic force modulator.

The methods optionally further include separating at least one component of the selected aliquot from other components prior to expelling the selected aliquot from the nozzle. In some embodiments, the body structure includes a plurality of capillary elements extending therefrom in which at least one member of the plurality fluidly communicates with the one or more microscale cavities. Optionally, (b) includes using at least two members of the plurality sequentially or simultaneously. In some embodiments, the nozzle plate includes a plurality of nozzles in which at least one member of the plurality fluidly communicates with the one or more microscale cavities. For example, (c) optionally includes using at least two members of the plurality sequentially or simultaneously. In some embodiments, the method further includes (d) washing at least one of the capillary element and the nozzle with at least one buffer solution. Optionally, (b)-(d) are repeated. In other embodiments, the methods further include (d) flowing one or more fluidic materials from at least one of the one or more microscale cavities to wash at least one of the capillary element and the nozzle. In these embodiments, (b)-(d) are repeated. In preferred embodiments, the methods include (e) detecting a detectable signal or property (e.g., a fluorescent signal, a mass, etc.) of at least one component of the expelled sample aliquot.

The present invention provides other devices, and methods involving such devices, in which samples are delivered to a sample destination from an edge of a device. In overview, these devices include glued or otherwise attached capillary elements to draw or sip fluidic samples, etched quartz channels disposed within body structures, e.g., for fluid transport and component separations, and at least one monolithic nozzle fabricated typically using a combination of dicing, grinding, and etching processes to provide a robust and low cost sample delivery device. As with other embodiments of the invention, this device addresses the need for a simple method to use a microfluidic device to deliver various sample aliquots to a sample destination in a high throughput and automated manner for high-resolution detection (e.g., using a mass spectrometer or other detection system).

In particular, the present invention provides a sample delivery device that includes (a) a microfluidic device that includes (i) a body structure (e.g., fabricated from glass, quartz, and/or another material) that includes one or more microscale cavities disposed therein, (ii) at least one capillary element (e.g., fabricated from plastic, glass, quartz, metal, and/or another material) extending from the body structure that fluidly communicates with the one or more microscale cavities, which capillary element draws selected aliquots of at least one fluidic sample from a sample source (e.g., a microwell plate or another type of fluid container), and (iii) at least one nozzle fabricated proximal to an edge of the body structure that includes at least a portion of the one or more microscale cavities, which nozzle delivers the selected aliquots of the fluidic sample to a sample destination. Typically, the portion of the one or more microscale cavities includes a cross-sectional dimension that produces a surface tension on fluidic materials disposed therein sufficient to prevent voiding the fluidic materials from the nozzle when pressure is applied to the capillary element. For example, the portion typically includes a cross-sectional dimension of between about 1 µm and about 200 µm. In preferred embodiments, a channel disposed through the capillary element includes a larger cross-sectional dimension than the nozzle. The device also includes (b) at least one fluid direction component which flows the selected aliquots through the device from the sample source to the sample destination (e.g., an inlet a detection device, such as a mass spectrometer or the like). In certain embodiments, at least one of the one or more microscale cavities includes a fluidic material to wash at least one of the capillary element and the nozzle, e.g., after a sample has been flowed through the device component. Optionally, at least a segment of at least one of the one or more microscale cavities and the nozzle includes a conductive coating operably connected to a power source to produce a potential gradient in the segment. In some embodiments, the fluid direction component includes a fluid pressure force modulator and/or an electrokinetic force modulator, or the like. For example, the fluid direction component optionally includes a fluid pressure force modulator which applies pressure to draw the selected aliquots into the device through the capillary element and to flow the selected aliquots through the device. In certain embodiments, the fluid direction component optionally further includes an electrokinetic force modulator which applies a potential gradient along a length of the one or more microscale cavities and the nozzle to electrospray the selected aliquots from the nozzle at the sample destination. Fluid direction components are described in greater detail below. In additional embodiments, the sample delivery device further includes an automated controller operably connected to the device to move the device relative to the sample source and the sample destination.

Figure 8A:
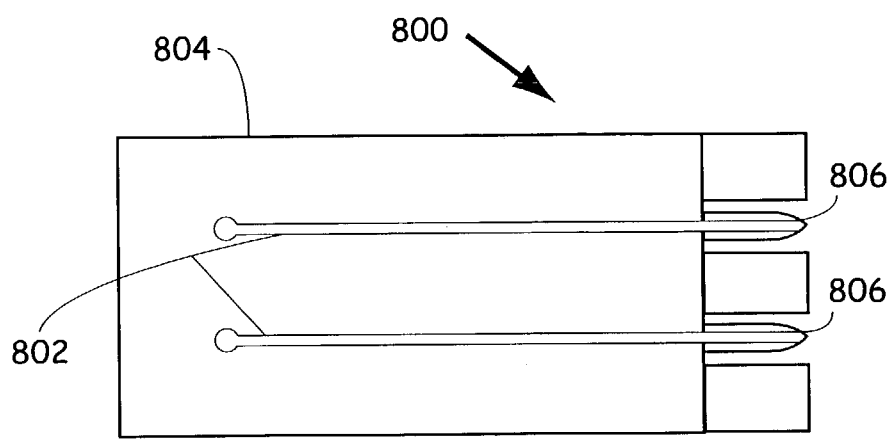
FIG. 8A schematically shows a top view of a microfluidic sample delivery device that includes two monolithic spray tips extending from an edge of the device.
Figure 8B:
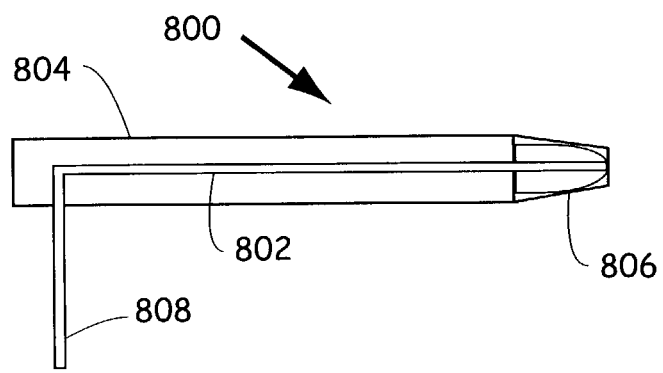
FIG. 8B schematically illustrates a side view of the device of FIG. 10A.
Figure 8C:
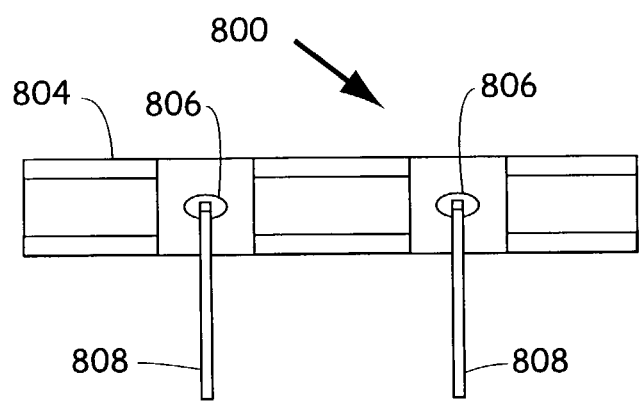
FIG. 8C schematically depicts another side view of the device of Figure A.

Optionally, the sample delivery device includes a plurality of capillary elements extending therefrom in which at least one member of the plurality fluidly communicates with a microscale cavity. Typically, each member of the plurality of capillary elements fluidly communicates with a microscale cavity. FIG. 8A schematically shows a top view of a microfluidic sample delivery device that includes two monolithic spray nozzles extending from an edge of the device in which each nozzle fluidly communicates with a separate capillary element that extends from the device. As shown, microfluidic sample delivery device 800 includes two microchannels 802 disposed within body structure 804. Microchannels 802 are disposed through sample spray nozzles 806. FIGS. 8B and C schematically illustrates two side views of the device of FIG. 8A. As further shown, sipper capillary elements 808 extend from body structure 804 and fluidly communicate with microchannels 802. Optionally, devices include only a single fabricated nozzle, whereas in others an array of nozzles is fabricated on a given device in which at least one member of the array fluidly communicates with the microscale cavities. See, also, e.g., FIGS. 5A-C, which are described above. For example, members of a nozzle array are optionally disposed relative to one another such that the selected aliquots are capable of being delivered simultaneously from at least two nozzles to the sample destination. In certain embodiments, the microscale cavities include a plurality of parallel microscale cavities. Typically, each nozzle in a given array fluidly communicates with a different microscale cavity. In some embodiments, the microscale cavities include a plurality of aligned microscale cavities in which at least two cavities are spaced at different distances from one another along a length of an alignment.

In certain embodiments of the monolithic spray tip devices, at least one microscale cavity includes a chromatographic material, e.g., to separate at least one component of the selected aliquots from other components prior to flowing the selected aliquots to the sample destination. For example, at least one microscale cavity optionally further includes electrodes disposed therein, which electrodes are operably connected to a power source to electrophoretically separate at least one component of the selected aliquots from other components prior to flowing the selected aliquots to the sample destination. Illustrations of upstream processes, such as sample component separations are described further below.

The present invention also provides methods of delivering a fluidic sample to a sample destination using, e.g., a device that includes a monolithic spray tip. The methods include (a) providing a microfluidic device that includes (i) a body structure that includes one or more microscale cavities disposed therein, (ii) at least one capillary element extending from the body structure, which capillary element fluidly communicates with the one or more microscale cavities, and (iii) at least one nozzle fabricated proximal to an edge of the body structure (e.g., at least one monolithic spray nozzle or tip) that includes at least a portion of the one or more microscale cavities. In addition, the methods include (b) drawing at least one selected aliquot of the fluidic sample from a sample source (e.g., a microwell plate, etc.) into the body structure through the capillary element, and (c) expelling the selected aliquot of the fluidic sample from the nozzle at the sample destination (e.g., an inlet to a mass spectrometer, etc.).

In certain embodiments of these methods, (b) further includes drawing a buffer into at least a segment of the body structure through the capillary element to prime the body structure prior to drawing the selected aliquot. In some embodiments, (b) includes using at least two members of the plurality sequentially or simultaneously. Typically, a fluid flow rate is faster in (b) than in (c). Optionally, (b) and (c) include using a pressure force modulator to draw and expel the selected aliquot. In preferred embodiments, (c) includes electrospraying the selected aliquot from the nozzle. In some embodiments, (b) includes drawing the selected aliquot using a pressure force modulator and (c) includes expelling the selected aliquot using an electrokinetic force modulator.

Optionally, the at least one nozzle includes a plurality of nozzles in which at least one member of the plurality fluidly communicates with the microscale cavities. For example, (c) optionally includes using at least two members of the plurality sequentially or simultaneously. In certain embodiments, the method further includes (d) washing at least one of the capillary element and the nozzle with at least one buffer solution. Optionally, (b)-(d) are repeated. In other embodiments, the method further includes (d) flowing one or more fluidic materials from at least one of the one or more microscale cavities to wash at least one of the capillary element and the nozzle, e.g., after a given sample aliquot is flowed through the device component. In these embodiments, (b)-(d) are also optionally repeated. As an additional option, (d) includes detecting a detectable signal produced by a component expelled or sprayed from a nozzle of the device. The methods optionally also include separating at least one component of the selected aliquot from other components prior to expelling the selected aliquot from the nozzle.

The monolithic spray tip is typically patterned with a combination of mechanical dicing, grinding, and etching processes to produce a spray tip with a tapered outer cross-sectional dimension (e.g., an outer diameter, etc.). Various parameters are optionally varied, such as the channel geometries that define the inner cross-sectional dimension (e.g., an inner diameter, etc.), the geometries that define the outer cross-sectional dimension of the spray tip, the protruding length of the spray tip from an edge of a body structure, physical and/or chemical properties of substrates materials (e.g., the hydrophilic nature of the tip produced through etching), the number of spray tips and/or capillary elements, and/or the like.

Figure 9D:
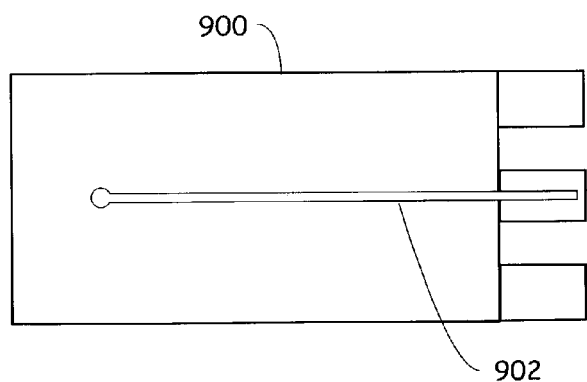
Figure 9E:
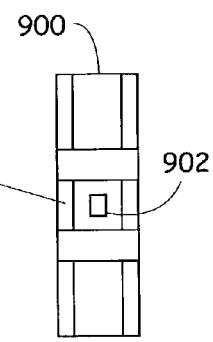
Figure 9F:
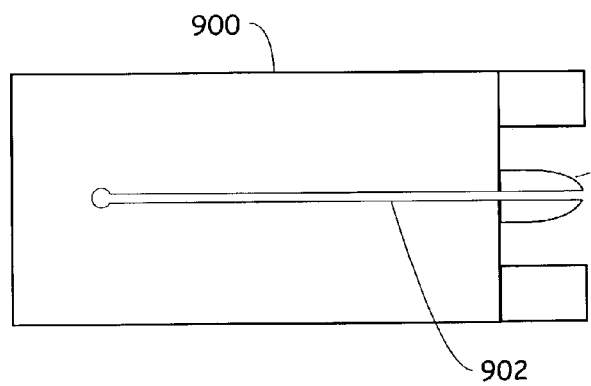
Figure 9G:
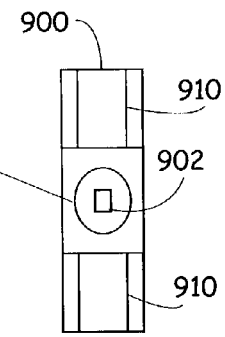
Figure 10A:
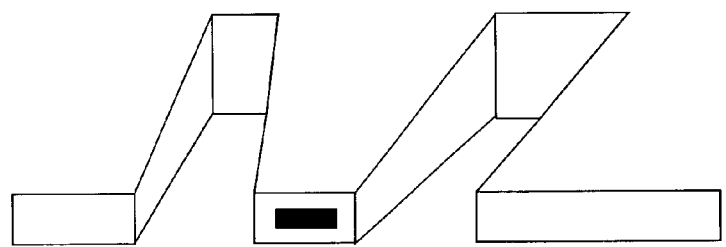
FIG. 10A schematically illustrates a gross monolithic spray nozzle after chamfering and excision.
Figure 10B:
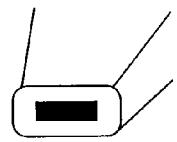
FIG. 10B schematically illustrates the monolithic spray nozzle of FIG. 14A after isotropic etching.

In illustrate, the invention provides methods of fabricating a microfluidic sample delivery device. The methods include (a) providing a body structure (e.g., a glass, quartz, or other material) that includes at least one microscale cavity fabricated therein in which at least one portion of the at least one microscale cavity terminates prior to and proximal to a edge of the body structure. For example, a microscale channel, such as a microchannel is optionally etched into a surface of a first substrate, which surface is then bonded to a surface of a second substrate to form the microchannel within bonded substrates, which form the body structure. Microfluidic fabrication techniques that are optionally used or adapted for use in manufacturing the devices of the present invention are described in greater detail below. To further illustrate these fabrication methods, FIG. 9A schematically shows microchannel 902 disposed in body structure 900. FIG. 9B schematically shows body structure 900 of FIG. 9A from a side view. Optionally, the methods include beveling or chamfering an edge of body structure 900 using, e.g., grinding wheel 904. (FIG. 9C). In preferred embodiments, the edge of the chip is ground with about 10° bevel to taper nozzle tip edge 906 out of a plane of body structure 900. The method further includes (b) excising one or more regions of the body structure proximal to the portion of the at least one microscale cavity to provide at least one gross nozzle structure. This is illustrated in FIG. 9D, which schematically depicts body structure 900 of FIG. 9C after segments have been excised or diced from an edge of body structure 900 to define the gross structure of monolithic spray nozzle 908. That is, segments of nozzle tip edge 906 have been excised from two sides of monolithic spray nozzle 908. FIG. 9E schematically shows body structure 900 of FIG. 9D from a side view. FIG. 10A also schematically illustrates a gross monolithic spray nozzle after chamfering and excision. The methods also include (c) etching the at least one gross nozzle structure such that the portion of the at least one microscale cavity is exposed on the edge of the body structure to produce at least one monolithic nozzle. This is illustrated in FIG. 9F, which schematically depicts body structure 900 of FIG. 9D after monolithic spray nozzle 908 has been isotropically etched. FIG. 9G schematically illustrates body structure 900 of FIG. 9F from a side view. To further illustrate, FIG. 10B schematically illustrates the monolithic spray nozzle of FIG. 10A after isotropic etching, which, e.g., rounded the corners of the gross monolithic spray nozzle and opened the microchannel disposed within the body structure. In particular, the isotropic etch typically determines the final geometry of a spray nozzle, e.g., by rounding the nozzle. The gross nozzle dimensions are typically selected such that when the etch reaches the end of the microscale cavity to open the tip, the desired geometry is produced. If a body structure includes, e.g., an optical detection window or portion, that portion is typically protected during the etching process to prevent the etchant from damaging that portion. This technique produces a monolithic tip that is also protected by the surrounding shield material (e.g., remnants of nozzle tip edge 906). See, e.g., nozzle protection portions 910 in FIG. 9G. Further, this process produces monolithic electrospray tips that include proper dimensions for nano-electrospray, and are further compatible with separation techniques. Current isotropic etching technology and minimum lithographic line widths permit fabrication of channels that are, e.g., about 5 µm deep with a width of about 15 µm. After nozzle fabrication, one or more capillaries are typically bonded (e.g., glued or otherwise adhered) to a body structure for fluid communication with microscale cavities disposed within the body structure. For clarity, connections, e.g., for pressure and voltage are not shown. However, these connections are described herein or are generally known in the art.

Typically, the body structure includes one or more ports that fluidly communicate with the at least one microscale cavity and the methods further include (d) bonding at least one capillary element having a channel disposed therethrough in a port such that the capillary element fluidly communicates with the at least one microscale cavity. Optionally, the body structure includes at least two microscale cavities fabricated therein in which at least one portion of each microscale cavity terminates prior to and proximal to a edge of the body structure and the method includes fabricating at least two monolithic nozzles therefrom. Typically, the portion of the microscale cavity exposed on the edge of the body structure includes at least one cross-sectional dimension of between about 1 µm and about 200 µm. Optionally, before or after (b) the methods further include grinding at least one surface of the body structure proximal to the portion of the microscale cavity to chamfer a tip of the gross nozzle out of a plane of the at least one surface of the body structure. For example, (b) optionally includes grinding the at least one surface with about a 100 bevel. In certain embodiments, (c) includes isotropically etching the gross nozzle to provide a rounded nozzle. For example, the methods optionally include isotropically etching the gross nozzle with hydrofluoric acid.

C. Embodiments Involving Non-Linear Spray Capillaries

The invention also provides microfluidic devices that include non-linear capillary elements and related methods for sipping fluidic materials from fluid containers, storing the fluids in devices, and spraying the fluids into orifices of mass spectrometer detectors using, e.g., nanoelectrospray. Optionally, sample components are separated from each other, e.g., in the devices, or even prior to being flowed into the devices, before being sprayed into mass spectrometer orifices. The methods described herein use, e.g., current etched quartz and glued capillary element technology to provide a robust and low cost device-mass spectrometer interface. As with other embodiments of the invention, these embodiments address a need for a simple method to use a mass spectrometer detector for high-resolution detection of various sample components in a high-throughput and automated manner. In general, these embodiments include using devices (e.g., sip and spray devices) that include at least two capillary elements extending from a device body structure in which at least one sipper capillary element is typically used for sipping or drawing fluidic samples into the devices and in which at one spray capillary element is typically used for spraying samples from the devices.

In particular, the invention provides a sample delivery device that includes (a) a microfluidic device that includes (i) a body structure that includes one or more microscale cavities disposed therein, (ii) at least one linear capillary element extending from the body structure that fluidly communicates with the one or more microscale cavities, which linear capillary element draws selected aliquots of at least one fluidic sample from a sample source (e.g., a microwell plate, etc.) into the body structure, (iii) at least one non-linear capillary element extending from the body structure that fluidly communicates with the one or more microscale cavities, which non-linear capillary element delivers the selected aliquots to a sample destination, and (iv) a support structure or caddy connected to the body structure and to at least a segment of the non-linear capillary element to provide mechanical support to, and to constrain, the non-linear capillary element. Optionally, fluidic materials are drawn into devices through non-linear capillary elements and sprayed from the devices through linear capillary elements (e.g., orthogonally sprayed, sprayed following device rotation, etc.).

A non-linear capillary element typically includes a tapered spray tip or nozzle that includes a channel having a cross-sectional dimension (e.g., an inner diameter, etc.) of between about 1 µm and about 25 µm, or more typically between about 5 µm and about 20 µm, e.g., to properly nanoelectrospray samples from the non-linear capillary element. Spray tips also typically include hydrophobic surfaces (e.g., coated with a hydrophobic coating, such as polyimide or the like, e.g., to prevent spreading of aqueous materials) to ensure proper electrospraying. In addition, capillary elements (e.g., fused silica, quartz, polyimide capillary elements, etc.) typically have outer cross-sectional dimensions (e.g., outer diameters, etc.) between about 200 µm and about 500 µm, and more typically between about 300 µm and about 400 µm (e.g., about 360 µm). The sample delivery device also includes (b) at least one fluid direction component which flows the selected aliquots through the device from the sample source to the sample destination (e.g., an inlet to a detection device, such as a mass spectrometer, or the like). The fluid direction component typically includes a fluid pressure force modulator which applies pressure to draw the selected aliquots into the device through the linear capillary element and to flow the selected aliquots through the device. Optionally, the at least one fluid direction component further includes an electrokinetic force modulator which applies a potential gradient along a length of the non-linear capillary element to electrospray the selected aliquots from a nozzle disposed proximal to a terminus of the non-linear capillary element at the sample destination. Fluid direction components and connections to the devices of the invention are described further below.

The components of these devices are optionally varied. For example, the size, length, and/or tip geometry of capillary elements is optionally varied, as is the number of sip and/or spray capillary elements included in a particular device. These embodiments are typically used to sip and spray samples from devices, but are optionally extended to include other important upstream processes, such as sample component separations, e.g., with the addition of reservoirs for establishing electrical contact. Upstream processes are described in greater detail below. These embodiments primarily relate to non-linear spray capillary elements (e.g., extending from a device body structure surface that is oriented substantially perpendicular to a mass spectrometer orifice during operation), but are optionally extended to include devices with capillary elements that extend from an edge of a body structure that is oriented substantially parallel to a mass spectrometer orifice during operation. These latter embodiments are typically more difficult to fabricate because they generally include precision-drilling blind holes into body structure edges.

Figure 11:
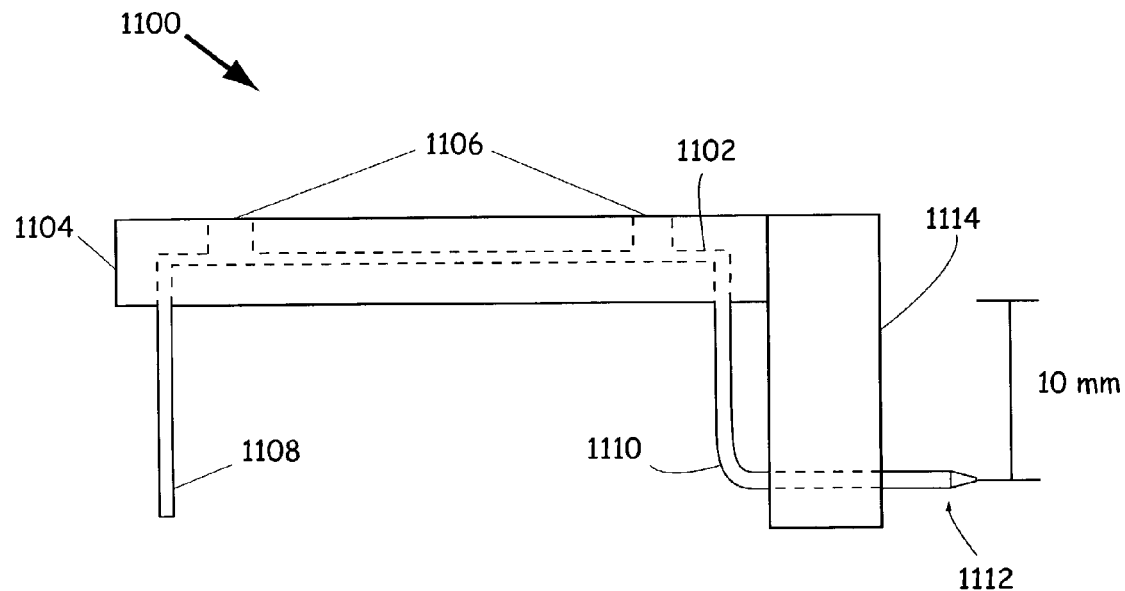
FIG. 11 schematically shows a side view of one embodiment of a microfluidic sample delivery device that includes a linear sipper capillary element and a non-linear spray capillary element.

FIG. 11 schematically shows a side view one embodiment of a microfluidic sample delivery device that includes a linear sipper capillary element and a non-linear spray capillary element (e.g., a sip and spray device). As shown, microfluidic sample delivery device 1100 includes microchannel 1102 disposed within body structure 1104. Microfluidic sample delivery device 1100 also includes ports 1106, which fluidly communicate with microchannel 1102. Ports 1106 are typically used to connect fluid direction components to body structure 1104. Optional fluid direction component connections are described further below. Microfluidic sample delivery device 1100 also includes two capillary elements, which fluidly communicate with microchannel 1102, namely, linear sipper capillary element 1108 and non-linear spray capillary element 1110. Linear sipper capillary element 1108 is typically used to sip or draw fluidic materials into microchannel 1102, while non-linear spray capillary element 1110, which includes tapered spray tip or nozzle 1112, is typically used to spray aliquots of fluidic materials at a sample destination, such as an orifice to a mass spectrometer detector. In preferred embodiments, non-linear spray capillary element 1110 includes about 90° of arc. For example, the arc typically includes a radius of between about 5 mm and about 50 mm, more typically between about 6 mm and about 25 mm, and still more typically between about 7 mm and about 15 mm (e.g., about 10 mm). This typically depends on the inner and outer diameter of a given capillary element. For example, a capillary element that includes an inner diameter of about 20 µm and an outer diameter of about 360 µm is typically bent to include about a 10 mm radius, whereas a capillary element with about a 150 µm outer diameter and about a 20 µm inner diameter is typically bent to include a 5 mm radius. Microfluidic sample delivery device 1100 further includes support structure 1114, which is bonded or otherwise attached to body structure 1104. Support structure 1114 provides support to non-linear spray capillary element 1110, which is disposed through support structure 1114.

Figure 12A:
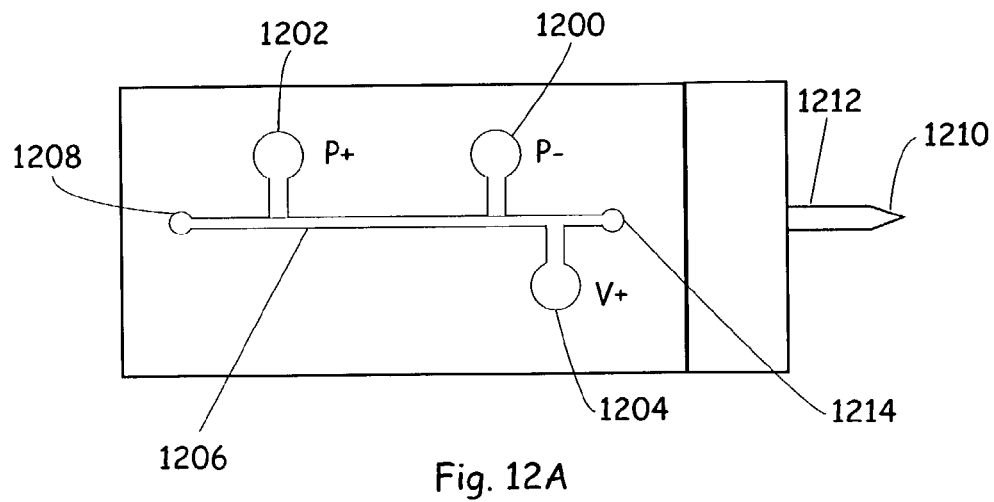
FIGS. 12A-C schematically depict various embodiments of fluid direction component connections to microfluidic sample delivery devices from top views.
Figure 12B:
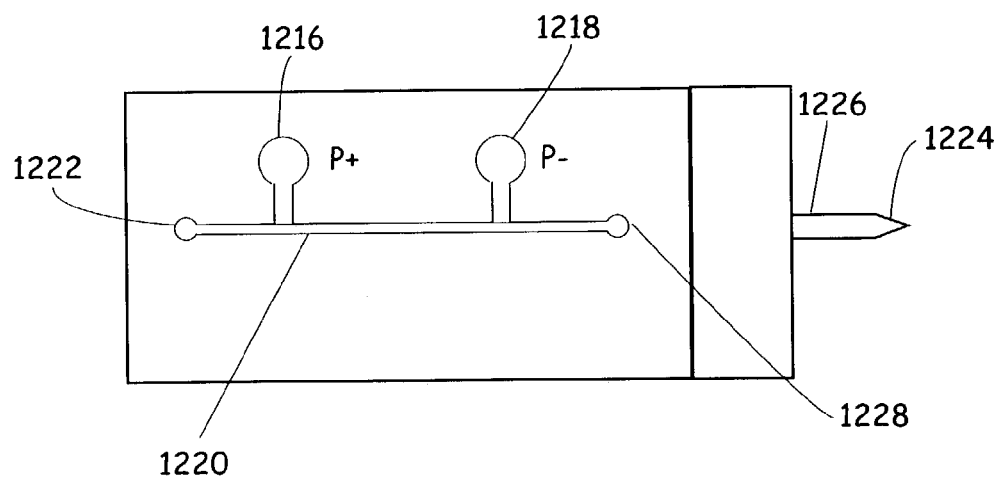
Figure 12C:
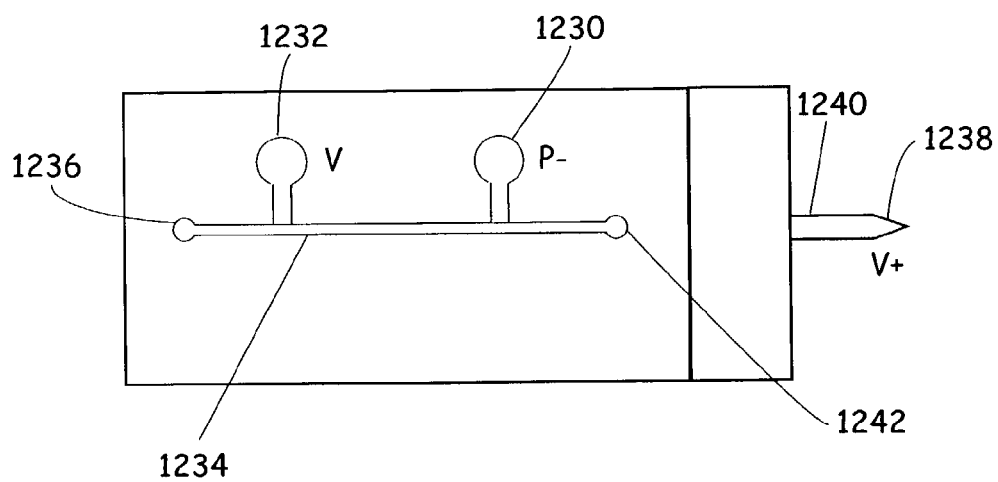

FIGS. 12A-C schematically depict various embodiments of fluid direction component connections to microfluidic sample delivery devices from top views. In particular, FIG. 12A schematically depicts a device (hybrid pneumatic/electrokinetic) that includes three ports (1200, 1202, and 1204, respectively), each of which fluidly communicate with microchannel 1206. A pressure force modulator (e.g., a vacuum pumping system, etc.) is optionally operably connected to port 1200 for applying negative pressure to sip or draw fluidic material into the device through a linear sipper capillary (not shown), which fluidly communicates with microchannel 1206 via linear sipper capillary connection point 1208. A pressure force modulator is also optionally operably connected to port 1202 for applying positive pressure to spray fluidic materials from tapered spray tip or nozzle 1210 of non-linear spray capillary element 1212, which fluidly communicates with microchannel 1206 via non-linear spray capillary element connection point 1214. An electrokinetic force modulator is optionally operably connected to port 1204 for biasing (i.e., supplying adequate electrical potentials to) fluidic materials to be electrosprayed from tapered spray nozzle 1202. FIG. 12B schematically depicts a device (i.e., a pneumatic only device) that includes two ports (1216 and 1218, respectively), each of which fluidly communicates with microchannel 1220. A pressure force modulator is optionally operably connected to port 1218 for applying negative pressure to sip or draw fluidic material into the device through a linear sipper capillary (not shown), which fluidly communicates with microchannel 1220 via linear sipper capillary connection point 1222. A pressure force modulator is also optionally operably connected to port 1216 for applying positive pressure to spray fluidic materials from tapered spray tip or nozzle 1224 of non-linear spray capillary element 1226, which fluidly communicates with microchannel 1220 via non-linear spray capillary element connection point 1228. FIG. 12C schematically depicts a device (hybrid pneumatic/electrokinetic) that includes two ports (1230 and 1232, respectively), each of which fluidly communicates with microchannel 1234. A pressure force modulator is optionally operably connected to port 1230 for applying negative pressure to sip or draw fluidic material into the device through a linear sipper capillary (not shown), which fluidly communicates with microchannel 1234 via linear sipper capillary connection point 1236. An electrokinetic force modulator is also optionally operably connected to port 1232 and tapered spray tip or nozzle 1238 (e.g., coated with a conductive coating, etc.) of non-linear spray capillary element 1240 for flowing and biasing fluidic materials to be electrosprayed from tapered spray nozzle 1238. For example, an electric field is applied between port 1232 and tapered spray tip or nozzle 1238 to produce an electrokinetic force for electrospraying. Conductively coated spray tips are described in greater detail below. Non-linear spray capillary element 1240 fluidly communicates with microchannel 1234 via non-linear spray capillary element connection point 1242.

At least one microscale cavity disposed within a device body structure typically includes a fluidic material to wash at least one of the linear and non-linear capillary elements, e.g., after a sample fluid has been flowed through the element. In preferred embodiments, the linear capillary element extends at least about 2.5 cm from the body structure, e.g., to adequately access (e.g., all the way to the bottom) wells in microwell plates (e.g., 96-well plates, 384-well plates, etc.). Typically, a terminus of the non-linear capillary element is tapered. For example, the non-linear capillary element typically includes a nozzle disposed proximal to a terminus thereof. Further, at least one of the linear and non-linear capillary elements is typically fabricated from a plastic, glass, quartz, metal, and/or other material. Optionally, at least a portion of at least one of the linear and non-linear capillary elements includes a hydrophobic coating. In certain embodiments, sample components are separated before being sprayed into the orifice of a mass spectrometer. For example, at least a portion of at least one of the linear and non-linear capillary elements and/or a microscale cavity optionally includes a chromatographic material to separate at least one component of the selected aliquots from other components prior to flowing the selected aliquots to the sample destination. Various liquid chromatography columns that are optionally adapted for use in the devices of the present invention are readily available from commercial suppliers (e.g., PicoFrit™ Nanobore LC Columns available from New Objective, Inc., Woburn, Mass.). Packed capillary spray tips optionally used in the devices of the present invention are described further in, e.g., U.S. Pat. No. 5,572,023, entitled "ELECTROSPRAY METHODS AND APPARATUS FOR TRACE ANALYSIS," to Caprioli, issued Nov. 5, 1996. Optionally, the microscale cavities further include electrodes disposed therein, which electrodes are operably connected to a power source to electrophoretically separate at least one component of the selected aliquots from other components prior to flowing the selected aliquots to the sample destination. Optionally, the at least one fluid direction component includes, e.g., a fluid pressure force modulator and/or an electrokinetic force modulator. In some embodiments, the body structure includes a plurality of linear capillary elements extending therefrom in which at least one member of the plurality fluidly communicates with the microscale cavities. Typically, each linear capillary element fluidly communicates with a microscale cavity. In certain embodiments, the body structure includes a plurality of non-linear capillary elements extending therefrom in which at least one member of the plurality fluidly communicates with the microscale cavities. Typically, each non-linear capillary element is in fluid communication with a microscale cavity in the device. The device also generally further includes a controller operably connected to the device, which controller (e.g., a device handling system) moves the device relative to the sample source and the sample destination. Controllers are described in greater detail below.

Figure 13:
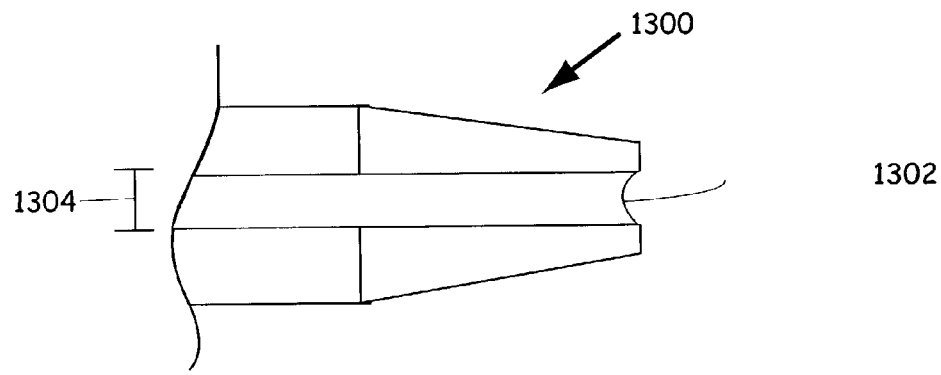
FIG. 13 schematically shows a cutaway view of a spray tip that includes a fluid meniscus.

In preferred embodiments, a channel disposed through the linear capillary element includes a larger cross-sectional dimension (e.g., about 360 μm outer diameter (OD)/50 μm inner diameter (ID)) than a channel disposed through the non-linear capillary element (e.g., about 360 μm OD/20 μm ID, with 20 to 2 μm ID transition in tapered spray tip). Typically, the channel disposed proximal to a terminus of the non-linear capillary element includes a cross-sectional dimension that produces a surface tension on fluidic materials disposed therein sufficient to prevent voiding the fluidic materials from the terminus, e.g., when a pressure is applied to the linear capillary element. For example, at least a portion of the channel typically includes a cross-sectional dimension of between about 1 μm and about 200 μm. To further illustrate, when the sipper is activated, a negative pressure is also produced at the spray tip. To avoid emptying the spray tip, the hydrodynamic impedance should be high enough. This is optionally done by making use of the pressure difference induced by surface tension at the capillary tip. For example, by reducing the inner diameter of the spray tip, this pressure difference can become substantial. FIG. 13 schematically shows a cutaway view of a spray tip that includes a fluid meniscus to further illustrate fluid pressure forces at spray tips. As shown, tapered spray tip 1300 includes fluid meniscus 1302 and cross-sectional channel dimension 1304. For a tip of inner diameter (2R), the pressure differential (ΔP) at the opening of a spray tip (e.g., tapered spray tip 1300) is given by $$2\gamma \cos \theta / R$$

where θ is the contact angle (e.g., for glass-water cos θ is about 1; hydrophilic, low contact angle),γ is the surface tension (e.g., about 70 dyne/cm for pure water, about 20 dyne/cm for water with detergent, etc.), and R is the radius of the channel. For example, if a channel disposed through a spray tip has an inner diameter of 4 μm (e.g., cross-sectional channel dimension 1304), R is 2 μm or $2 \times 10^{-4}$ cm. The pressure differential at the fluid-air interface (e.g., of fluid meniscus 1302) for such a 4 μm channel would be about 10 psi (i.e., $7 \times 10^5$ dyne/cm, $7 \times 10^4$ Pa, or 0.7 ATM) [2(70 dyne/cm)/$2 \times 10^{-4}$ cm]. In certain embodiments, samples are drawn or sipped through sipper capillary elements of devices described herein under a pressure of about 2 psi, which does not lead to the voiding of fluidic materials from the spray tip during the sipping operation. The value of γ=70 dyne/cm is a maximum for very pure water, and in practice it may be somewhat lower (e.g., about 35 dyne/cm), but there is typically enough margin such that the spray tip always remains filled.

Figure 14:
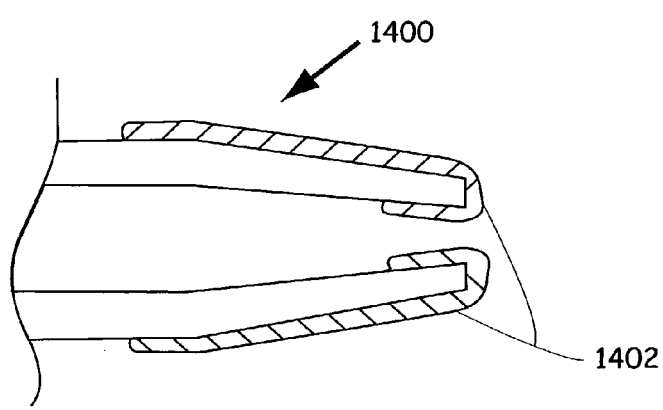
FIG. 14 schematically illustrates a cutaway view of a spray tip that includes a conductive coating.

In preferred embodiments, at least a portion of at least one of the linear and non-linear capillary elements includes at least one conductive coating operably connected to a power source to produce a potential gradient in the portion. For example, the at least one conductive coating optionally includes a Ti adhesion layer and an Au layer disposed over the Ti adhesion layer. The Ti adhesion layer optionally includes a thickness of at least about 300 angstroms. In contrast, the Au layer typically includes a thickness of between about 2000 angstroms and about 3000 angstroms. For example, to ensure electrical contact to internal surfaces proximal to a tapered spray tip, these conductive coatings are optionally sputtered using techniques generally known in the art to produce the electrical contacts. Sputtering will typically ensure that a short length of the inside of the tip is coated. FIG. 14 schematically illustrates a cutaway view of a spray tip that includes a conductive coating. As shown, tapered spray tip 1400 includes conductive coating layer 1402 that coats both short lengths of external and internal surfaces of tapered spray tip 1400. In preferred embodiments, capillary elements that include hydrophobic surfaces (e.g., include a polyimide coating or the like) at least proximal to the tip, though the hydrophobic surfaces can also extend from the tip.

The invention also relates to methods of delivering a fluidic sample to a sample destination using, e.g., a sip and spray device. The methods include (a) providing a microfluidic device that includes (i) a body structure that includes one or more microscale cavities disposed therein, (ii) at least one linear capillary element extending from the body structure, which linear capillary element fluidly communicates with the one or more microscale cavities, (iii) at least one non-linear capillary element extending from the body structure, which non-linear capillary element fluidly communicates with the one or more microscale cavities, and (iv) a support structure connected to the body structure and to at least a segment of the non-linear capillary element to provide support thereto. A terminus of the non-linear capillary element typically includes a nozzle. The methods also include (b) drawing at least one selected aliquot of the fluidic sample from a sample source (e.g., a microwell plate, etc.) into the body structure through the linear capillary element, and (c) expelling the selected aliquot of the fluidic sample from the non-linear capillary element at the sample destination (e.g., an inlet to a mass spectrometer, etc.).

In certain embodiments, (b) further includes drawing a buffer into at least a portion of the body structure through the linear capillary to prime the body structure prior to drawing the selected aliquot. Optionally, the methods further include separating at least one component of the selected aliquot from other components prior to expelling the selected aliquot from the non-linear capillary element. In preferred embodiments, a fluid flow rate is faster in (b) than in (c). Optionally, (b) and (c) include using a pressure force modulator to draw and expel the selected aliquot. In certain embodiments, (c) includes electrospraying the selected aliquot from the non-linear capillary element. For example, optionally (b) includes drawing the selected aliquot using a pressure force modulator and (c) includes expelling the selected aliquot using an electrokinetic force modulator.

The body structure optionally includes a plurality of linear capillary elements extending therefrom in which at least one member of the plurality fluidly communicates with the microscale cavities. For example, (b) optionally includes using at least two members of the plurality sequentially or simultaneously. In some embodiments, the body structure includes a plurality of non-linear capillary elements extending therefrom in which at least one member of the plurality fluidly communicates with the microscale cavities. Optionally, (c) includes using at least two members of the plurality sequentially or simultaneously.

The methods optionally further include (d) washing at least one of the linear and non-linear capillary elements with at least one buffer solution. Optionally, (b)-(d) are repeated. In some embodiments, the methods also include (d) flowing one or more fluidic materials from at least one microscale cavity to wash at least one of the linear and non-linear capillary elements. In these embodiments, (b)-(d) are also optionally repeated. In still other embodiments, (d) includes detecting a detectable signal produced by a sample component that is sprayed or otherwise expelled from the non-linear capillary element.

D. Embodiments Involving Device Rotation

The present invention also relates to micropipetting devices and methods for transferring fluidic samples, e.g., from a horizontal plane of a microwell plate to a vertical plane of an input orifice of a typical mass spectrometer. In these embodiments, samples are typically not drawn into device body structures (e.g., low cost molded cylinders, microfluidic device body structure, etc.). Instead, fluidic samples are generally drawn only into a portion of sipper capillary elements, which are used as a micropipettes. One advantage of these approaches is that they avoid potential contamination associated with glue at joints between capillary elements and device body structures.

In particular, one aspect of the invention relates to a fluidic sample delivery device that includes (a) a rotatable molded cylinder that includes at least one fluid conduit (e.g., fabricated from plastic, glass, quartz, metal, and/or the like) extending therefrom, and (b) a controller operably connected to the rotatable molded cylinder which rotates the fluid conduit between a sample source (e.g., a microwell plate, etc.) and a sample destination (e.g., an inlet to a mass spectrometer, etc.). In preferred embodiments, a terminus of the fluid conduit includes a nozzle. The rotatable molded cylinder optionally includes at least one cavity that fluidly communicates with the fluid conduit from which fluidic materials are capable of being flowed to wash the fluid conduit. In certain embodiments, the rotatable molded cylinder includes a plurality of fluid conduits. The fluidic sample delivery device also includes (c) at least one fluid direction component operably connected to the fluid conduit (e.g., a capillary element having a channel disposed therethrough, etc.) which draws selected aliquots of at least one fluidic sample from the sample source into the fluid conduit and expels the selected aliquots from the fluid conduit at the sample destination. For example, the sample source and the sample destination are typically disposed about 90° apart relative to the rotatable molded cylinder. The controller typically includes a mechanical arm operably connected to the rotatable molded cylinder. The fluid direction component optionally includes a fluid pressure force modulator and/or an electrokinetic force modulator. For example, in certain embodiments, the fluid direction component includes a pressure force modulator, which applies pressure to draw the selected aliquots into the flexible fluid conduit and an electrokinetic force modulator, which applies a potential gradient along a length of the flexible fluid conduit to electrospray the selected aliquots at the sample destination.

Figure 15:
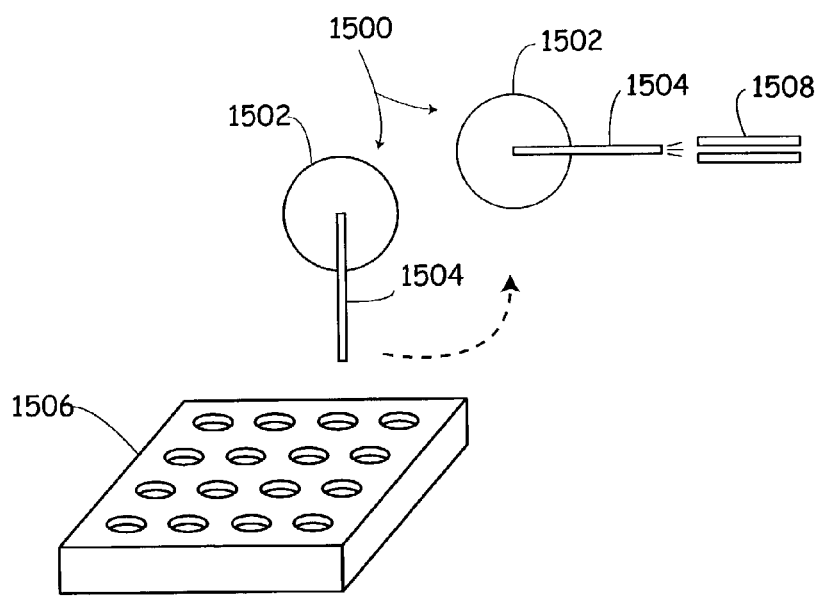
FIG. 15 schematically shows a sample delivery device that includes a rotatable molded cylinder according to one embodiment of the invention.

FIG. 15 schematically shows a sample delivery device that includes a rotatable molded cylinder according to these embodiments of the invention. As shown, delivery device 1500 includes rotatable cylinder 1502 and capillary element 1504. Optionally, a microfluidic device such as the one schematically depicted in FIG. 2 (described further above) is used instead of delivery device 1500. Although not shown, a fluid direction component, such as a pressure force modulator and/or a electrokinetic force modulator is typically operably connected to capillary element 1504. During operation, a controller or handling system (not shown) attached to delivery device 1500 typically lowers delivery device 1500 such that capillary element 1504 contacts a fluidic sample disposed in a container, such as a well in microwell plate 1506. The fluid direction component typically draws or sips a selected aliquot of the fluidic sample into capillary element 1504. Optionally, capillary element 1504 is partially filled with a buffer solution, e.g., to prime capillary element 1504 prior to contacting fluidic samples. Thereafter, the handling system generally raises delivery device 1500 away from microwell plate 1506 to clear a path of rotation between microwell plate 1506 and mass spectrometric orifice 1508. Once clear, handling system typically rotates delivery device 1500 approximately 90° such that capillary element 1504 is positioned proximal to mass spectrometric orifice 1508 and fluid direction component electrosprays the selected sample aliquot proximal to mass spectrometric orifice 1508 for analysis. After a sample is sprayed at mass spectrometric orifice 1508 delivery device 1500 is typically rotated back to the initial position, capillary element 1504 is cleaned, e.g., in a fluid trough or other container, and capillary element 1504 is optionally re-primed with a buffer solution. This process is optionally repeated to spray additional sample aliquots. The fluid direction component is typically configured such that vacuum (i.e., negative pressure) is applied to capillary element 1504 only while capillary element 1504 is oriented vertically, whereas positive pressure and voltage are applied to capillary element 1504 only while capillary element 1504 is oriented horizontally, e.g., rotated into a spraying position proximal to mass spectrometric orifice 1508. In certain embodiments, the rotatable molded cylinders include multiple capillary elements, e.g., disposed around the circumference of the cylinder, along a length of the cylinder, or the like to accommodate multiple sample aliquots to further enhance assay throughput. Further, in addition to sipping a single sample, a sipper capillary element is optionally configured (e.g., provided with a suitable length, etc.) to sip multiple samples, e.g., with intervening slugs of buffer. This approach allows the cleaning time to be amortized over multiple samples. The length of a given sample volume in a sipper capillary element is generally determined by the sample concentration, the mass spectrometer analysis time used, the cross-sectional dimension (e.g., diameter, etc.) of the channel within the sipper capillary element, and the flow rate of the sample sprayed from the capillary element.

The invention also provides methods of delivering fluidic samples to sample destinations that involve using rotatable molded cylinders. More specifically, the methods include (a) providing a rotatable molded cylinder that includes at least one fluid conduit (e.g., a capillary element having a channel disposed therethrough, etc.) extending therefrom, and (b) drawing at least one selected aliquot of at least one fluidic sample from a sample source (e.g., a microwell plate, etc.) into the fluid conduit. In certain embodiments, (b) includes drawing the selected aliquot into the fluid conduit using a pressure force modulator or an electrokinetic force modulator operably connected to the rotatable molded cylinder. A terminus of the fluid conduit typically includes a nozzle. Optionally, (b) further includes drawing a buffer into the fluid conduit prior to drawing the selected aliquot. The methods further include (c) rotating the rotatable molded cylinder from the sample source to the sample destination, and (d) expelling the selected aliquot at the sample destination (e.g., an inlet to a mass spectrometer, etc.). In some embodiments, (c) includes rotating the rotatable molded cylinder using a controller that includes a mechanical arm operably connected to the rotatable molded cylinder. In other embodiments, (c) includes rotating the rotatable molded cylinder about 90° between the sample source and the sample destination. In preferred embodiments, (d) includes electrospraying the selected aliquot from the fluid conduit using an electrokinetic force modulator operably connected to the rotatable molded cylinder. In certain embodiments, the rotatable molded cylinder includes a plurality of fluid conduits. For example, at least one of (b)-(d) are optionally performed using at least two members of the plurality sequentially or simultaneously. Further, (d) optionally includes simultaneously expelling selected aliquots from the at least two members and the method further includes flexing the at least two members toward each other prior to expelling the selected aliquots at the sample destination. In certain embodiments, the methods also include (e) washing the fluid conduit with at least one fluidic material. Optionally, (b)-(e) are repeated. In other embodiments, the methods further include (e) flowing at least one fluidic material out of the fluid conduit from at least one cavity of the rotatable molded cylinder that fluidly communicates with the fluid conduit to wash the fluid conduit. In these embodiments, (b)-(e) are also optionally repeated. In still other embodiments, the methods include (e) detecting detectable signals produced by components in the aliquot.

E. Embodiments Involving Flexing or Deflecting Flexible Capillary Elements

In one aspect, the invention provides a fluidic sample delivery device that includes (a) a holder having at least one flexible fluid conduit (e.g., a capillary element or the like), which flexible fluid conduit includes at least a first terminus and at least a second terminus, the first terminus extending from a first portion of the holder and the second terminus extending from a second portion of the holder. The holder is typically a disposable component of the sample delivery device (i.e., not intended for indefinite usage). The fluidic sample delivery device also includes (b) a sample source that includes at least one fluidic sample. The sample source is typically either integral with the holder or a separate component, such as a microwell plate or another fluid container. In addition, the device includes (c) a fluid conduit deflection component which selectively deflects the first terminus into contact with the fluidic sample and (d) at least one fluid direction component which flows selected aliquots of the fluidic sample into the flexible fluid conduit through the first terminus and out of the flexible fluid conduit through the second terminus at a sample destination. The sample destination typically includes an inlet to a detection device (e.g., a mass spectrometer, etc.). In preferred embodiments, an automated controller is operably connected to the holder, the fluid conduit deflection component, and/or the fluid direction component to direct movement of components relative to one another.

Figure 16A:
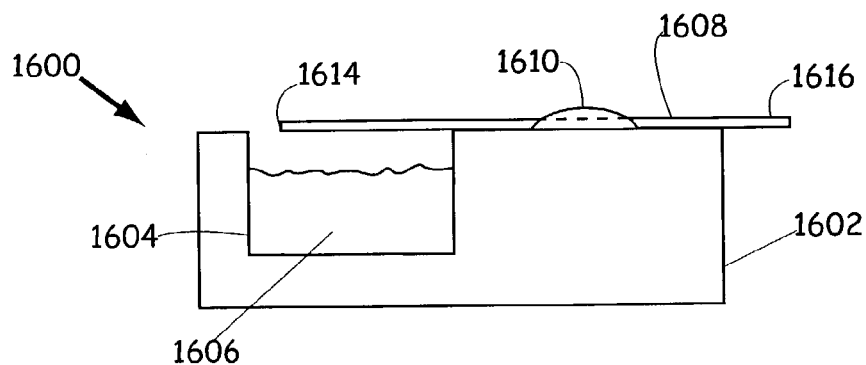
FIG. 16A schematically illustrates a cutaway side view of a sample delivery device that includes a flexible fluid conduit attached to a holder with an integral fluid container according to one embodiment of the invention.
Figure 16B:
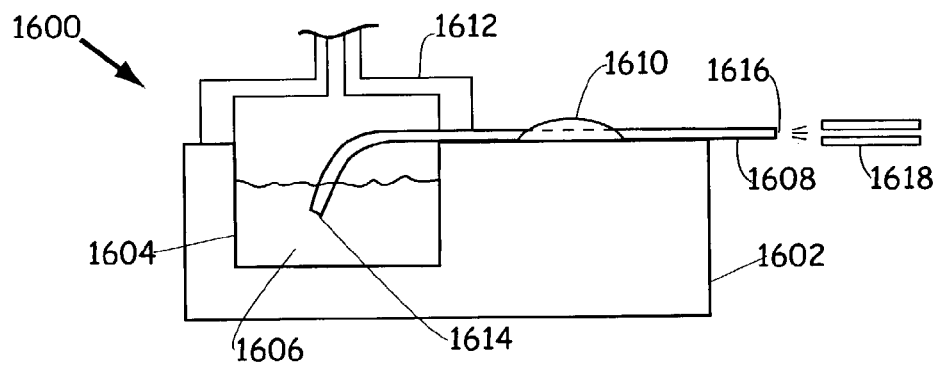
FIG. 16B schematically shows the sample delivery device of FIG. 16A with a cutaway side view of a pressure force modulator engaging the holder.
Figure 17:
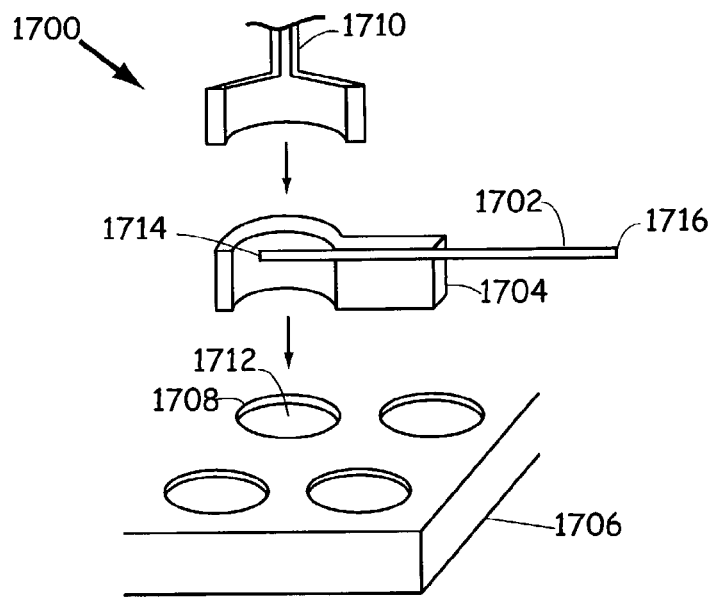
FIG. 17 schematically illustrates a cutaway side view of a sample delivery device that includes a flexible fluid conduit attached to a holder and a separate fluid container according to one embodiment of the invention.

FIG. 16A schematically illustrates a cutaway side view of sample delivery device 1600 that includes flexible fluid conduit 1608 attached to holder 1602 with integral fluid container 1604 according to one embodiment of the invention. As shown, delivery device 1600 includes holder 1602, which includes integral fluid container 1604 with fluidic material 1606 disposed, within fluid container 1604. Delivery device 1600 also includes flexible fluid conduit 1608 attached to holder 1602 by glue 1610. FIG. 16B schematically shows the sample delivery device of FIG. 16A with a cutaway side view of pressure force modulator 1612 engaging holder 1602. During operation, pressure force modulator 1612 applies positive pressure such that flexible fluid conduit 1608 is deflected into contact with fluidic material 1606, which is forced into first fluid conduit terminus 1614 and sprayed out of second fluid conduit terminus 1616, e.g., proximal to detection device orifice 1618. In contrast to the device schematically illustrated in FIG. 16, FIG. 17 schematically depicts a cutaway side view of sample delivery device 1700 that includes flexible fluid conduit 1702 attached to holder 1704 and microwell plate 1706, which is separate from holder 1704 according to one embodiment of the invention. During operation, holder 1704 engages well 1708 and pressure force modulator 1710 engages holder 1704. Pressure force modulator 1710 applies a positive pressure to force flexible fluid conduit into contact with fluidic material 1712 disposed within well 1708 such that aliquots of fluidic material 1712 is forced into first fluid conduit terminus 1714 and sprayed out of second fluid conduit terminus 1716 at a selected sample destination, such as a mass spectrometric system orifice for analysis. Although not shown in either FIG. 16 or 17, a controller or handling system is typically operably connected to device components to direct their relative movement.

The flexible fluid conduits (e.g., thin-walled conduits, etc.) include various embodiments. For example, the flexible fluid conduit optionally includes a plastic, glass, quartz, and/or metal material. In certain embodiments, the flexible fluid conduit includes a conductive coating operably connected to a power source to produce a potential gradient in the flexible fluid conduit. In other embodiments, the flexible fluid conduit includes a chromatographic material to separate at least one component of the selected aliquots from other components prior to flowing the selected aliquots out of the second terminus. Fluid conduits packed with chromatographic materials are described herein and are generally available from various commercial suppliers, such as New Objective, Inc. (Woburn, Mass.). Optionally, the flexible fluid conduit is removably attached to the holder, bonded or adhered to a surface of the holder, integral with the holder, or the like. In certain embodiments, the second terminus includes a nozzle. Nozzles generally have tapered, thin walls, e.g., to prevent compound from accumulating on surfaces of the nozzle, which are fabricated using laser cutting, fire polishing, and other techniques known in the art. The flexible fluid conduit typically includes a capillary element having a channel disposed therethrough. The channel generally includes a cross-sectional dimension of between about 1 µm and about 200 µm, more typically between about 1 µm and about 100 µm, and still more typically between about 1 µm and about 50 µm. For example, an outer surface of the capillary element and the channel typically include a cross-sectional shape independently selected from, e.g., a regular n-sided polygon, an irregular n-sided polygon, a triangle, a square, a rectangle, a trapezoid, a circle, an oval, or the like.

The fluid conduit deflection component is typically capable of mechanically or electrically deflecting the first terminus into contact with the fluidic sample. Optionally, the fluid conduit deflection component, the fluid direction component, or both components are removably connected to the holder, integral with the holder, or the like. In certain embodiments, the fluid direction component includes a fluid pressure force modulator, an electrokinetic force modulator, or both modulators. For example, the fluid direction component optionally includes an electrokinetic force modulator, which applies a potential gradient along a length of the flexible fluid conduit to electrospray the selected aliquots out of the second terminus. In some embodiments, the fluid conduit deflection component and the fluid direction component are a single component. For example, the single component optionally includes a fluid pressure force modulator capable of applying pressure to deflect the first terminus into contact with the fluidic sample and to flow the selected aliquots into the fluid conduit through the first terminus and out of the fluid conduit through the second terminus at the sample destination.

Figure 18:
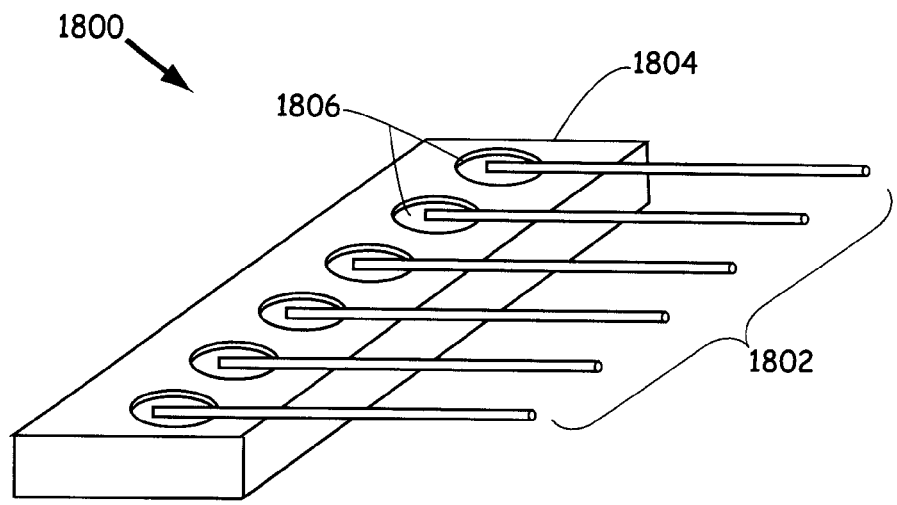
FIG. 18 schematically depicts a sample delivery device that includes an array of flexible fluid conduits attached to a holder according to one embodiment of the invention.

The first portion of the holder typically includes at least one cavity into (see, e.g., FIG. 16, described above) or through (see, e.g., FIG. 17, described above) which the fluid conduit deflection component is capable of selectively deflecting the first terminus. Optionally, the cavity includes the sample source (see, e.g., FIG. 16, described above), or the first portion and the sample source are separate from one another (see, e.g., FIG. 17, described above). In certain embodiments, the at least one cavity includes an array of cavities. In these embodiments, the holder or carrier optionally includes two or more flexible fluid conduits and the fluid conduit deflection component is capable of selectively deflecting the first terminus of at least one of the two or more flexible fluid conduits into or through at least one member of the array. For example, the fluid direction component is typically capable of flowing the selected sample aliquots out of second termini of the two or more fluid conduits sequentially or simultaneously at the sample destination. To further illustrate, FIG. 18 schematically depicts sample delivery device 1800 that includes array of flexible fluid conduits 1802 attached to holder 1804 according to one embodiment of the invention. Cavities 1806 are optionally disposed in or through holder 1804 as described above.

The present invention also relates to methods of delivering fluidic samples to sample destinations that involve deflecting flexible fluid conduits into contact with the fluidic samples. In particular, the methods include (a) deflecting at least a first terminus of at least one flexible fluid conduit into contact with at least one fluidic sample in a sample source (e.g., a microwell plate or the like) using a fluid conduit deflection component in which a holder includes the flexible fluid conduit, which flexible fluid conduit includes the first terminus and at least a second terminus, the first terminus extending from a first portion of the holder and the second terminus extending from a second portion of the holder. Optionally, the holder includes the sample source. The methods further include (b) flowing selected aliquots of the fluidic sample into the flexible fluid conduit through the first terminus and out of the flexible fluid conduit through the second terminus at the sample destination using at least one fluid direction component. The sample destination typically includes an inlet to a detection device (e.g., a mass spectrometer, etc.), where detectable signals produced by sample components are detected.

The method of delivering fluidic samples to a sample destination includes assorted embodiments. For example, the second terminus optionally includes a nozzle and the method further includes electrospraying the selected aliquots from the nozzle at the sample destination. In certain embodiments, the flexible fluid conduit includes a chromatographic material and (b) further comprises separating at least one component of the selected aliquots from other components prior to flowing the selected aliquots out of the second terminus. The flexible fluid conduit typically includes a capillary element having a channel disposed therethrough.

The at least one fluid direction component typically includes a fluid pressure force modulator, an electrokinetic force modulator, or both modulators. For example, the fluid direction component optionally includes an electrokinetic force modulator that applies a potential gradient along a length of the flexible fluid conduit to flow the selected aliquots through the flexible fluid conduit from the sample source to the sample destination.

The first portion of the holder typically includes at least one cavity into or through which the fluid conduit deflection component deflects the first terminus. Optionally, the cavity includes the sample source, or the first portion and the sample source are separate. In other embodiments, the at least one cavity comprises an array of cavities. The holder optionally includes two or more flexible fluid conduits and (a) further includes deflecting the first terminus of at least one of the two or more flexible fluid conduits into or through at least one member of the array using the fluid conduit deflection component. For example, (b) optionally includes flowing the selected aliquots from second termini of the two or more fluid conduits sequentially or simultaneously at the sample destination.

The fluid conduit deflection component optionally mechanically or electrically deflects the first terminus into contact with the fluidic sample. In certain embodiments, the fluid conduit deflection component and the fluid direction component are a single component. For example, the single component optionally includes a fluid pressure force modulator that applies pressure to deflect the first terminus into contact with the fluidic sample in (a) and to flow the selected aliquots through the flexible fluid conduit from the sample source to the sample destination in (b).

In another aspect, the invention provides a fluidic sample delivery device with which flexible fluid conduits are flexed between sample sources and sample destinations. In one embodiment, for example, the fluidic sample delivery device includes (a) a microfluidic device that includes at least one flexible fluid conduit (e.g., fabricated from plastic, glass, quartz, metal, etc.) extending therefrom and (b) a controller (e.g., an automated controller, etc.) operably connected to the flexible fluid conduit which flexes the flexible fluid conduit between a sample source (e.g., a microwell plate, etc.) and a sample destination (e.g., an inlet to a mass spectrometer, etc.). The controller is capable of flexing (e.g., mechanically, electrically, or the like) the flexible fluid conduit relative to a body structure of the microfluidic device. In preferred embodiments, a terminus of the flexible fluid conduit includes a nozzle. The controller typically includes a mechanical arm operably connected to the flexible fluid conduit. For example, a portion of the mechanical arm is optionally disposed in a guide track (e.g., an arched shape guide track, etc.) that guides movement of the mechanical arm. Optionally, the mechanical arm moved using pneumatic actuation otherwise available, e.g., for one or more wells disposed in the body structure. Another option is to integrate such a mechanism into the device handling system. In addition, the flexible fluid conduit is typically a capillary element having a channel disposed therethrough. The fluidic sample delivery device also includes (c) at least one fluid direction component operably connected to the microfluidic device which draws selected aliquots of at least one fluidic sample from the sample source into the flexible fluid conduit and expels the selected aliquots from the flexible fluid conduit at the sample destination. In preferred embodiments, the microfluidic device includes at least one cavity that fluidly communicates with the flexible fluid conduit from which fluidic materials are capable of being flowed to wash the flexible fluid conduit. Further, in certain embodiments, the sample source and the sample destination are disposed about 90° apart relative to the microfluidic device. In some embodiments, the microfluidic device includes a plurality of flexible fluid conduits. In certain of these embodiments, for example, the controller is capable of flexing each of the plurality of flexible fluid conduits sequentially or simultaneously. Multiple sipper capillary elements are typically operated in parallel to further increase throughput. For example, if the total spacing of capillary elements exceeds the size of the inlet orifice of, e.g., a mass spectrometer, either the capillaries are brought together (e.g., mechanically, etc.) at the orifice, or the device will be stepped to align selected fluid conduits to the orifice, e.g., using a device handling system.

Figure 19:
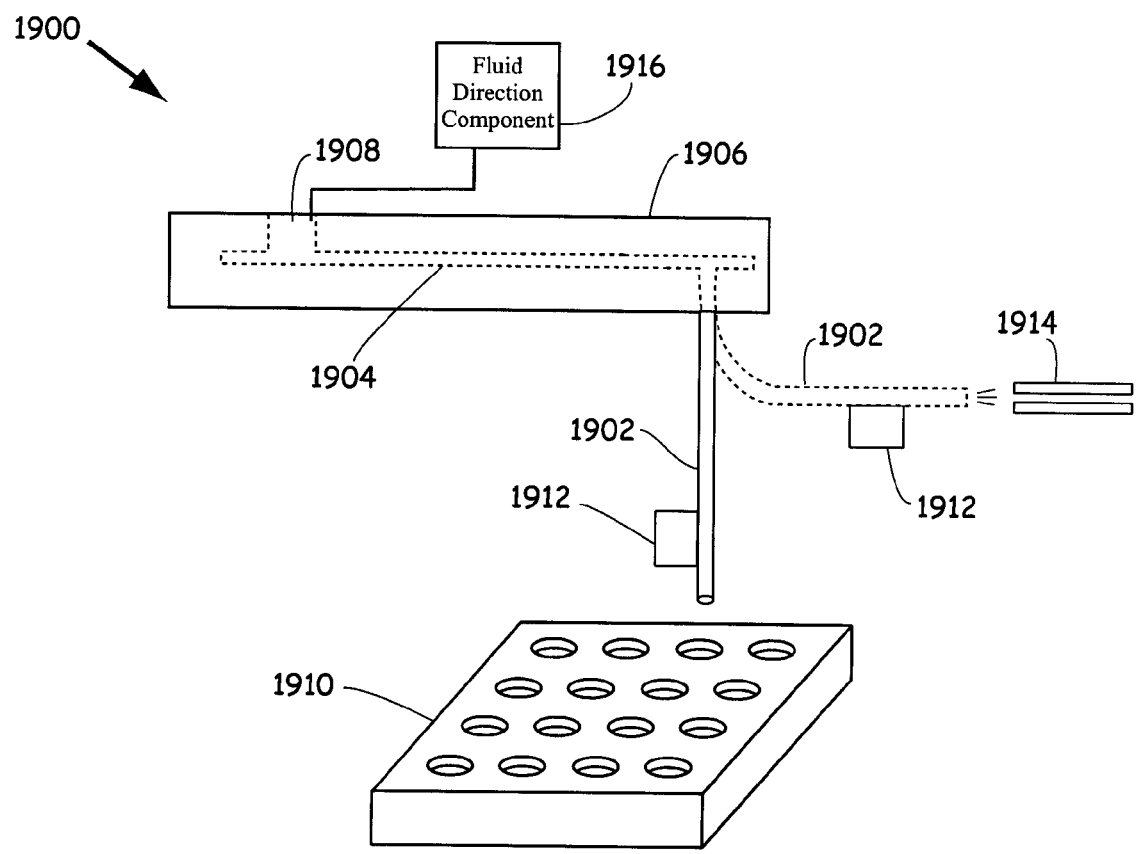
FIG. 19 schematically illustrates a side cutaway view of a sample delivery device with a flexible fluid conduit that is flexed between a sample source and a sample destination according to one embodiment of the invention.

To further illustrate, FIG. 19 schematically illustrates a side cutaway view of sample delivery device 1900 with flexible fluid conduit 1902. As shown, sample delivery device 1900 includes microchannel 1904 disposed within microfluidic device body structured 1906. Microchannel 1904 fluidly communicates with port 1908 and flexible fluid conduit 1902. A fluid direction component 1916 (e.g., a pressure force modulator, electrokinetic force modulator, etc.) typically engages microfluidic device body structure 1904 via port 1908. During operation, negative pressure is typically applied within flexible fluid conduit 1902 to draw selected aliquots of a fluidic material from a well on microwell plate 1910 into flexible fluid conduit 1902 (e.g., to avoid potential contamination from glue at a joint between flexible fluid conduit 1902 and microfluidic device body structure 1904) and optionally into microchannel 1904 as well. Thereafter, mechanical arm 1912 flexes flexible fluid conduit 1902 approximately 90° into proximity with mass spectrometric system orifice 1914. A positive pressure and/or an electroosmotic force is typically applied to the fluidic materials in sample delivery device 1900 to spray the fluidic materials into mass spectrometric system orifice 1914. Although not shown, a controller or handling system is typically operably connected to microfluidic device body structure 1906, e.g., to effect X-Y-Z translation of sample delivery device 1900 relative, e.g., to microwell plate 1910.

In certain embodiments, the fluid direction component includes a fluid pressure force modulator, an electrokinetic force modulator, or both modulators. Optionally, the direction component includes a pressure force modulator, which applies pressure to draw the selected aliquots into the flexible fluid conduit and an electrokinetic force modulator, which applies a potential gradient along a length of the flexible fluid conduit to electrospray the selected aliquots at the sample destination. Fluid direction components are described further below.

The present invention also provides methods of delivering fluidic samples to sample destination that involve flexing flexible fluid conduits. To illustrate, the methods include (a) providing a microfluidic device that includes at least one flexible fluid conduit (e.g., a capillary element having a channel disposed therethrough, or the like), and (b) drawing at least one selected aliquot of at least one fluidic sample from a sample source (e.g., a microwell plate, etc.) into the flexible fluid conduit. A terminus of the flexible fluid conduit typically includes a nozzle. In certain embodiments, (b) includes drawing the selected aliquot into the flexible fluid conduit using a pressure force modulator or an electrokinetic force modulator operably connected to the microfluidic device. In other embodiments, (b) further includes drawing a buffer into the microfluidic device prior to drawing the selected aliquot. In still other embodiments, (b) includes drawing multiple selected aliquots into the flexible fluid conduit. Optionally, the methods further include drawing a spacer fluid into the flexible fluid conduit after each selected aliquot. The methods also include (c) flexing the flexible fluid conduit from the sample source to the sample destination (e.g., an inlet to a mass spectrometer), and (d) expelling the selected aliquot from the flexible fluid conduit at the sample destination. Optionally, (c) includes flexing the flexible fluid conduit about 90° between the sample source and the sample destination. In preferred embodiments, (c) includes flexing the flexible fluid conduit using a controller that includes a mechanical arm operably connected to the flexible fluid conduit. A portion of the mechanical arm is optionally disposed in a guide track (e.g., an arched shape guide track, etc.) that guides movement of the mechanical arm. In preferred embodiments, (d) includes electrospraying the selected aliquot from the flexible fluid conduit using an electrokinetic force modulator operably connected to the microfluidic device.

In certain embodiments, the methods further include (e) washing the flexible fluid conduit with at least one fluidic material. Optionally, (b)-(e) are repeated. In still other embodiments, the method includes (e) flowing at least one fluidic material out of the flexible fluid conduit from at least one cavity of the microfluidic device that fluidly communicates with the flexible fluid conduit to wash the flexible fluid conduit. A portion of the at least one fluidic material is optionally flowed to a waste cavity to reduce carryover at a joint between the flexible fluid conduit and a body structure of the microfluidic device. Typically, the microfluidic device includes multiple cavities and the method further includes applying compensating force to fluids in cavities other than the at least one cavity from which the at least one fluidic material is flowed, e.g., to reduce fluid backflow into other cavities. In these embodiments, (b)-(e) are also optionally repeated. These methods also generally include detecting detectable signals produced by sample components sprayed from the flexible fluid conduits.

In some embodiments, the microfluidic device includes a plurality of flexible fluid conduits. In these embodiments, at least one of (b)-(d) is optionally performed using at least two members of the plurality sequentially or simultaneously. For example, (d) optionally includes simultaneously expelling selected aliquots from the at least two members and the method further includes flexing the at least two members toward each other prior to expelling the selected aliquots at the sample destination.

III. Upstream Processes

Many different upstream processes are optionally performed in methods that involve the devices of the present invention. As used herein, an "upstream" process refers to a process that is performed before a given sample aliquot is sprayed or otherwise expelled from a device of the present invention, e.g., at a sample destination. These processes are typically either performed within or external to the devices of the invention. Although essentially any upstream assay is performed involving the devices described herein, separation-based techniques will be emphasized herein for purposes of clarity. Many of these other processes, such as assays to detect transporter activity, gradient induced activities, or the like are described in, e.g., Published International Application No. WO 00/73799, entitled "MICROSCALE ASSAYS AND MICROFLUIDIC DEVICES FOR TRANSPORTER, GRADIENT INDUCED, AND BINDING ACTIVITIES," which was filed May 25, 2000 by Parce et al., which is incorporated by reference in its entirety for all purposes. Many other upstream processes are described in the references cited herein or generally known in the art.

To further illustrate, the present invention optionally includes separating materials, e.g., in a microfluidic device prior to spraying separated sample components into a detection system, such as a mass spectrometer for analysis. For example, first and second materials (e.g., enzymes, substrates, reactants, or the like) or other assay components are optionally flowed into contact in a mixing region, such as a microchannel or other cavity, of a device. Thereafter, the first or second material or a third material produced by contacting the first and second materials is flowed into a microchannel that includes a separation region. In certain embodiments, more than one product is formed by contacting the first and second materials. These are also optionally separated according to the methods described herein. The separation region of the microchannel includes a chromatographic material, that is either integral with, or coats, a surface within the channel. At least one of the first, second, or third material is separated from other material (e.g., the first material, the second material, the third material, or another material) in the separation region, and a resulting separated product is detected (e.g., by optical, spectroscopic, fluorescent, mass, luminescent, or another form of detection), e.g., upon being sprayed from the a device. In certain embodiments, at least one of the first, second, or third materials optionally includes a label. Other methods, such as sequential injection separations and renewable column separation, are also practiced according to the methods of the invention and are described further in, e.g., Grate et al., (1999) "Sequential Injection Separation and Sensing," in *Chemical Microsensors and Applications II* (from the proceedings of SPIE) 3857:70-73. Further, examples of microfluidic device-based separation systems, including those for capillary electrophoresis, capillary electrochromatography, and high-performance liquid chromatography are described in, e.g., Harrison et al. (1993) "Micromachining a Miniaturized Capillary Electrophoresis-Based Chemical Analysis System on a Chip," *Science* 261:895-897, Jacobson et al. (1994) "Open Channel Electrochromatography on a Microchip," *Anal. Chem.* 66:2369-2373, and Jacobson et al. (1994) "High Speed Separations on a Microchip," *Anal. Chem.* 66:1114-1118, which are incorporated by reference in their entirety for all purposes.

Aside from isocratic elutions in which the constituent materials to be separated have constant partition coefficients throughout the separation, the application of eluent gradients (e.g., continuous, stepped, or the like) are often appropriate. A gradient in eluent composition is typically used which becomes progressively more strongly eluting as the separation proceeds. To illustrate, in the case of many proteins there may be no conditions available in which a finite partition coefficient is observed between the mobile and stationary phases. For example, with ion exchangers, although the partition coefficient of, e.g., a monoanionic material typically varies linearly with the concentration of a competing monoanion in the eluent, that of a material that exchanges with x univalent anions may vary with the xth power of the concentration of competing monoanion. For proteins, there is generally no simple relation to net charge, but many singly charged eluent ions may exchange for one protein molecule. Thus, the partition coefficient changes sharply with concentration of the competing ion. A small change in this concentration effectively changes the protein from being completely adsorbed onto the chromatographic material in the separation region to being negligibly adsorbed. Nonetheless, protein separations are feasible, because desorption typically occurs for different proteins at different points in the gradient. As a result, the methods of the present invention generally include controlling the separation of materials and/or the elution of adsorbed materials from chromatographic materials in the separation region by varying the concentration of eluent (e.g., applying an ascending or a descending eluent gradient) flowed into the separation region from microchannels in fluid communication with the separation region. Specifically, separations are typically controlled and/or effected by, e.g., varying separation buffer or eluent pH, ionic strength, or the like. Appropriate eluents and separation buffers are well-known in the art.

The basis for separating materials according to the invention includes various distinguishing properties, such as net charge, polarity, polarizability, binding affinities, hydrophobic properties, hydrophilic properties, amphiphilic properties, electrostatic properties, or the like. These properties create distinguishing affinities of sample components for a given chromatographic material (i.e., an ion exchange material, a hydrophobic adsorbent material, a hydrophilic adsorbent material, an affinity adsorbent material, a metal chelating adsorbent material, an amphiphilic adsorbent material, an electrostatic adsorbent material, a chemisorbent, an immobilized enzyme, an immobilized receptor, an immobilized antibody, an immobilized antigen, or the like). As a result, the methods generally include contacting, e.g., first and second materials to produce at least a third material (e.g., a reaction product) that has a net charge in solution, or another distinguishing property, that is different from a net charge in solution of the first or second material (or an additional product or other material).

Materials, such as proteins, are optionally separated according to the methods of the present invention on the basis of net charge differences by ion chromatography. For example, if a protein has a net positive charge at pH 7, it will usually bind to a chromatographic material (e.g., one having negatively charged functional groups, such as carboxylate groups or the like) in the separation region, whereas a negatively charged protein in the separation region will not adsorb on the chromatographic material. A positively charged protein bound to such a chromatographic material is then optionally eluted by increasing the concentration of, e.g., NaCl or another salt in the eluting buffer. $Na^+$ ions compete with positively charged groups on the protein for binding to the chromatographic material in the separation region. Proteins that have relatively low net positive charge densities will elute first, followed by those having relatively high charge densities. Anionic materials are optionally separated according to the methods of the invention by using chromatographic materials having, e.g., positively charged diethyl-aminoethyl functional groups or the like. Cationic materials are optionally separated on chromatographic materials having, e.g., negatively charged carboxymethyl functional groups or the like. Other exemplary ionic exchange chromatographic materials are described further below. Many of these and others appropriate to the invention are known to those of skill. Additional details pertaining to ion chromatography are described in, e.g., Jandik and Cassidy, *Advances in Ion Chromatography* (1989) Waters Corporation, Weiss, *Ion Chromatography* (1995) VCH Publications, Fritx and Gjerde, *Ion Chromatography*, $3^{rd}$ Ed. (2000) John Wiley & Sons, and Tarter, *Ion Chromatography* (1987) Marcel Dekker.

Affinity chromatography is another powerful separation technique that is optionally used to separate many different types of materials, including proteins. This separation method takes advantage of the high affinity of, e.g., many proteins for specific functional groups, such as receptors for their agonists, antibodies for their cognate antigens, proteins with metal binding sites for their metal ions (e.g., a chelating adsorbent material), and enzymes for their substrates, cofactors, effectors, inhibitors, or the like (e.g., a specific protease for a protease inhibitor, or the like). Note, that either the protein or its particular ligand is optionally incorporated as the functional unit of the chromatographic material. Adsorbents are also optionally constructed to include a group that is close enough to the natural ligand of the protein such that the adsorbent binds the protein specifically. Additionally, a spacer arm is optionally attached so that the site on the protein can be reached, e.g., even if the binding site is in a cavity in the protein. Adsorbed proteins are optionally desorbed by, e.g., an increase of ionic strength or by competition for the site on the protein with a soluble ligand. Other details regarding affinity-based separations is described in, e.g., Bailon et al. (Edt), *Affinity Chromatography: Methods and Protocols* (*Methods in Molecular Biology*), (2000) Humana Press, Kline, *Handbook of Affinity Chromatography* (1993) Marcel Dekker, Inc., and Chaiken (Edt), *Analytical Affinity Chromatography* (1987) CRC Press.

Other separation techniques optionally used to practice the methods of the present invention include, e.g., hydrophilic, amphiphilic, hydrophobic interaction chromatography, or the like. Hydrophilic interaction chromatography is a variant of normal-phase chromatography. Elution occurs roughly in the opposite order of reverse phase chromatography, that is, the least polar compounds tend to elute first, the most polar last (i.e., elution is in the order of increasing polarity). Hydrophilic interaction chromatography generally involves chromatographic materials (i.e., stationary phases) that are highly polar (e.g., polyhydroxyethyl groups, or the like). The technique typically works well, e.g., for lipopeptides, amyloid peptides, histones, membrane proteins, oligonucleotides or analogs thereof, complex carbohydrates, phospholipids, glycopeptides, phosphopeptides, synthetic peptides, natural peptides, or the like. Hydrophilic-based separation techniques generally elute with decreasing gradients of, e.g., acetonitrile, propanol, or the like in aqueous buffers. Additional details regarding these techniques are provided in, e.g., Zhang and Wang, (1998) *J. Chromatogr.* 712:73, Lane et al., (1994) *J. Cell Biol.* 125:929, Jeno et al., (1993) *Anal. Biochem.* 215:292; Alpert (1990) *J. Chromatogr.* 499:177-196; Jenoe et al., (1993) *Anal. Biochem.* 215:292-298; Berna et al., (1997) "Polyol Promoted Adsorption of Serum Proteins to Amphiphilic Agarose Based Adsorbents" *J. Chromatogr.* 764:193-200 and Berna et al., (1996) "Cosolvent-Induced Adsorption and Desorption of Serum Proteins on an Amphiphilic Mercaptomethylene Pyridine-Derivatized Agarose Gel." *Arch. Biochem. And Biophys.* 330:188-192.

Hydrophobic interaction chromatography typically involves the use of chromatographic materials that have non-polar alkane or aromatic functional groups, such as phenyl, n-octyl, n-butyl, or the like. In general, the longer the alkane, or the larger the aromatic group, the stronger the binding interaction will be. Many proteins are able to sequester these functional groups on their surfaces and this exclusion from the solvent provides the basis of the binding energy. This interaction is typically enhanced by increasing ionic strength such that proteins are generally bound under high salt concentrations and eluted under low salt conditions. As a result, this techniques is typically used not only to purify a protein sample, but also to desalt the sample. Due to the nature of hydrophobic interactions and ionic strength, hydrophobic interaction chromatography and ion chromatography are optionally used sequentially. To illustrate, after a hydrophobic separation region is eluted in low salt, the collected sample is optionally run through a separation region that includes a chromatographic material with ion exchange properties, since low salt conditions are typically used to bind materials to ion exchange chromatographic materials. Conversely, following an ion exchange separation a protein sample is typically in high salt conditions which are usually favorable for binding to a hydrophobic chromatographic material. Other details pertaining to hydrophobic interaction chromatography are included in, e.g., Goheen and Gibbins (2000) "Protein losses in ion-exchange and hydrophobic interaction high-performance liquid chromatography," *J. Chromatogr.* 890(1):73-80 and Teal et al., (2000) "Native purification of biomolecules with temperature-mediated hydrophobic modulation liquid chromatography," *Anal. Biochem.* 283(2):159-65.

Figure 20:
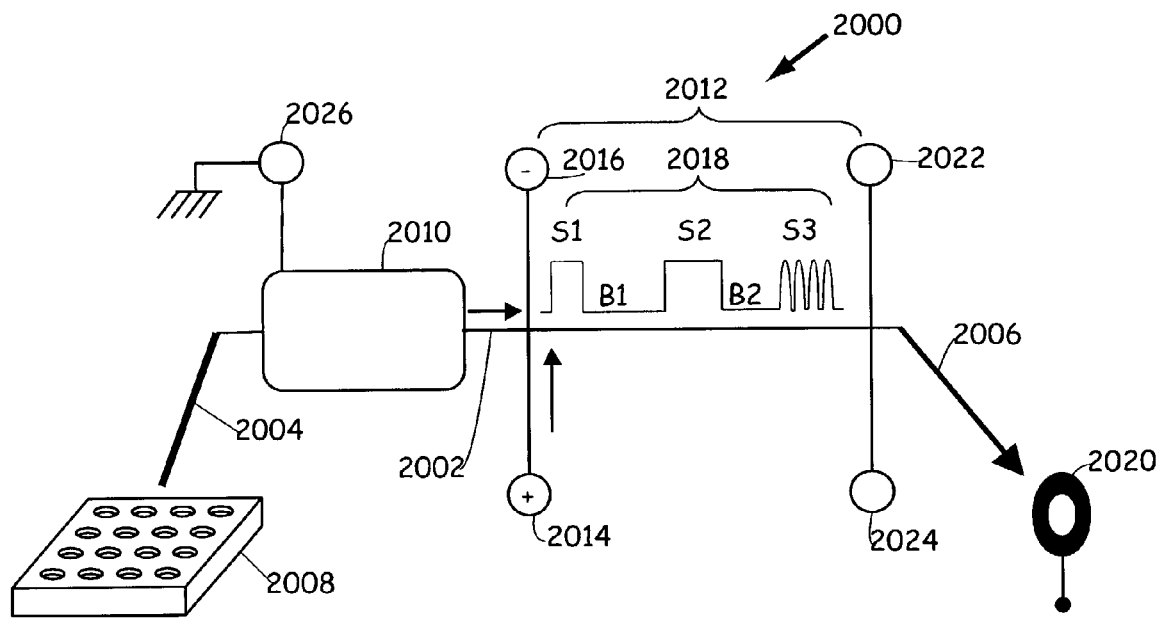
FIG. 20 schematically depicts a device configured to separate sample components prior to being electrosprayed into a mass spectrometer orifice.

FIG. 20 schematically depicts one embodiment of a device (e.g., a sip and spray device described above) configured to separate sample components prior to being electrosprayed into a mass spectrometer orifice. As shown, sample delivery device 2000 includes main microchannel 2002, which fluidly communicates with sipper capillary element 2004 and spray capillary element 2006. During operation, fluidic sample materials are typically drawn from wells on microwell plate 2008 through sipper capillary element 2004 and into sample storage cavity 2010. Aliquots of sample are typically introduced into separation region 2012 (e.g., for performing chromatographic separations, etc.) from sample storage cavity 2010 using a gated injection process in which sequential sample aliquots are separated by selected volumes (e.g., slugs) of buffer flowed under positive pressure from buffer well 2014, which fluidly communicates with main microchannel 2002 upstream from separation region 2012. Certain waste materials are typically directed under negative pressure to waste well 2016, which also fluidly communicates with main microchannel 2002 upstream from separation region 2012. Separation profile 2018 schematically depicts three sample aliquots (S1, S2, and S3, respectively) in separation region 2012 separated by buffer slugs B1 and B2. Prior to being electrosprayed from spray capillary element 2006 to mass spectrometer orifice 2020, separated components in a given sample aliquot are desalted by washing the aliquot with desalting solution flowed from desalting solution well 2022, which fluidly communicates with main microchannel 2002 downstream from separation region 2012. Waste materials are typically directed to desalting waste well 2024, which also fluidly communicates with main microchannel 2002 downstream from separation region 2012. As potential difference between sample delivery device 2000 and mass spectrometer orifice 2020 to achieve electrosprayed sample is typically maintained by applying high voltage to mass spectrometer orifice 2020. Sample delivery device 2000 is typically grounded via ground well 2026, which fluidly communicates with sample storage cavity 2010.

Many different materials are optionally separated according to these methods. For example, the first, second, or third material optionally includes a biological molecule, an artificial molecule, an ion, a polar molecule, an apolar molecule, an antibody, an antigen, an inorganic molecule, an organic molecule, a drug, a receptor, a ligand, a neurotransmitter, a cytokine, a chemokine, a hormone, a particle, a bead, a functionalized bead, a liposome, a cell, a nucleic acid, DNA, RNA, an oligonucleotide, a ribozyme, a protein, a phosphoprotein, a glycoprotein, a lipoprotein, a peptide, a phosphopeptide, a glycopeptide, a lipopeptide, an enzyme, an enzyme substrate, a product, a carbohydrate, a lipid, a label, a dye, a fluorophore, or the like. In one preferred embodiment, the first or second material includes, e.g., a kinase enzyme, a kinase enzyme substrate, or the like. Suitable kinase enzymes include, e.g., a protein kinase, a protein kinase A, a protein kinase B, a protein kinase C, a hexokinase, a phosphofructokinase, a phosphoglycerate kinase, a pyruvate kinase, a cyclic AMP-dependent protein kinase, a cyclic GMP-dependent protein kinase, a calmodulin-dependent protein kinase II, a casein kinase I, a casein kinase II, a glycogen synthase kinase-3, a cyclin-dependent kinase (e.g., CDK2, CDK4, CDK6, or the like), a p34/cdc2 kinase, a nucleic acid kinase, or the like. In another preferred embodiment, the materials to be separated include, e.g., a phosphatase enzyme, a phosphatase enzyme substrate, a dephosphorylated product, or the like. Essentially any phosphatase is suitable for use in the assays of the present invention, such as those comprising the EC number 3.1.3. To further illustrate, phosphatase enzymes that are optionally use in the assays described herein include, e.g., a protein phosphatase, an acid phosphatase, an alkaline phosphatase, a sugar phosphatase, a polynucleotide phosphatase, or the like.

The chromatographic materials in the present invention are optionally disposed within the separation region using various techniques. In general, chromatographic materials appropriate for the methods and devices of the present invention are known to those of skill and are readily available from many different commercial suppliers. For example, chromatographic materials are available from Sigma (St. Louis, Mo.), Suppleco (Belle Porte, Pa.), and the like. See, e.g., the 2000 Sigma Catalogue or the 1997 Suppleco Chromatography Products Catalogue). For example, an inner surface of the separation region optionally includes the chromatographic material (i.e., is integral with the surface of the microchannel at least, e.g., in the separation region). The chromatographic material is optionally applied to the microchannel surface in the separation region as a coating either before or during a particular assay. Preferred chromatographic materials suitable for use in the separations of the present invention include, e.g., polyarginine, polylysine, modified polyacrylamide, modified dimethylacrylamide, a nonionic detergent (e.g., Triton X-100™, etc.), an ionic detergent, amphiphilic materials, or the like.

The methods of the present invention optionally include, e.g., flowing the chromatographic material into the separation region, flowing a second chromatographic material into the separation region, or flowing three or more chromatographic materials or surface coatings into the separation region to achieve, e.g., the desired ion-exchange characteristic for a particular assay, e.g., an anionic or cationic exchange surface or medium. Alternatively, the chromatographic material is continuously flowed into the separation region for a selected period of time (e.g., in which the phase that includes the material to be separated flows at a different rate than the phase that includes the continuously flowed chromatographic materials within the separation region), or multiple aliquots of the chromatographic material are flowed into the separation region. In addition, the chromatographic material is optionally stored in a reservoir that is fluidly coupled to the separation region.

In certain embodiments, the chromatographic material is covalently or otherwise attached to, e.g., a plurality of microbeads and/or a gel. In these embodiments, the functionalized microbeads or the gel is generally retained in the separation region of the device by, e.g., an modified microchannel configuration, a semi-permeable membrane, or the like. A variety of configurations for controlling particles in microfluidic systems are found in, e.g., Published International Application Nos. WO 00/50172 "MANIPULATION OF MICROPARTICLES IN MICROFLUIDIC SYSTEMS," by Mehta et al. and WO 00/50642 "SEQUENCING BY INCORPORATION," by Parce et al. For example, a downstream end of the microchannel that includes the separation region is optionally tapered, narrowed, or otherwise altered to prevent the microbeads and/or gel from being flowed out of the region, while permitting the mobile phase to flow into and out of the separation region. Similarly, a semi-permeable membrane is optionally disposed across a downstream end of the separation region of the microchannel to retain the stationary phase.

IV. Downstream Processes

Various downstream processes are optionally performed which involve the sample delivery devices described herein. As used herein, a "downstream" process refers to a process that is performed after a given sample aliquot is sprayed or otherwise expelled from a device of the present invention, e.g., at a sample destination. Although essentially any downstream process is performed according to the present invention, sample detection and device washing are emphasized in this disclosure for purposes of clarity. Detectors and detection systems are described in greater detail below.

After a sample aliquot is delivered to a sample destination, e.g., electrosprayed into the orifice of a mass spectrometer, fluid channels (e.g., microchannels, channels within capillary elements, etc.) are typically washed, e.g., to prevent contamination of other sample aliquots that may subsequently be flowed through the channels. In certain embodiments, wash fluids are flowed from microscale cavities disposed within device body structures following sample delivery to wash selected device channels. Optionally, external components of the devices described herein are also washed, e.g., by rinsing external surfaces of capillary elements in buffer streams, in fluid wash troughs, or the like. Certain of these optional methods of washing the devices of the present invention are described further in, e.g., Published International Application No. WO 01/73396, entitled "METHODS OF REDUCING FLUID CARRYOVER IN MICROFLUDIC DEVICES," which was filed Mar. 26, 2001 by Wolk et al., which is incorporated by reference in its entirety for all purposes.

Figure 21:
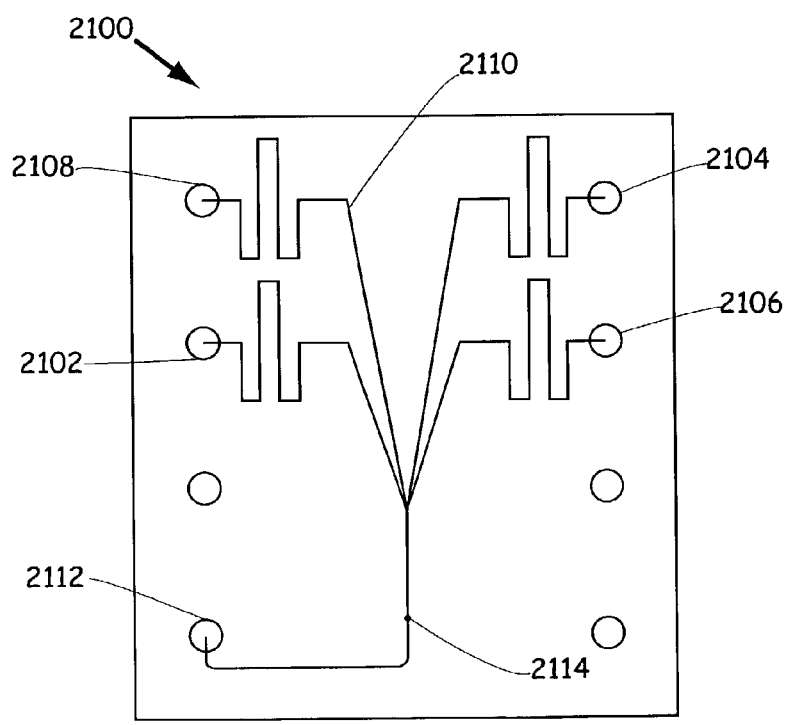
FIG. 21 schematically depicts a top view of one embodiment of a sample pipetting device from which cleaning fluids are flowed from device cavities to wash a pipettor capillary element that extends from the device.

The methods of washing capillary element channels that involve flowing wash fluids from device cavities generally significantly enhance throughput, e.g., relative to approaches that include drawing wash fluids into devices from external sources. To illustrate, for a sample delivery device that includes separate sipper and spray capillary elements, the time for a sample to go through the device via both capillaries is estimated at about 20 seconds for a typical device. A subsequent cleaning step that involves drawing fluids from external sources will generally take at least twice as long, e.g., to remove essentially all of the previous sample, before the system is ready for the next sample. Thus, in these particular devices, minimum cycle times (i.e., sample spraying and device cleaning) are typically on the order of about 60 seconds. These cycle times can be dramatically reduced if samples are only drawn into a portion of a capillary element, instead of into device body structures, and followed by flowing washing fluids directly from cavities within device body structure, instead of from external sources. Such a device is illustrated in FIG. 21, which schematically depicts a top view of one embodiment of a sample pipetting device from which cleaning fluids are flowed from device cavities to wash a sipper/spray capillary element that extends from the device. As shown, device 2100 includes cleaning solution wells 2102, 2104, and 2106 and buffer well 2108, which fluidly communicate with microchannel network 2110. Device 2100 also includes a pipetting capillary element (not within view) that fluidly communicates with microchannel network 2110 via waste well 2112 and reverse swept joint 2114. Reverse swept joints are typically included to reduce carryover at the capillary element/body structure joint. For example, this fraction is typically only about 10% of the total flow volume. This is generally good practice even when the carryover is between successive cleaning solutions, rather than between samples. A swept joint (reverse or not) reduces fluid carryover by eliminating dead volume (volume with no flow) that otherwise exists at the edge of the joint.

During operation, sample aliquots are typically drawn only into the pipetting capillary element (i.e., not into microchannel network 2110 via reverse swept joint 2114). After samples are sprayed from the capillary element (e.g., orthogonally electrosprayed, etc.) positive pressure is typically applied to cleaning solution wells 2102, 2104, and 2106 and buffer well 2108 in rapid succession to clean the capillary element. For example, cleaning solution wells 2102, 2104, and 2106 typically contain solutions to remove compounds, such as acids, bases, solvents, oxidizing agents, or the like. When pressure is applied to one of these wells, a compensating pressure is typically applied to the other three to greatly reduce backflow in the channels leading to the other three wells. In particular, these channels are typically made long enough to ensure that an amount of backflow generally cannot reach a given well itself. To enhance throughput, each cleaning step is generally performed using the maximum pressure available such that a cleaning step typically only takes a few seconds to complete. Among the advantages of placing cleaning solutions in the device body structures is that the previous sample materials are removed from the device, rather than being accumulated, e.g., in one of the wells. In addition, as microwell plates are typically not moved during the cleaning step, which is generally the case when cleaning solutions are drawn from such plates, throughput is further enhanced.

Figure 22:
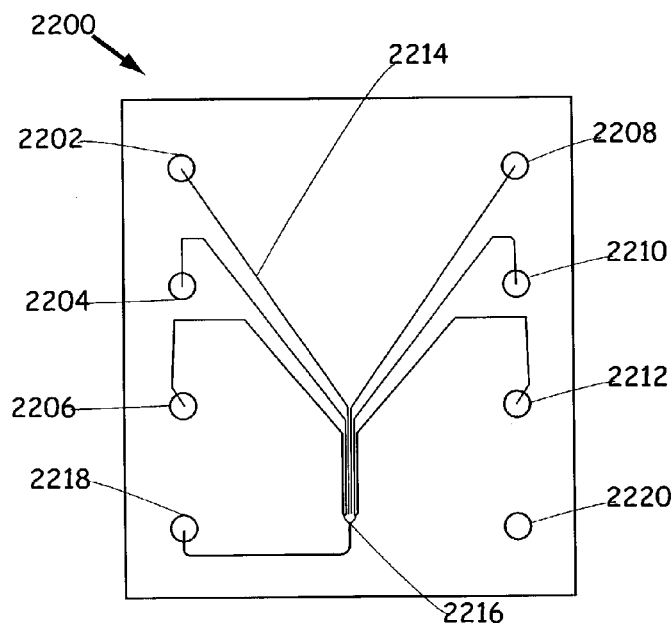
FIG. 22 schematically depicts a top view of another embodiment of a sample pipetting device from which cleaning fluids are flowed from device cavities to wash a pipettor capillary element that extends from the device.
Figure 23:
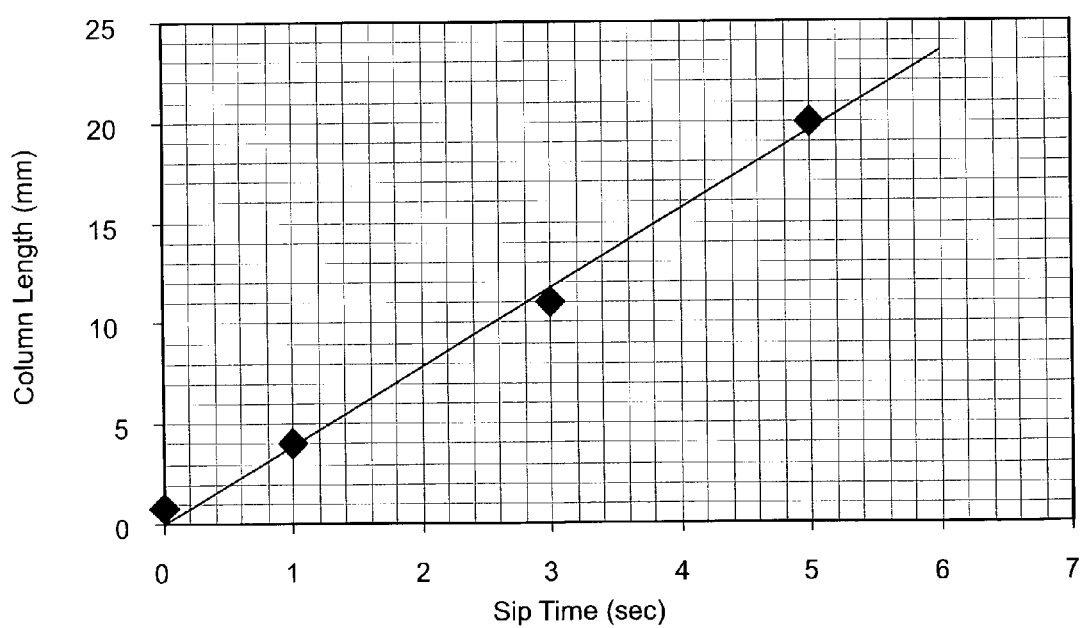
FIG. 23 is graph that shows a sipping calibration performed using a device like the one schematically depicted in FIG. 30.

FIG. 22 schematically depicts a top view of another embodiment of a sample pipetting device from which cleaning fluids are flowed from device cavities to wash a pipettor capillary element that extends from the device. As shown, device 2200 includes six wells (2202, 2204, 2206, 2208, 2210, and 2212, respectively), which fluidly communicate with microchannel network 2214 and from which cleaning fluids are optionally flowed to wash a pipettor capillary element (not viewable) via pipettor/device junction 2216. Device 2200 also includes a reverse swept joint to waste well 2218, while well 2220 is unused in this embodiment. While sample materials are typically only drawn into the pipettor capillary element, they are also optionally drawn into microchannel network 2214 in certain embodiments. FIG. 23 is graph (abscissa—sipping time (seconds); ordinate—column length (mm) that shows a sipping calibration performed using a device like the one schematically depicted in FIG. 22. The calibration was performed with a the volume of fluid passing a given point being 200 nl/minute and the velocity of fluid passing that point being 4 mm/second.

V. Microfluidic Devices Generally

Many different microscale systems are optionally adapted for use with the devices and methods of the present invention. Systems which can be modified according to the present invention are described in numerous publications by the inventors and their coworkers, including certain issued U.S. patents, such as U.S. Pat. Nos. 5,885,470 (J. Wallace Parce et al.) issued Mar. 23, 1999, 5,942,443 (J. Wallace Parce et al.) issued Aug. 24, 1999, 6,071,478 (Calvin Y. H. Chow) issued Jun. 6, 2000, and 6,235,471 (Michael Knapp et al.) issued May 22, 2001. Additional microscale systems which interface with mass spectrometers are described in U.S. Ser. No. 09/579,111, entitled "MICROSCALE ASSAYS AND MICROFLUIDIC DEVICES FOR TRANSPORTER, GRADIENT INDUCED, AND BINDING ACTIVITES," filed May 25, 2000 by Parce et al.; U.S. Pat. No. 6,231,737 and U.S. Pat. No. 6,110,343 to Ramsey et al. entitled "MATERIAL TRANSPORT METHOD AND APPARATUS;" and U.S. Pat. No. 5,872,010 to Karger et al. entitled MICROSCALE FLUID HANDLING SYSTEM.

The methods of the invention are generally performed within fluidic channels along which reagents, enzymes, samples, eluents, separation buffers, cleaning solutions, and other fluids are disposed and/or flowed. In some cases, as mentioned above, the channels are simply present in a capillary or pipettor element, e.g., a glass, fused silica, quartz or plastic capillary. The capillary element is fluidly coupled to a source of, e.g., the reagent, sample, modulator, or other solution (e.g., by dipping the capillary element into a well on a microtiter plate), which is then flowed along the channel (e.g., a microchannel) of the element. In preferred embodiments, the capillary element is integrated into the body structure of a microfluidic device. The term "microfluidic," as used herein, generally refers to one or more fluid passages, chambers or conduits which have at least one internal cross-sectional dimension, e.g., depth, width, length, diameter, etc., that is less than 500 μm, and typically between about 0.1 μm and about 500 μm.

In the devices of the present invention, the microscale channels or cavities typically have at least one cross-sectional dimension between about 0.1 μm and 200 μm, preferably between about 0.1 μm and 100 μm, and often between about 0.1 μm and 50 μm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "Y" and/or "T" intersections, or any number of other structures whereby two channels are in fluid communication.

The body structures of the microfluidic devices described herein are typically manufactured from two or more separate portions or substrates which when appropriately mated or joined together, form the microfluidic device of the invention, e.g., containing the channels and/or chambers described herein. During body structure fabrication, the microfluidic devices described herein will typically include a top portion, a bottom portion, and an interior portion, wherein the interior portion substantially defines the channels and chambers of the device. As mentioned, at least the separation region(s) of the devices of the present invention are optionally fabricated to include a chromatographic material (e.g., an anion exchange material, a cation exchange material, a hydrophobic exchange material, a hydrophilic exchange material, or the like) integral with and exposed on the inner surface of at least a portion of the microchannel(s) that include the separation region(s). Alternatively, as noted above, chromatographic materials are optionally flowed into the relevant portions of the device during device operation.

In one aspect, a bottom portion of the unfinished device includes a solid substrate that is substantially planar in structure, and which has at least one substantially flat upper surface. Channels are typically fabricated on one surface of the device and sealed by overlaying the channels with an upper substrate layer. A variety of substrate materials are optionally employed as the upper or bottom portion of the device. Typically, because the devices are microfabricated, substrate materials will be selected based upon their compatibility with known microfabrication techniques, e.g., photolithography, wet chemical etching, laser ablation, air abrasion techniques, LIGA, reactive ion etching, injection molding, embossing, and other techniques. The substrate materials are also generally selected for their compatibility with the full range of conditions to which the microfluidic devices may be exposed, including extremes of pH, temperature, electrolyte concentration, and/or for their chromatographic properties. Accordingly, in some preferred aspects, the substrate material may include materials normally associated with the semiconductor industry in which such microfabrication techniques are regularly employed, including, e.g., silica-based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. In preferred embodiments, at least the separation region(s) is/are fabricated from polyacrylamide, dimethylacrylamide, modified versions thereof, nonionic detergents, ionic detergents, or the like. Such polymeric substrates are readily manufactured using available microfabrication techniques, as described above, or from microfabricated masters, using known molding techniques, such as injection molding, embossing or stamping, or by polymerizing the polymeric precursor material within the mold (See, e.g., U.S. Pat. No. 5,512,131). Such polymeric substrate materials are preferred for their ease of manufacture, low cost and disposability, as well as their general inertness to most extreme reaction conditions. Again, these polymeric materials optionally include treated surfaces, e.g., derivatized or coated surfaces, to enhance their utility in the microfluidic system, e.g., to provide enhanced fluid direction, e.g., as described in U.S. Pat. No. 5,885,470 (J. Wallace Parce et al.) issued Mar. 23, 1999, and which is incorporated herein by reference in its entirety for all purposes.

The channels and/or cavities of the microfluidic devices are typically fabricated into the upper surface of the bottom substrate or portion of the device, as microscale grooves or indentations, using the above described microfabrication techniques. The top portion or substrate also comprises a first planar surface, and a second surface opposite the first planar surface. In the microfluidic devices prepared in accordance with certain aspects of the methods described herein, the top portion can include at least one aperture, hole or port disposed therethrough, e.g., from the first planar surface to the second surface opposite the first planar surface. In other embodiments, the port(s) are optionally omitted, e.g., where fluids are introduced solely through external capillary elements.

The first planar surface of the top portion or substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. Bonding of substrates is typically carried out by any of a number of different methods, e.g., thermal bonding, solvent bonding, ultrasonic welding, and the like. The finished body structure of a device is a unitary structure that houses, e.g., the channels and/or chambers of the device.

The hole(s) in the top of the finished device is/are oriented to fluidly communicate with at least one of the channels and/or cavities. In the completed device, the hole(s) optionally function as reservoirs for facilitating fluid or material introduction into the channels or chambers of the device, as well as providing ports at which, e.g., pressure elements (e.g., vacuum sources, etc.) are optionally placed into contact with fluids within the device, allowing application of pressure gradients along the channels of the device to control and direct fluid transport within the device. In optional embodiments, extensions are provided over these reservoirs to allow for increased fluid volumes, permitting longer running assays, and better controlling fluid flow parameters, e.g., hydrostatic pressures. Examples of methods and apparatuses for providing such extensions are described in U.S. Pat. No. 6,251,343, entitled "MICROFLUIDIC DEVICES AND SYSTEMS INCORPORATING COVER LAYERS," which issued Jun. 26, 2001 to Dubrow et al., and incorporated herein by reference. These devices are optionally coupled to a sample introduction port, e.g., a pipettor or capillary element, which serially introduces multiple samples, e.g., from the wells of a microtiter plate. Thus, in some embodiments, both reservoirs in the upper surface and external capillary elements are present in a single device.

The sources of reagents, enzymes, substrates, samples, eluents, separation buffers, and other materials are optionally fluidly coupled to the microchannels in any of a variety of ways. In particular, those systems comprising sources of materials set forth in Knapp et al. "Closed Loop Biochemical Analyzers" (WO 98/45481; PCT/US98/06723) and U.S. Pat. No. 5,942,443 issued Aug. 24, 1999, entitled "High Throughput Screening Assay Systems in Microscale Fluidic Devices" to J. Wallace Parce et al. and, e.g., in 60/128,643 filed Apr. 4, 1999, entitled "Manipulation of Microparticles In Microfluidic Systems," by Mehta et al. are applicable.

In these systems and as noted above, a capillary or pipettor element (i.e., an element in which components are optionally moved from a source to a microscale element such as a second channel or reservoir) is temporarily or permanently coupled to a source of material. The source is optionally internal or external to a microfluidic device that includes the pipettor or capillary element. Example sources include microwell plates, membranes or other solid substrates comprising lyophilized components, wells or reservoirs in the body of the microscale device itself and others.

VI. Flow of Materials in Microfluidic Systems

The microfluidic devices of the invention optionally include flowing fluids in microscale cavities (e.g., microchannel networks, etc.), capillary elements, or the like using various fluid direction components that optionally include, e.g., a fluid pressure force modulator, an electrokinetic force modulator, a capillary force modulator, a gravity force modulator, a magnetic force modulator, a dielectrophoretic force modulator, a fluid wicking element, or the like. The fluid direction components used to induce fluid movement in microfluidic device body structures and capillary elements or other fluid conduits are optionally the same or different. These as well as other fluid movement techniques which are optionally adapted to the devices disclosed herein are described in greater detail in the references cited and incorporated herein. In preferred embodiments, fluidic samples are electrosprayed from devices as described herein.

In certain embodiments, the methods of the invention include flowing materials along the microchannels or other cavities of the devices described herein is by pressure-based flow. Pressure is applied with or without a simultaneously applied electric field. Application of a pressure differential along a channel is carried out by any of a number of approaches. For example, it may be desirable to provide relatively precise control of the flow rate of materials, e.g., to precisely control incubation or separation times, etc. As such, in many preferred aspects, flow systems that are more active than hydrostatic pressure driven systems are employed. In certain cases, reagents may be flowed by applying a pressure differential across the length of the analysis channel. For example, a pressure source (positive or negative) is applied at the reagent reservoir at one end of the analysis channel, and the applied pressure forces the reagents through the channel. The pressure source is optionally pneumatic, e.g., a pressurized gas, or a positive displacement mechanism, i.e., a plunger fitted into a reagent reservoir, for forcing the reagents through the analysis channel. Alternatively, a vacuum source is applied to a reservoir at the opposite end of the channel to draw the reagents through the channel. Pressure or vacuum sources may be supplied external to the device or system, e.g., external vacuum or pressure pumps sealably fitted to the inlet or outlet of the analysis channel, or they may be internal to the device, e.g., microfabricated pumps integrated into the device and operably linked to the analysis channel. Examples of microfabricated pumps have been widely described in the art. See, e.g., published International Application No. WO 97/02357.

In an alternative simple passive aspect, the reagents are deposited in a reservoir or well at one end of an analysis channel and at a sufficient volume or depth, that the reagent sample creates a hydrostatic pressure differential along the length of the analysis channel, e.g., by virtue of it having greater depth than a reservoir at an opposite terminus of the channel. The hydrostatic pressure then causes the reagents to flow along the length of the channel. Typically, the reservoir volume is quite large in comparison to the volume or flow through rate of the channel, e.g., 10 µl reservoirs, vs. 1000 $\mu m^2$ channel cross-section. As such, over the time course of the assay/separation, the flow rate of the reagents will remain substantially constant, as the volume of the reservoir, and thus, the hydrostatic pressure changes very slowly. Applied pressure is then readily varied to yield different reagent flow rates through the channel. In screening applications, varying the flow rate of the reagents is optionally used to vary the incubation time of the reagents. In particular, by slowing the flow rate along the channel, one can effectively lengthen the amount of time between introduction of reagents and detection of a particular effect. Alternatively, analysis channel lengths, detection points, or reagent introduction points are varied in fabrication of the devices, to vary incubation times. See also, "Multiport Pressure Control System," by Chien and Parce, U.S. Ser. No. 60/184,390, filed Feb. 23, 2000, which describes multiport pressure controllers that couple pumps to multiple device reservoirs.

In further alternate aspects, hydrostatic, wicking and capillary forces are additionally, or alternately, used to provide for fluid flow. See, e.g., "Method and Apparatus for Continuous Liquid Flow in Microscale Channels Using Pressure Injection, Wicking and Electrokinetic Injection," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

In alternative aspects, flow of reagents is driven by inertial forces. In particular, the analysis channel is optionally disposed in a substrate that has the conformation of a rotor, with the analysis channel extending radially outward from the center of the rotor. The reagents are deposited in a reservoir that is located at the interior portion of the rotor and is fluidly connected to the channel. During rotation of the rotor, the centripetal force on the reagents forces the reagents through the analysis channel, outward toward the edge of the rotor. Multiple analysis channels are optionally provided in the rotor to perform multiple different analyses. Detection of a detectable signal produced by the reagents is then carried out by placing a detector under the spinning rotor and detecting the signal as the analysis channel passes over the detector. Examples of rotor systems have been previously described for performing a number of different assay types. See, e.g., Published International Application No. WO 95/02189. Test compound reservoirs are optionally provided in the rotor, in fluid communication with the analysis channel, such that the rotation of the rotor also forces the test compounds into the analysis channel.

For purposes of illustration, the discussion has focused on a single channel and accessing capillary; however, it will be readily appreciated that these aspects may be provided as multiple parallel analysis channels (e.g., each including mixing and separation regions) and accessing capillaries, in order to substantially increase the throughput of the system. Specifically, single body structures may be provided with multiple parallel analysis channels coupled to multiple sample accessing capillaries that are positioned to sample multiple samples at a time from sample libraries, e.g., multiwell plates. As such, these capillaries are generally spaced at regular distances that correspond with the spacing of wells in multiwell plates, e.g., 9 mm centers for 96 well plates, 4.5 mm for 384 well plates, and 2.25 mm for 1536 well plates.

In alternate aspects, an applied pressure is accompanied by the simultaneous application of an electric field to further effect fluid transport, e.g., through the mixing and/or separation regions of the microchannel. The electrokinetic transport systems of the invention typically utilize electric fields applied along the length of microchannels that have a surface potential or charge associated therewith. When fluid is introduced into the microchannel, the charged groups on the inner surface of the microchannel ionize, creating locally concentrated levels of ions near the fluid surface interface. Under an electric field, this charged sheath migrates toward the cathode or anode (depending upon whether the sheath comprises positive or negative ions) and pulls the encompassed fluid along with it, resulting in bulk fluid flow. This flow of fluid is generally termed electroosmotic flow. Where the fluid includes reagents (e.g., materials to be separated), the reagents are also pulled along. A more detailed description of controlled electrokinetic material transport systems in microfluidic systems is described in published International Patent Application No. WO 96/04547, which is incorporated herein by reference.

VII. Fluid Delivery Systems

The fluid delivery devices of the present invention are typically included as components of automated, high-throughput fluid delivery systems. Other system components typically include additional instrumentation for orienting, mating, and/or interchanging the devices disclosed herein, for controlling electric fields, fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format. An example system for orthogonally electrospraying fluidic materials is provided below.

Although the devices and systems specifically illustrated herein are generally described in terms of the performance of a few or one particular operation (e.g., fluid delivery), it will be readily appreciated from this disclosure that the flexibility of these systems permits easy integration of additional operations into these devices. For example, the devices and systems of the invention will optionally include structures, reagents and systems for performing virtually any number of operations in addition to the operations specifically described herein. Aside from fluid handling, assays, and separation of sample and/or reaction components, other upstream or downstream operations are also optionally performed, including, e.g., extraction, purification, amplification, cellular activation, labeling reactions, dilution, aliquotting, labeling of components, assays and detection operations, electrokinetic or pressure-based injection of components or materials into contact with one another, or the like. Assay and detection operations include, without limitation, cell fluorescence assays, cell activity assays, receptor/ligand assays, immunoassays, or the like.

A. Controllers

The controllers of the fluid delivery systems of the present invention direct dipping of capillary elements into, e.g., microwell plates to sample reagents, such as enzymes and substrates, fluid recirculation baths or troughs to wash capillary elements, or the like. A variety of controlling instrumentation is also optionally utilized in conjunction with the microfluidic devices and handling systems described herein, for controlling the transport, concentration, direction, and motion of fluids and/or separation of materials within the devices of the present invention, e.g., by pressure-based and/or electrokinetic control.

As described above, in many cases, fluid transport, concentration, and direction are controlled in whole or in part, using pressure-based flow systems that incorporate external or internal pressure sources to drive fluid flow. Internal sources include microfabricated pumps, e.g., diaphragm pumps, thermal pumps, and the like that have been described in the art. See, e.g., U.S. Pat. Nos. 5,271,724, 5,277,556, and 5,375,979 and Published PCT Application Nos. WO 94/05414 and WO 97/02357, which are incorporated by reference in their entirety for all purposes. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are also described in U.S. Ser. No. 09/238,467, filed Jan. 28, 1999, which is incorporated by reference in its entirety for all purposes.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

B. Detection Systems

The devices described herein optionally include signal detectors, e.g., which detect concentration, fluorescence, phosphorescence, radioactivity, pH, charge, absorbance, refractive index, luminescence, temperature, magnetism, mass, or the like. The detection systems optionally monitor one or a plurality of signals from upstream and/or downstream (e.g., in or proximal to a separation region) of an assay mixing point in which, e.g., a ligand and an enzyme are mixed. For example, the detector optionally monitors a plurality of optical signals, which correspond in position to "real time" assay/separation results.

In preferred embodiments, detection systems of the invention include mass spectrometers, e.g., atmospheric or sub-atmospheric ionization mass spectrometers. Especially preferred mass detectors for use in the methods and systems of the invention include electrospray ionization mass spectrometers, which can, e.g., be positioned proximal to or coupled to one or more microscale channels of a device. Mass spectrometric systems that are optionally adapted for use with the sample delivery devices of the invention are generally known in the art. Some of these systems are described further in, e.g., Skoog, et al. *Principles of Instrumental Analysis* ($5^{th}$ Ed.) Hardcourt Brace & Company, Orlando (1998), Busch and Lehman, *Guide to Mass Spectrometry*, V C H Publishers, Inc. (1999), Watson, *Introduction to Mass Spectrometry*, $3^{rd}$, Lippincott-Raven Publishers (1997), Barker et al., *Mass Spectrometry*, $2^{nd}$, John Wiley & Sons, Inc. (1999), Stroobant, *Mass Spectrometry: Principles and Applications*, $2^{nd}$, John Wiley & Sons, Inc. (2001), Housby, *Mass Spectrometry and Genomic Analysis*, Kluwer Academic Publishers (2001), and Siuzdak, *Mass Spectrometry for Biotechnology*, Academic Press, Inc. (1996), which are incorporated by reference in their entirety for all purposes. Additional sources of information relating to interfacing mass spectrometers with microfluidic devices include, e.g., Karger, et al., U.S. Pat. No. 5,571,398, "PRECISE CAPILLARY ELECTROPHORETIC INTERFACE FOR SAMPLE COLLECTION OR ANALYSIS" and Karger, et al. U.S. Pat. No. 5,872,010 "MICROSCALE FLUID HANDLING SYSTEM," which are incorporated by reference in their entirety for all purposes. In general, mass spectrometers are well suited to interface with microfluidic devices, e.g., because the usual input into a microfluidic system is a capillary channel. Methods of affixing external capillaries to microscale systems include various bonding and/or drilling operations, as described, e.g., in Parce, et al., U.S. Pat. No. 5,972,187 "ELECTROPIPETTOR AND COMPENSATION MEANS FOR ELECTROPHORETIC BIAS," which is incorporated by reference in its entirety for all purposes.

Other detectors optionally used, or adapted for use, in the systems of the present invention include, e.g., an optical detector, a microscope, a CCD array, a photomultiplier tube, a photodiode, an emission spectroscope, a fluorescence spectroscope, a phosphorescence spectroscope, a luminescence spectroscope, a spectrophotometer, a photometer, a nuclear magnetic resonance spectrometer, an electron paramagnetic resonance spectrometer, an electron spin resonance spectroscope, a turbidimeter, a nephelometer, a Raman spectroscope, a refractometer, an interferometer, an x-ray diffraction analyzer, an electron diffraction analyzer, a polarimeter, an optical rotary dispersion analyzer, a circular dichroism spectrometer, a potentiometer, a chronopotentiometer, a coulometer, an amperometer, a conductometer, a gravimeter, a mass spectrometer, a thermal gravimeter, a titrimeter, a differential scanning colorimeter, a radioactive activation analyzer, a radioactive isotopic dilution analyzer, or the like.

To further illustrate, example detectors or sensors include photomultiplier tubes, CCD arrays, optical sensors, temperature sensors, pressure sensors, pH sensors, conductivity sensors, mass sensors, scanning detectors, or the like. Materials which emit a detectable signal are optionally flowed past the detector, or, alternatively, the detector can move relative to the device or other system components to determine the position of an assay component (or, the detector can simultaneously monitor a number of spatial positions corresponding to channel regions, e.g., as in a CCD array). Each of these types of sensors is optionally readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. The detector optionally includes or is operably linked to a computer, e.g., which has software for converting detector signal information into assay result information (e.g., kinetic data of modulator activity), or the like. A microfluidic system optionally employs multiple different detection systems for monitoring the output of the system. Detection systems of the present invention are used to detect and monitor the materials in a particular channel region (or other reaction detection region).

In certain embodiments, detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the spectral characteristics of the materials. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs), or the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as labeled cells, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes, and LEDs. Other light sources optionally used in the detection systems of the invention include, e.g., broad band light sources which are typically used in light scattering/transmissivity detection schemes, and the like. In general, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detection system, and the computer.

C. Computers

As noted above, the microfluidic devices and integrated systems of the present invention optionally include a computer operably connected to the controller. The computer typically includes an instruction set, e.g., for varying or selecting a rate or a mode of dipping capillary or pipettor elements into fluid materials, for sampling fluidic materials (e.g., enzymes, substrates, reactants, chromatographic materials, eluents, separation buffers, etc.), or the like. Additionally, either or both of the controller system and/or the detection system is/are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation, e.g., varying or selecting the rate or mode of fluid and/or microfluidic device movement, controlling flow rates within microscale channels, directing X-Y-Z translation of the microfluidic device or of one or more microwell plates, electrospraying sample aliquots into mass spectrometric system inlets, or the like. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like. Additionally, the software is optionally used to control, e.g., pressure or electrokinetic modulated injection or withdrawal of material.

VIII. Examples

The following non-limiting examples are offered only by way of illustration.

A. Example Orthogonal Electrospray System

Figure 24:
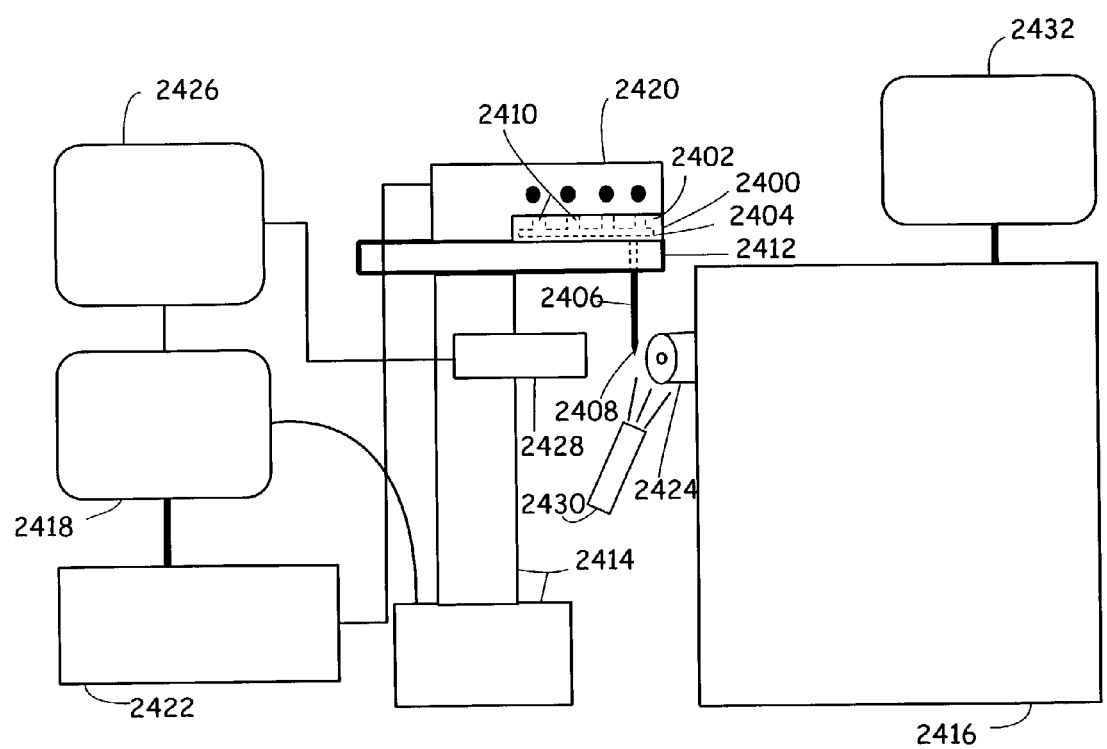
FIG. 24 schematically illustrates a system for orthogonally electrospraying sample materials.

FIG. 24 schematically illustrates a system for orthogonally electrospraying sample materials into an orifice of a mass spectrometric detection system. As shown, body structure 2402 of microfluidic device 2400 has microchannel 2404 disposed therein. Many different microchannel configurations are possible and available for use in the devices of the present invention. Additional alternatives can be devised, e.g., by combining the microfluidic elements described herein, e.g., mixing regions, separation regions, or the like, with other microfluidic components described in the patents and applications referenced herein. Microfluidic device 2400 also includes capillary element 2406 attached to body structure 2402, which fluidly communicates with microchannel 2404. Capillary element 2406 also includes tapered spray tip 2408 from which samples are orthogonally electrosprayed. In certain embodiments, at least microchannel 2404 includes a chromatographic material (e.g., coating, or as an integral component of, an inner surface) in a separation region. A device similar to microfluidic device 2400 is schematically illustrated in FIG. 2, which is described above. Microfluidic device 2400 also includes ports 2410, which fluidly communicate with microchannel 2404. Microfluidic device 2400 is positioned on stage 2412 of device handling system 2414. Device handling system 2414 generally controls, e.g., the X-Y-Z translation of microfluidic device 2400 relative to microwell plates or other samples sources (not shown), mass spectrometer detection system 2416 (e.g., a quadrupole mass spectrometer, time-of-flight mass spectrometer, or the like), or other system components, under the direction of computer 2418 (e.g., a PC controller, etc.) to which device handling system 2414 is typically operably connected.

Manifold 2420 operably connects fluid direction system 2422 (e.g., a pressure/voltage controller, etc.) to microfluidic device 2400 via, e.g., ports 2410, e.g., to control pressure (e.g., a vacuum coupling, etc.) and/or voltage within microfluidic device 2400, e.g., to effect fluid movement in microchannel 2404 and to electrospray samples from tapered spray tip 2408. Fluid direction system 2422 is also typically operably connected to computer 2418, which directs its operation. In one set of embodiments, computer 2418 uses signal information to select further parameters for the system. For example, upon detecting (e.g., using mass spectrometer detection system 2416) the presence of a component of interest (e.g., following separation) in a sample, computer 2418 optionally directs addition of a potential modulator of the component of interest into the system.

During operation, device handling system 2414 generally positions tapered spray tip 2408 proximate to orifice 2424 of mass spectrometer detection system 2416 and fluid direction system 2422 applies sufficient voltage to bias fluidic materials within capillary element 2406 such that they are orthogonally electrosprayed from tapered spray tip 2408 into orifice 2424 for detection. For example, FIG. 1 is a photograph that shows a sample aliquot being orthogonally electrosprayed from a tapered spray tip of a capillary element to an orifice of a mass spectrometer. FIG. 1 is described in greater detail above. Further, in the embodiment depicted in FIG. 24, the system also includes spray monitor 2426, which is operably connected to computer 2418, which directs its operation. Camera 2428 is operably connected to spray monitor 2426 and provides video signals of, e.g., samples being electrosprayed from tapered spray tip 2408 into orifice 2424, which are viewable on spray monitor 2426. Light source 2430 is also typically included provide illumination for camera 2428. As additionally shown, computer 2432 (e.g., a PC controller, etc.) is operably connected to mass spectrometer detection system 2416. Computer 2432 typically digitizes, stores, and manipulates signal information detected by mass spectrometer detection system 2416, e.g., using an instruction set, e.g., for correlating detected mass-to-charge ratios with particular molecular components for identification. Optionally, computer 2432 is networked or otherwise operably connected to computer 2418. In other embodiments, the system includes only a single computer operably connected to the system components.

B. Reserpine Assays

Figure 25A:
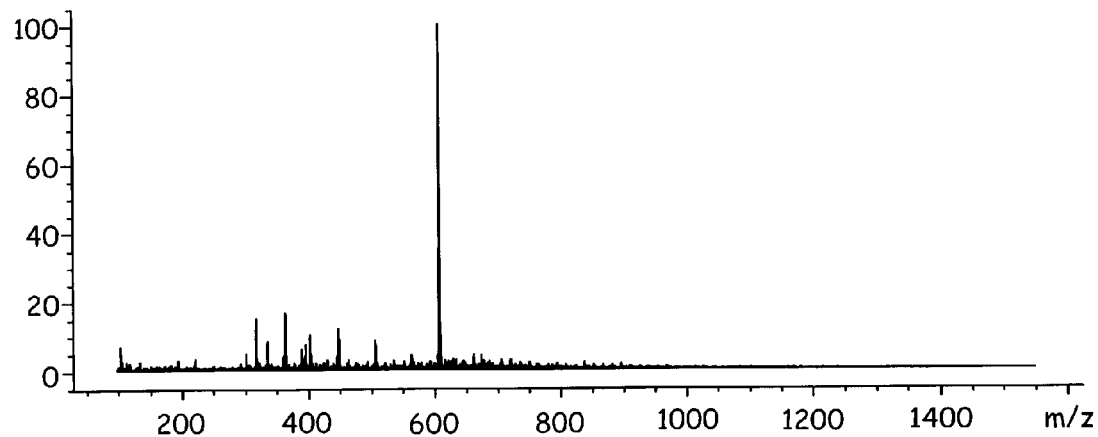
FIGS. 25A and B are mass spectral traces showing detected components from a reserpine analysis.
Figure 25B:
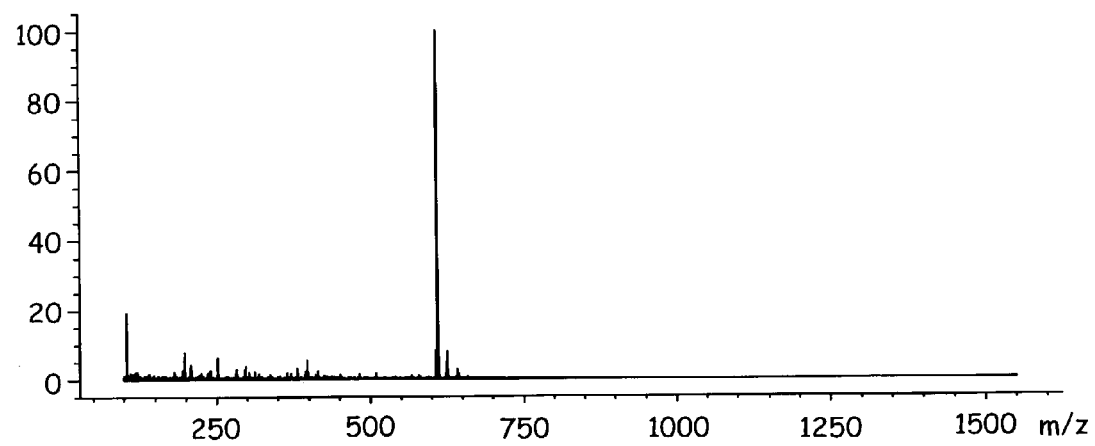

FIGS. 25A and B are mass spectral traces (abscissa—mass-to-charge ratio (m/z); ordinate—relative intensity) showing detected components from certain reserpine analyses. The samples of reserpine assayed had concentrations of 500 pg/μm. In particular, FIG. 25A shows a mass spectral trace obtained when an aliquot of the reserpine sample was flowed from a well of a microfluidic device and sprayed from a capillary element of the device. As shown, the sample was contaminated by epoxy from the joint between the device body structure and the capillary element, as indicated by the signal at m/z=365.2. In contrast, FIG. 25B shows a mass spectral trace obtained when an aliquot of the reserpine sample was drawn (i.e., pipetted) only into the capillary element and the proximal section of the chip from an external source and subsequently sprayed from the capillary. As shown, no epoxy contamination was detected.

FIGS. 26A-C are mass spectral traces (abscissa—mass-to-charge ratio (m/z); ordinate—relative intensity) showing detected components from a reserpine comparison.

FIG. 26A is a mass spectral trace obtained when an aliquot of a reserpine sample was flowed from a well of a device and sprayed from a capillary element having a pico-tip™ (New Objective, Inc., Woburn, Mass.) at a flow rate of 280 nl/minute. FIG. 26B is a mass spectral trace obtained when an aliquot of a reserpine sample was sprayed from a device at a flow rate of 33 μl/minute using a syringe pump. FIG. 26C is a mass spectral trace obtained when an aliquot of a reserpine sample was sprayed from a tapered capillary tip of a device at a flow rate of 480 nl/minute. As shown, the mass spectral trace shown in FIG. 26C had the best signal to noise ratio of the three mass spectra obtained.

Figure 27A:
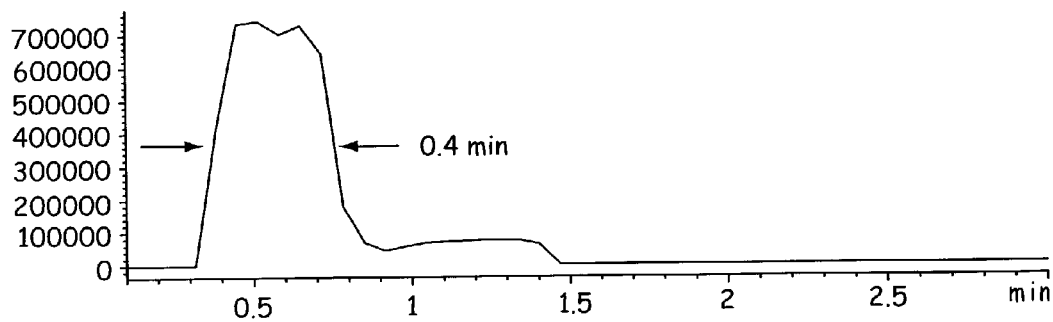
FIGS. 27A-G are data graphs showing results obtained from an analysis in which reserpine was infused from a microfluidic device.
Figure 27B:
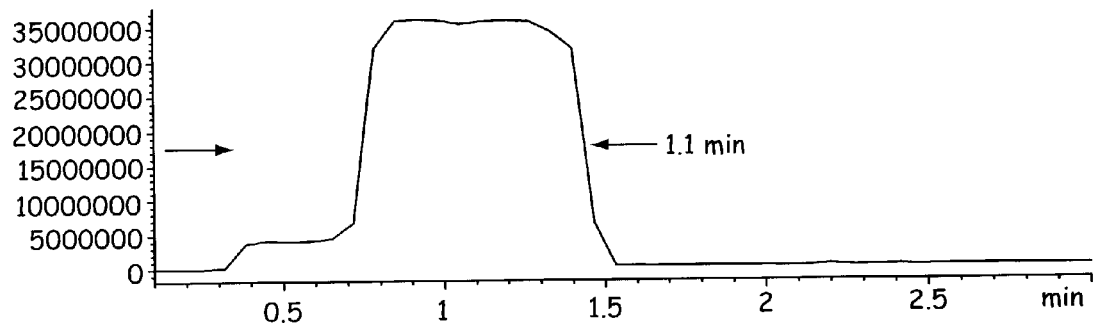
Figure 27C:
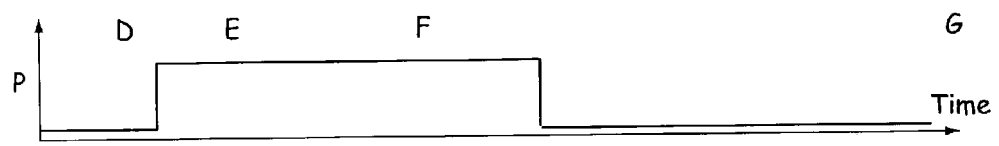
Figure 27D:
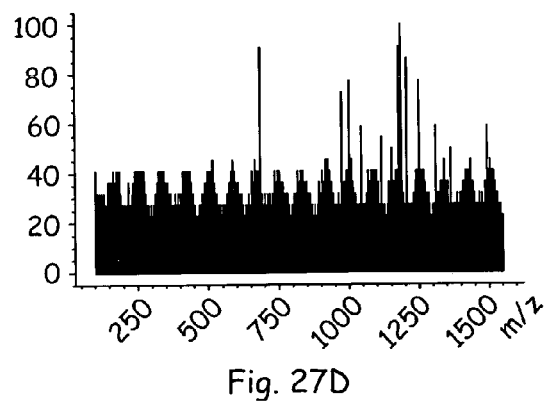
Figure 27E:
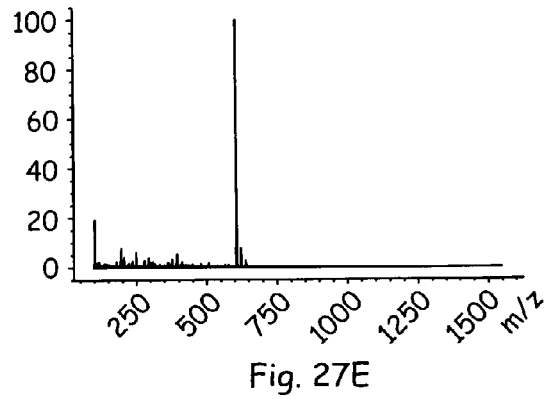
Figure 27F:
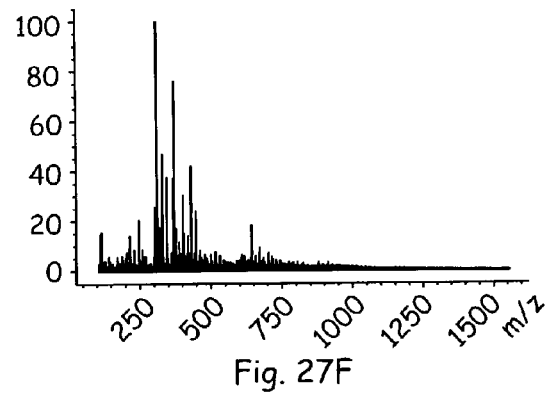
Figure 27G:
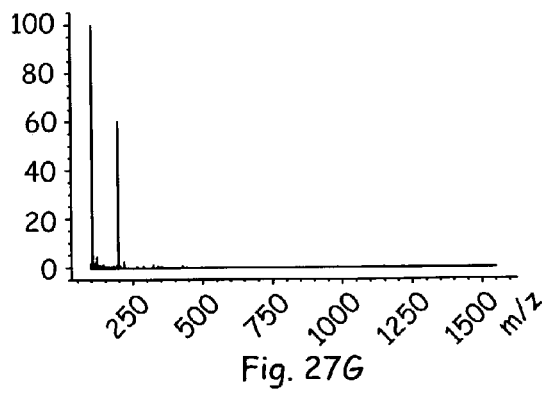

FIGS. 27A-G are data graphs showing results obtained from an analysis in which reserpine was infused from a microfluidic device. The assay involved sipping a reserpine sample for 24 seconds at a flow rate of 8 nl/second for a total volume of 192 nl, which was then sprayed by turning on the pump for about 60 seconds. FIG. 27A is a graph (abscissa—time (minutes); ordinate—signal intensity) showing a signal at m/z=609, obtained for the Reserpine sample sprayed for about 0.4 minutes (192 nl/0.4 minutes=480 nl/minute). FIG. 27B is a graph (abscissa—time (minutes); ordinate—signal intensity) showing a signal obtained for the total ion current sample sprayed for about 1.1 minutes. FIG. 27C is a schematic graph (abscissa—time (minutes); ordinate—signal intensity) corresponding to the pump pressure shown in FIGS. 27A and B. FIG. 27D is a mass spectral trace (abscissa—mass-to-charge ratio (m/z); ordinate—relative intensity) obtained at time D in FIG. 27C, indicating only noise when the pump is off. FIG. 27E is a mass spectral trace (abscissa—mass-to-charge ratio (m/z); ordinate—relative intensity) obtained at time E in FIG. 27C, indicating a strong signal corresponding to Reserpine. FIG. 27F is a mass spectral trace (abscissa—mass-to-charge ratio (m/z); ordinate—relative intensity) obtained at time F in FIG. 27C, indicating the end of the bolus of Reserpine. FIG. 27G is a mass spectral trace (abscissa—mass-to-charge ratio (m/z); ordinate—relative intensity) obtained at time G in FIG. 27C, indicating the end of the spray.

Figure 28A:
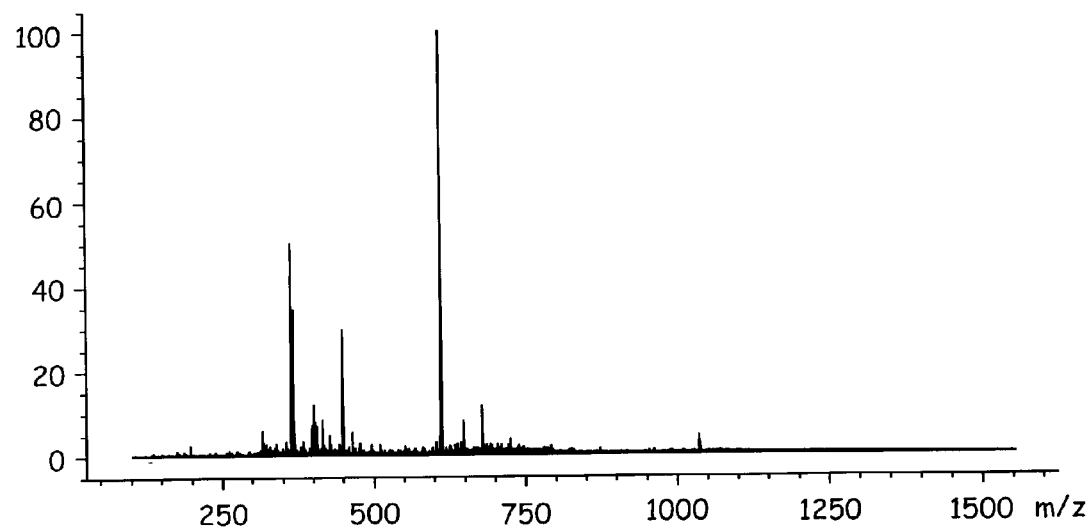
FIGS. 28A and B are mass spectral traces showing detected components from a reserpine assay that compared axial and orthogonal spraying.
Figure 28B:
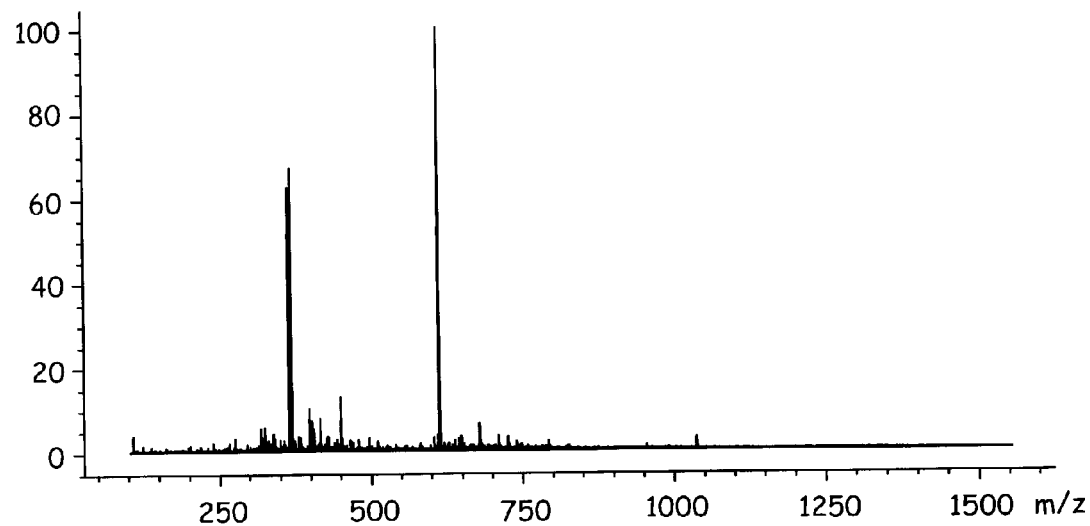

FIGS. 28A and B are mass spectral traces (abscissa—mass-to-charge ratio (m/z); ordinate—relative intensity) showing detected components from a reserpine assay that compared axial and orthogonal spraying. The assays included flowing aliquots of a reserpine sample (5 ng/μl) from a well of a microfluidic device, which were then sprayed from a capillary element that extended from the device. FIG. 28A is a mass spectral trace obtained when a reserpine aliquot was axially sprayed from the device under 2 psi of pressure at 2 KV. FIG. 28B is a mass spectral trace obtained when a reserpine aliquot was orthogonally sprayed from the same device under 5 psi of pressure at 3 KV. As shown, although the flow rate of the orthogonally sprayed aliquot was over two times greater than the flow rate of the axially sprayed aliquot, comparable signal to noise ratios were obtained, and further indicate that comparable signal to noise ratios may be possible at equivalent flow rates.

C. Detection of Proteins

One significant embodiment of the invention is the use of the devices, systems and methods of the invention for the detection of proteins and protein fragments ("proteomics"). This detection can be of partially or fully purified proteins or peptide fragments, with peptide/protein purification and/or fragmentation steps optionally occurring in the microfluidic system. See also, Lazar et al. (1999) "Subattomole-Sensitivity Microchip Nanoelectrospray Source with Time of Flight Mass Spectrometry Detection," *Analytical Chemistry* 71(17): 3627-3631; and Lazar et al. (2001) "On-Chip Proteolytic Digestion and Analysis Using "Wrong Way Round" Electrospray Time of Flight Mass Spectrometry *Analytical Chemistry* 73(8): 1733-1739.

Figure 29:
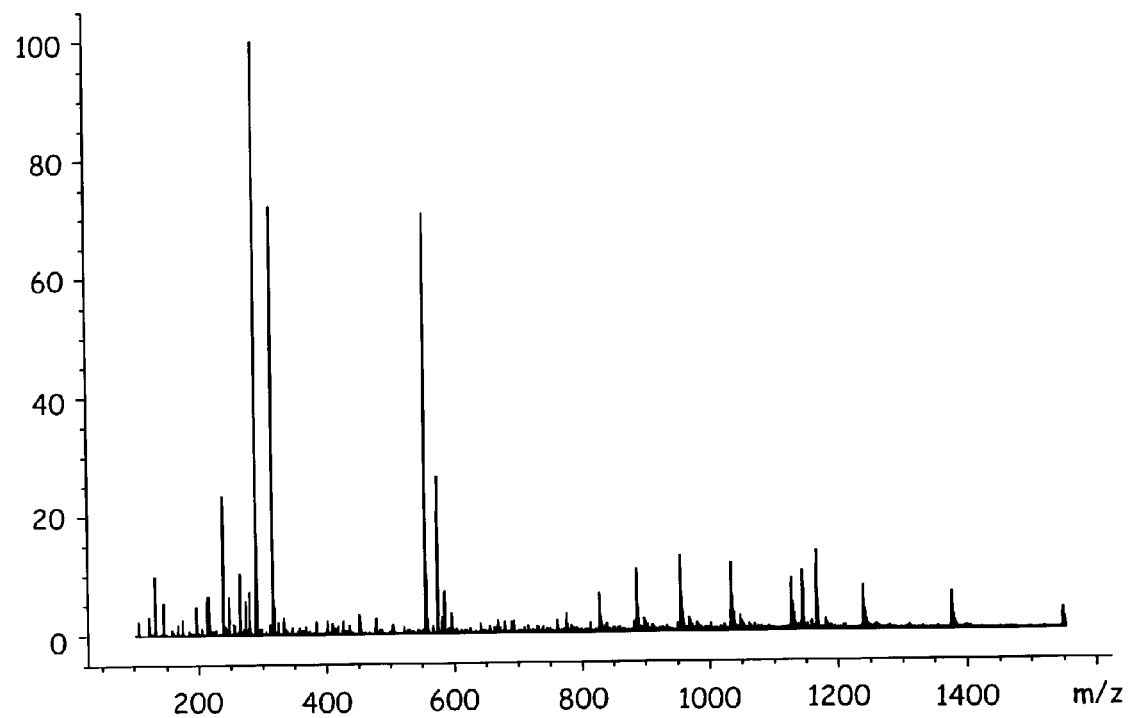
FIG. 29 is a Mass Spectral trace of a cytochrome C experiment.
Figure 30:
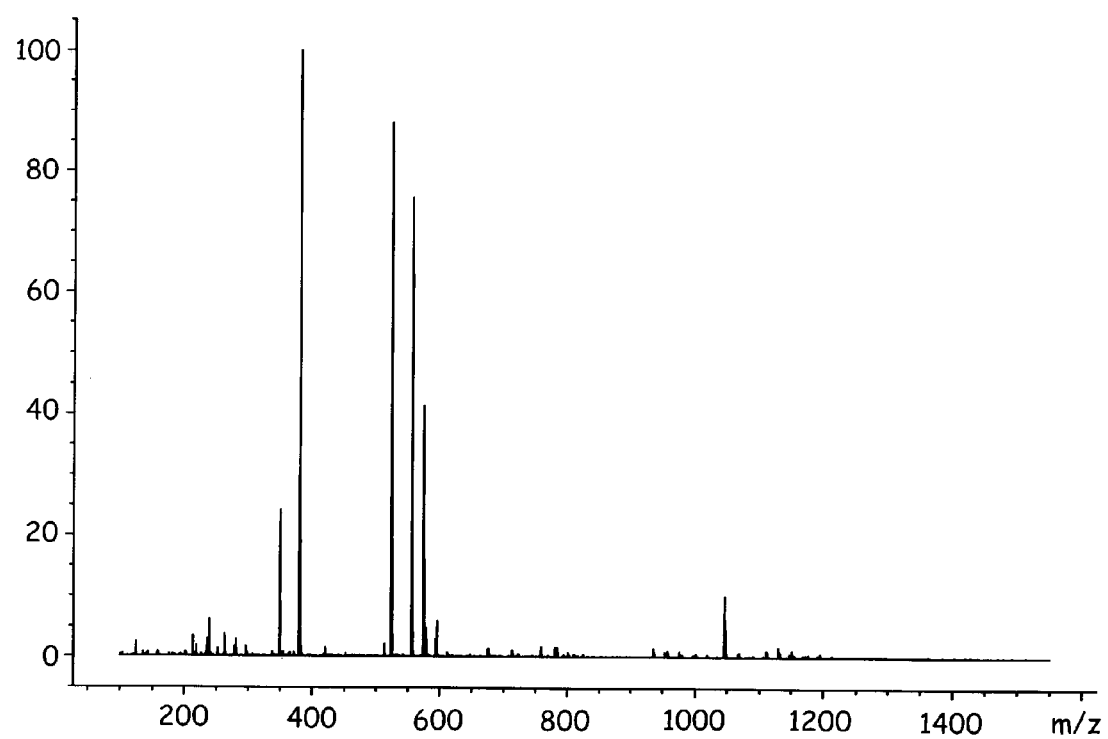
FIG. 30 is a Mass Spectral trace of HPLC purified peptides.
Figure 31A:
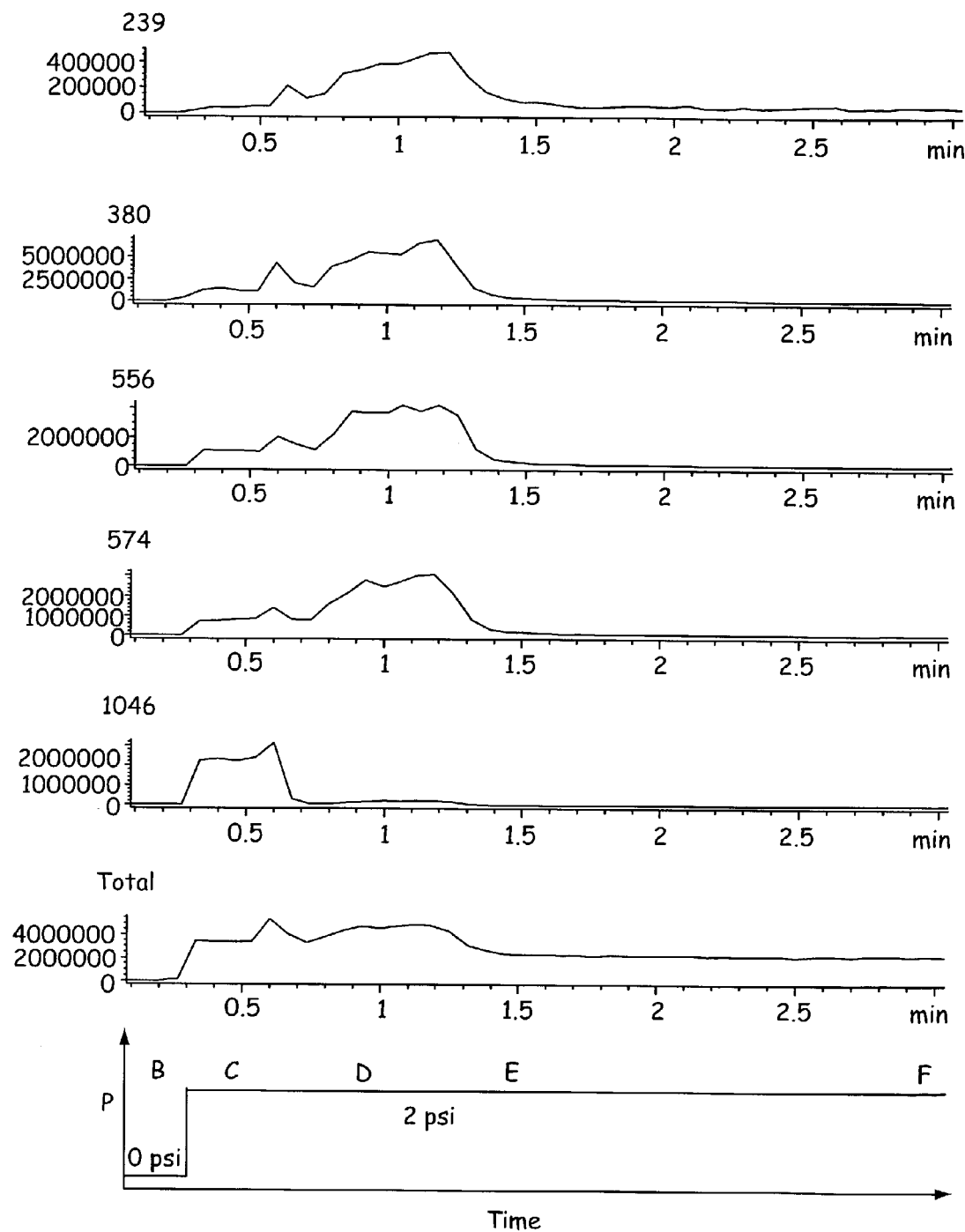
FIG. 31 is a Mass Spectral trace of a pipettor experiment showing a time course for HPLC purified peptides.
Figure 31B:
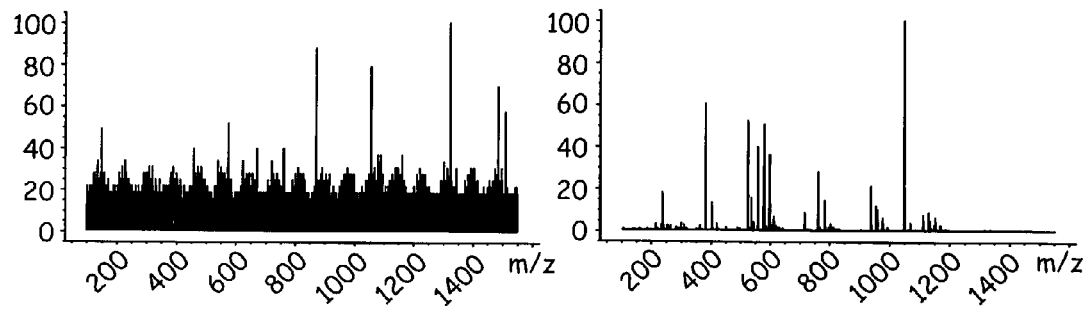
Figure 31C:
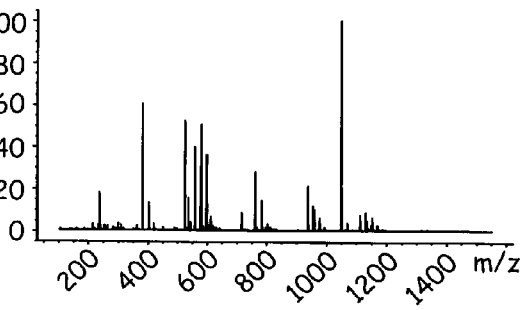
Figure 31D:
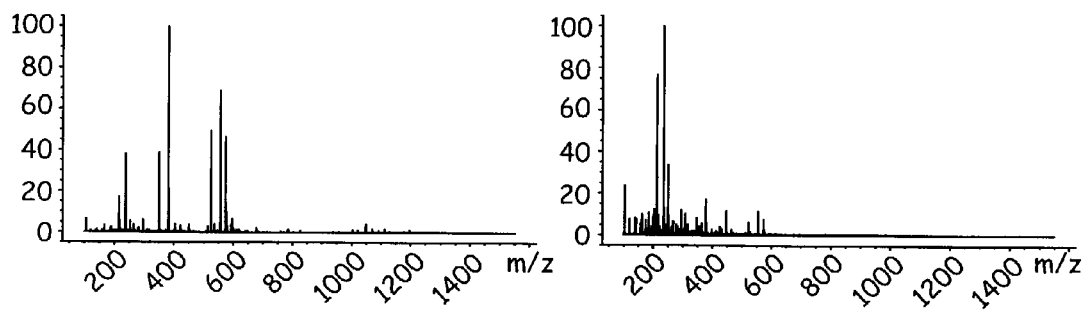
Figure 31E:
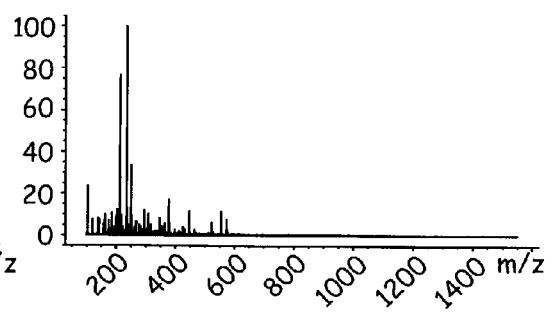
Figure 31F:
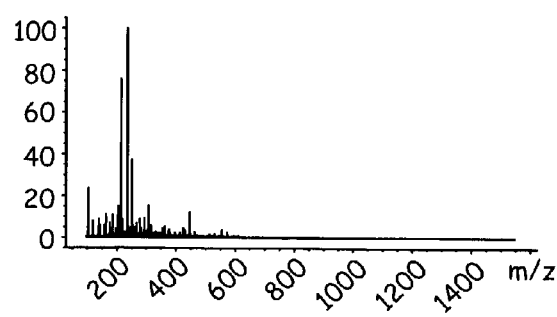

Example protein and peptide detection experiments in accordance with the invention are illustrated by FIGS. 29-31. The Figures depict results of electrospray MS from a microfluidic chip, using 8 μm ID Pico-Tips, a 2000-3000 V bias voltage, and about 50-100 nl/min flow rate. FIG. 29 shows a scan of Cytochrome C at a concentration of 100 nM in water. The operating conditions were 1 psi pressure and 3000 V bias.

Cytochrome C peaks are seen from 824.9 (+15 charge state) to 1374.1 (+8 charge state). Gramicidin S was also present in this sample leading to peaks around 570. The peak at 1163.7 is an impurity.

FIG. 30 provides the results of an MS scan from a mixture of HPLC purified peptides having individual concentration of 10 ng/ul in 50% Methanol water, and expected m/z peaks of 239 (Gly-Tyr), 380 (Val-Tyr-Val), 556 (Leucine enkephlin), 574(Methionine enkephlin) and 1046(Angiotensin UI). The peptide at 1046 (Angiotensin II) is also seen as a 2+ and $3^+$ charge state at m/z of 524 and 349, respectively. The operating conditions were 1 psi pressure and 2000 V bias.

FIG. 31 provides the results of a pipetting experiment on the same HPLC peptide mixture, under the same operating conditions of pressure and bias voltage. In this experiment, 21 mm of the peptide mix were sipped into a 50 um ID fused Silica capillary attached to a microfluidic system by applying vacuum and, after a short delay, the pressure in the system was adjusted to 2 psi. The electrospray rate was calculated as 23 mm/min×2 nl/mm=46 nl/min. Spectra were taken at the 4 time points indicated. As shown, at time point 0, only noise was observed, with no substantial flow of peptides into the MS being detected. At time point 1, all expected species in the mixture are seen, dominated by Angiotensin II with a MW of 1046. At time point 2, the bulk of the expected components are observed, with the peak at 1046 almost gone. At time point 3, the peak at 1046 is gone and detection of the rest of the peptide components drops off. At time point 4, mostly just noise is observed, with some remaining detection of the peptide with a MW of 239.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A microfluidic device, comprising:
    a body structure comprising:
    a substrate comprising one or more microscale cavities and at least one flexible capillary element, said at least one capillary element extending from the substrate, said at least one capillary element in fluid communication with at least one of the one or more microscale cavities, said at least one capillary element comprising a tapered spray tip, wherein a segment of said capillary element or at least one of said microscale cavities comprises a conductive coating;
    a fluid direction component operably connected to the body structure, which fluid direction component is configured to introduce selected aliquots of a fluidic sample into the tapered spray tip from a sample source located external to the body structure of the microfluidic device and spray the selected aliquots from the tapered spray tip proximal to or within a sample destination; and
    at least one device handling system operably connected to the device, said device handling system comprising at least one controller capable of flexing the tapered spray tip of the capillary element between the sample source and the sample destination.

2. The microfluidic device of claim 1, wherein the segment of the capillary element or the at least one of said microscale cavities is operably connected to a power source whereby a potential gradient is created in the segment.

3. The microfluidic device of claim 1, wherein the tapered spray tip comprises a nozzle.

4. The microfluidic delivery device of claim 1, wherein the fluid direction component comprises a fluid pressure force modulator, an electrokinetic force modulator, or both.

5. The microfluidic sample delivery device of claim 1, further comprising:
    at least one electrical control system operably connected to at least the tapered spray tip and the sample destination, which electrical control system is capable of generating a potential difference between the tapered spray tip and the sample destination to electrospray the selected aliquots from the tapered spray tip proximal to the sample destination.

6. The microfluidic device of claim 1, wherein the at least one or more microscale cavities comprise at least one channel region, said channel region comprising a separation region.

7. The microfluidic device of claim 6, wherein the separation region comprises a chromatographic material.

8. The microfluidic device of claim 1, wherein the one or more microscale cavities comprise a plurality of parallel microscale channels.

9. The microfluidic device of claim 8, comprising a plurality of capillary elements, each of said plurality of capillary elements being in fluid communication with at least one of the plurality of microscale channels.

10. The microfluidic device of claim 4, wherein the fluid direction component comprises an electrokinetic force modulator which is capable of applying a potential gradient along a length of the one or more microscale cavities or the capillary element to spray the selected aliquots from the tapered spray tip proximal to the sample destination.

11. The microfluidic sample delivery device of claim 1, wherein at least a portion of the tapered spray tip comprises a conductive coating.

12. The microfluidic sample delivery device of claim 1, wherein the at least one controller flexes the tapered spray tip of the capillary element approximately 90°.

13. A microfluidic system, comprising:
- a microfluidic device comprising a body structure including a substrate comprising one or more microscale cavities and at least one flexible capillary element, said at least one capillary element extending from the substrate, said at least one capillary element in fluid communication with at least one of the one or more microscale cavities, said at least one capillary element comprising a tapered spray tip, wherein a segment of said capillary element or at least one of said microscale cavities comprises a conductive coating;
- a fluid direction component operably connected to the body structure, which fluid direction system is configured to introduce selected aliquots of a fluidic sample into at least the capillary element the tapered spray tip from a sample source located external to the body structure of the microfluidic device and spray the selected aliquots from the tapered spray tip proximal to or within a sample destination; and
- at least one device handling system operably connected to the microfluidic device, which device handling system is capable of selectively moving the microfluidic device relative to the sample destination, said device handling system comprising at least one controller, which controller is capable of flexing the tapered spray tip of the capillary element between the sample source and the sample destination.

14. The microfluidic system of claim 13, wherein the device handling system is capable of translocating or rotating the microfluidic device between a the sample source and the sample destination.

15. The microfluidic system of claim 13, wherein at least a portion of the tapered spray tip comprises a conductive coating.

16. The microfluidic system of claim 13, wherein the at least one controller flexes the tapered spray tip of the capillary element approximately 90°.

17. The microfluidic system of claim 13, wherein the fluid direction system comprises one or more of: an electrokinetic fluid flow modulator and a fluid pressure force modulator.

18. The microfluidic system of claim 13, wherein the one or more microscale cavities comprises a plurality of parallel microscale channels.

19. The microfluidic system of claim 18, comprising a plurality of capillary elements with each of said plurality of capillary elements being in fluid communication with at least one of said plurality of microscale channels, and further wherein each of said plurality of capillary elements has a tapered spray tip.

* * * * *